(12) United States Patent
Taniyama et al.

(10) Patent No.: US 10,227,396 B2
(45) Date of Patent: Mar. 12, 2019

(54) ANTIBODY AGAINST PEPTIDE ENCODED BY EXON-21 OF PERIOSTIN AND PHARMACEUTICAL COMPOSITION FOR PREVENTING OR TREATING INFLAMMATION-ASSOCIATED DISEASES CONTAINING THE SAME

(71) Applicant: OSAKA UNIVERSITY, Osaka (JP)

(72) Inventors: Yoshiaki Taniyama, Osaka (JP); Ryuichi Morishita, Osaka (JP); Junya Azuma, Osaka (JP); Fumihiro Sanada, Osaka (JP); Naruto Katsuragi, Hyogo (JP)

(73) Assignee: OSAKA UNIVERSITY, Osaka (JP)

( * ) Notice: Subject to any disclaimer, the term of this patent is extended or adjusted under 35 U.S.C. 154(b) by 80 days.

(21) Appl. No.: 14/772,122

(22) PCT Filed: Mar. 6, 2014

(86) PCT No.: PCT/JP2014/055861
§ 371 (c)(1),
(2) Date: Dec. 1, 2015

(87) PCT Pub. No.: WO2014/136910
PCT Pub. Date: Sep. 12, 2014

(65) Prior Publication Data
US 2016/0108109 A1    Apr. 21, 2016

(30) Foreign Application Priority Data
Mar. 8, 2013  (JP) .................. 2013-047097

(51) Int. Cl.
| | | |
|---|---|---|
| A61K 39/395 | (2006.01) | |
| C07K 16/18 | (2006.01) | |
| C12N 5/12 | (2006.01) | |
| C07K 14/47 | (2006.01) | |
| G01N 33/68 | (2006.01) | |
| A61K 39/00 | (2006.01) | |

(52) U.S. Cl.
CPC .............. *C07K 16/18* (2013.01); *C07K 14/47* (2013.01); *C12N 5/12* (2013.01); *G01N 33/68* (2013.01); *A61K 2039/505* (2013.01); *C07K 2317/14* (2013.01); *C07K 2317/34* (2013.01); *C07K 2317/73* (2013.01); *C07K 2317/76* (2013.01); *G01N 2333/47* (2013.01)

(58) Field of Classification Search
None
See application file for complete search history.

(56) References Cited

U.S. PATENT DOCUMENTS

| | | | |
|---|---|---|---|
| 5,756,664 A | 5/1998 | Amann et al. | |
| 7,087,727 B2 * | 8/2006 | Chen ................... | C07K 14/475 435/332 |
| 8,017,119 B2 * | 9/2011 | Taniyama ............. | C07K 16/18 424/138.1 |
| 9,650,638 B2 * | 5/2017 | Suh ...................... | C12N 15/115 |
| 2003/0073137 A1 | 4/2003 | Chen et al. | |
| 2004/0029827 A1 | 2/2004 | Kawashima et al. | |
| 2005/0042642 A1 | 2/2005 | Monahan et al. | |
| 2006/0228763 A1 | 10/2006 | Chen et al. | |
| 2009/0028793 A1 | 1/2009 | Neri et al. | |
| 2009/0074788 A1 | 3/2009 | Taniyama et al. | |
| 2010/0075325 A1 * | 3/2010 | Monahan ............. | C12Q 1/6886 435/6.13 |
| 2012/0087862 A1 | 4/2012 | Hood et al. | |

FOREIGN PATENT DOCUMENTS

| | | |
|---|---|---|
| CA | 2 690 888 | 12/2008 |
| EP | 2 168 599 | 3/2010 |
| JP | 5-268982 | 10/1993 |
| JP | 2005-500059 | 1/2005 |
| JP | 2007-504842 | 3/2007 |
| JP | 2009-528820 | 8/2009 |
| JP | 2010/500568 | 1/2010 |
| JP | 5019464 | 6/2012 |
| JP | 5238942 | 4/2013 |
| WO | 02/20055 | 3/2002 |
| WO | 2005/019471 | 3/2005 |
| WO | 2007/077934 | 7/2007 |
| WO | 2009/001940 | 12/2008 |
| WO | 2011/024114 | 3/2011 |

OTHER PUBLICATIONS

Isono et al. Suppression of cell invasiveness by periostin via TAB1/TAK1. International Journal of Oncology 35: 425-432, 2009.*
Kyutoku, M. et al, "Role of periostin in cancer progression and metastasis: inhibition of breast cancer progression and metastasis by anti-periostin antibody in a murine model," International Journal of Molecular Medicine, Aug. 2011, vol. 28(2), pp. 181-186.*
Rani et al. Periostin-Like-Factor and Periostin in an Animal Model of Work-Related Musculoskeletal Disorder (Bone. Mar. 2009 ; 44(3): 502-512).*
Bendayan M. Possibilities of false immunocytochemical results generated by the use of monoclonal antibodies: the example of the anti-proinsulin antibody. J Histochem Cytochem. 43(9):881-6, 1995. (Year: 1995).*
Bost KL, Pascual DW. Antibodies against a peptide sequence within the HIV envelope protein crossreacts with human interleukin-2. Immunol Invest. 17(6-7):577-86, 1988. (Year: 1988).*
Kim et al. Opposite regulation of epithelial-to-mesenchymal transition and cell invasiveness by periostin between prostate and bladder cancer cells. Int J Oncol. Jun. 2011;38(6):1759-66 (Year: 2011).*
Orecchia et al. Identification of a novel cell binding site of periostin involved in tumour growth. Eur J Cancer. Sep. 2011;47(14):2221-9. (Year: 2011).*

(Continued)

*Primary Examiner* — Maher M Haddad
(74) *Attorney, Agent, or Firm* — Wenderoth, Lind & Ponack, L.L.P.

(57) ABSTRACT

The present invention provides a drug for preventing or treating inflammation-associated diseases in which a periostin isoform having cell adhesion activity is involved, and also provides an inhibitor of a periostin isoform having cell adhesion activity.

11 Claims, 13 Drawing Sheets
Specification includes a Sequence Listing.

(56) References Cited

OTHER PUBLICATIONS

Lv et al. Epithelial cell-derived periostin functions as a tumor suppressor in gastric cancer through stabilizing p53 and E-cadherin proteins via the Rb/E2F1/p14ARF/Mdm2 signaling pathway. Cell Cycle 13:18, 2962-2974; Sep. 15, 2014. (Year: 2014).*
Gordon et al. A protective role for periostin and TGF-b in IgE-mediated allergy and airway hyperresponsiveness. Clinical & Experimental Allergy, 42, 144-155, 20011 (Year: 2011).*
Nakama et al. Different roles played by periostin splice variants in retinal neovascularization. Experimental Eye Research 153 (2016) 133-140. (Year: 2016).*
Rousseau et al. A new sandwich elisa of mouse periostin for in-vitro and in-vivo animal studies. Journal of Bone and Mineral Research, (2011) vol. 26, Supp. Suppl. 1. Abstract No. MO0320. (Year: 2011).*
Tai et al. Periostin induction in tumor cell line explants and inhibition of in vitro cell growth by mor cell line explants and inhibition of in vitro cell growth by anti-periostin antibodies. Carcinogenesis vol. 26 No. 5 pp. 908-915, 2005 (Year: 2005).*
Tai et al. The Effect of Periostin on Tumor Growth in Colorectal Cancer . Digestive Disease Week Abstracts and Itinerary Planner, (2003) vol. 2003, pp. Abstract No. W985. (Year: 2003).*
Extended European Search Report dated Nov. 18, 2016 in corresponding European Application No. 14761201.4.
Zhu et al., "Immunolocalization of Periostin-like Factor and Periostin During Embryogenesis", Journal of Histochemistry and Cytochemistry, vol. 56, No. 4, 2007, pp. 329-345.
Rutishauser et al., "Amino Acid Sequence of the Fc Region of a Human γG Immunoglobulin", Proceedings of the National Academy of Sciences of the United States of America, vol. 61, 1968, pp. 1414-1421.
Hoersch et al., "Periostin shows increased evolutionary plasticity in its alternatively spliced region", BMC Evolutionary Biology, Biomed Central Ltd., London, GB, vol. 10, No. 1, 2010, p. 30, 19 pages.
Morishita et al., "Role of periostin in cancer progression and metastasis: Inhibition of breast cancer progression and metastasis by anti-periostin antibody in a murine model", International Journal of Molecular Medicine, vol. 28, 2011, pp. 181-186.
Takeshita et al., "Osteoblast-specific factor 2: cloning of a putative bone adhesion protein with homology with the insect protein fasciclin I", Biochem. J., vol. 294, 1993, pp. 271-278.
Horiuchi et al., "Identification and Characterization of a Novel Protein, Periostin, with Restricted Expression to Periosteum and Periodontal Ligament and Increased Expression by Transforming Growth Factor β", Journal of Bone and Mineral Research, vol. 14, No. 7, 1999, pp. 1239-1249.
Katsuragi et al., "Periostin as a Novel Factor Responsible for Ventricular Dilation", Circulation, Journal of the American Heart Association, vol. 110, 2004, pp. 1806-1813.
Wang et al., "Effects of Pressure Overload on Extracellular Matrix Expression in the Heart of the Atrial Natriuretic Peptide-Null Mouse", Hypertension, vol. 42, 2003, pp. 88-95.
Peters et al., "Molecular Anatomy of an Intracranial Aneurysm Coordinated Expression of Genes Involved in Wound Healing and Tissue Remodeling", Stroke, vol. 32, 2001, pp. 1036-1042.
Shao et al., "Acquired Expression of Periostin by Human Breast Cancers Promotes Tumor Angiogenesis through Up-Regulation of Vascular Endothelial Growth Factor Receptor 2 Expression", Molecular and Cellular Biology, vol. 24, No. 9, May 2004, pp. 3992-4003.
Gonzalez et al., "Identification of 9 Genes Differentially Expressed in Head and Neck Squamous Cell Carcinoma", Arch Otolaryngol Head Neck Surg, vol. 129, Jul. 2003, pp. 754-759.
Sasaki et al., "Elevated serum periostin levels in patients with bone metastases from breast but not lung cancer", Breast Cancer Research and Treatment, vol. 77, 2003, pp. 245-252.
Sasaki et al., "Novel chemiluminescence assay for serum periostin levels in women with preeclampsia and in normotensive pregnant women", Am J Obstet Gynecol, vol. 186, 2002, pp. 103-108.
Lindner et al., "Vascular Injury Induces Expression of Periostin: Implications for Vascular Cell Differentiation and Migration", Aterioscler Thromb Vasc Biol., vol. 25, 2005, pp. 77-83.
Litvin et al., "Expression and function of periostin-like factor in vascular smooth muscle cells", Am J Physiol Cell Physiol, vol. 292, 2007, pp. C1672-C1680.
Butcher et al., "Periostin promotes atrioventricular mesenchyme matrix invasion and remodeling mediated by integrin signaling through Rho/PI 3-kinase", Developmental Biology, vol. 302, 2007, pp. 256-266.
Li et al., "Phosphatidylinositol-3-kinase signaling mediates vascular smooth muscle cell expression of periostin in vivo and in vitro", Atherosclerosis, vol. 188, 2006, pp. 292-300.
Roy et al., "Transcriptome-wide analysis of blood vessels laser captured from human skin and chronic wound-edge tissue", PNAS, vol. 104, No. 36, Sep. 4, 2007, pp. 14472-14477.
Goetsch et al., "Transcriptional profiling and regulation of the extracellular matrix during muscle regeneration", Physiological Genomics, vol. 14, 2003, pp. 261-271.
Blanchard et al., "Periostin facilitates eosinophil tissue infiltration in allergic lung and esophageal responses", Mucosal Immunol., vol. 1, No. 4, Jul. 2008, pp. 289-296.
Stankovic et al., "Gene Expression Profiling of Nasal Polyps Associated With Chronic Sinusitis and Aspirin-Sensitive Asthma", The Laryngoscope, vol. 118, May 2008, pp. 881-889.
Woodruff et al., "Genome-wide profiling identifies epithelial cell genes associated with asthma and with treatment response to corticosteroids", PNAS, vol. 104, No. 40, Oct. 2, 2007, pp. 15858-15863.
Bao et al., "Periostin potently promotes metastatic growth of colon cancer by augmenting cell survival via the Akt/PKB pathway", Cancer Cell, vol. 5, Apr. 2004, pp. 329-339.
Abstract of Shao et al., "Human microvascular endothelial cells immortalized with human telomerase catalytic protein: a model for the study of in vitro angiogenesis", Biochem Biophys Res Commun., vol. 321, No. 4, Sep. 3, 2004, pp. 788-794.
Siriwardena et al., "Periostin is frequently overexpressed and enhances invasion and angiogenesis in oral cancer", British Journal of Cancer, vol. 95, 2006, pp. 1396-1403.
Abstract of Takanami et al., "Expression of periostin in patients with non-small cell lung cancer: correlation with angiogenesis and lymphangiogenesis", Int J Biol Markers, vol. 23, No. 3, Jul.-Sep. 2008, pp. 182-186.
Litvin et al., "Expression and Function of Periostin-Isoforms in Bone", Journal of Cellular Biochemistry, vol. 92, 2004, pp. 1044-1061.
Gillan et al., "Periostin Secreted by Epithelial Ovarian Carcinoma is a Ligand for $\alpha_v\beta_3$ and $\alpha_v\beta_5$ Integrins and Promotes Cell Motility", Cancer Research, vol. 62, Sep. 15, 2202, pp. 5358-5364.
Folkman, "The roll of angiogenesis in tumor growth", J. Semin Cancer Biol., vol. 3, No. 2, Apr. 1992, pp. 65-71.
Hanahan et al., "Patterns and Emerging Mechanisms of the Angiogenic Switch during Tumorigenesis", Cell, vol. 86, Aug. 9, 1996, pp. 353-364.
Liotta et al., "Cancer Metastasis and Angiogenesis: An Imbalance of Positive and Negative Regulation", Cell, vol. 64, Jan. 25, 1991, pp. 327-336.
Liotta et al., "Tumor cell autocrine motility factor", Proc. Natl, Acac. Sci., vol. 83, May 1986, pp. 3302-3306.
Erkan et al., "Periostin Creates a Tumor-Supportive Microenvironment in the Pancreas by Sustaining Fibrogenic Stellate Cell Activity", Gastroenterology, vol. 132, 2007, pp. 1447-1464.
Baril et al., "Periostin promotes invasiveness and resistance of pancreatic cancer cells to hypoxia-induced cell death: role of the β4 integrin and the PI3k pathway", Oncogene, vol. 26, 2007, pp. 2082-2094.
Grigoriadis et al., "Establishment of the epithelial-specific transcriptome of normal and malignant human breast cells based on MPSS and array expression data", Breast cancer Research, vol. 8, R56, 2006, pp. 1-15.
Kudo et al., "Periostin Promotes Invasion and Anchorage-Independent Growth in the Metastatic Process of Head and Neck Cancer", Cancer Res., vol. 66, No. 14, Jul. 15, 2006, pp. 6928-6935.

(56) References Cited

OTHER PUBLICATIONS

Contie et al., "Increased expression and serum levels of the stromal cell-secreted protein periostin in breast cancer bone metastases", International Journal of Cancer, vol. 128, 2010, pp. 352-360.
Sasaki et al., "Serum level of the periostin, a homologue of an insect cell adhesion molecule, in thymoma patients", Cancer Letters, vol. 172, 2001, pp. 37-42.
Sasaki et al., "Corrigendun to Serum level of the periostin, a homologue of an insect cell adhesion molecule, in thymoma patients" [Cancer Letters 172 (2001) 37-42], Cancer Letters, vol. 202, 2003, p. 117.
Sasaki et al., "Serum Level of the Periostin, a Homologue of an Insect Cell Adhesion Molecule, as a Prognostic Marker in Nonsmall Cell Lung Carcinomas", Cancer, vol. 92, 2001, pp. 843-848.
Sasaki et al., "Erratum", Cancer, vol. 92, 2001, pp. 843-848, 2580.
Zhu et al., "Periostin promotes ovarian cancer angiogenesis and metastasis", Gynecologic Oncology, vol. 119, 2010, pp. 337-344.
Tischler et al., "Periostin is up-regulated in high grade and high stage prostate cancer", BMC Cancer, vol. 10, No. 273, 2010, pp. 1-9.
Riener et al., "Expression of the extracellular matrix protein periostin in liver tumours and bile duct carcinomas", Histopathology, vol. 56, 2010, pp. 600-606.
Kwon et al., "Expression patterns of aurora kinase B, heat shock protein 47, and periostin in esophageal squamous cell carcinoma", Oncol Res., vol. 18, No. 4, 2009, pp. 141-151.
Tsunoda et al., "The Increased Expression of Periostin During Early Stages of Prostate Cancer and Advanced Stages of Cancer Stroma", The Prostate, vol. 69, 2009, pp. 1398-1403.
Puppin et al., "High periostin expression correlates with aggressiveness in papillary thyroid carcinomas", Journal of Endocrinology, vol. 197, 2008, pp. 401-408.
Thiery et al., "Breast cancer progression with a Twist", Nature Medicine, vol. 10, No. 8, Aug. 2004, pp. 777-778.
Yang et al., "Twist, a Master Regulator of Morphogenesis, Plays an Essential Role in Tumor Metastasis", Cell, vol. 117, Jun. 25, 2004, pp. 927-939.
Oshima et al., "A Novel Mechanism for the Regulation of Osteoblast Differentiation: Transcription of Periostin, a Member of the Fasciclin I Family, is Regulated by the bHLH Transcription Factor, Twist", Journal of Cellular Biochemistry, vol. 86, 2002, pp. 792-804.
Yan et al., "Transduction of a Mesenchyme-specific Gene Periostin into 293T Cells Induces Cell Invasive Activity through Epithelial-Mesenchymal Transformation", J. Biol. Chem, vol. 281, 2006, pp. 19700-19708.
Kim et al., "Periostin is down-regulated in high grade human bladder cancers and suppresses in vitro cell invasiveness and in vivo metastasis of cancer cells", Int. J. Cancer, vol. 117, 2005, pp. 51-58.
Kornowski et al., "In-Stent Restenosis: Contributions of Inflammatory Responses and Arterial Injury to Neointimal Hyperplasia", JACC, vol. 31, No. 1, Jan. 1998, pp. 224-230.
Hakuno et al., "Periostin advances atherosclerotic and rheumatic cardiac valve degeneration by inducing angiogenesis and MMP production in humans and rodents", J Chin Invest., vol. 120, No. 7, 2010, pp. 2292-2306.
Zhou et al., "Spatiotemporal expression of periostin during skin development and incisional wound healing: lessons for human fibrotic scar formation", J. Cell Commun. Signal, vol. 4, 2010, pp. 99-107.
Takagi et al., "Molecular Mechanism of Ischemia-Induced Retinal Neovascularization", Cell Technology, vol. 19, No. 8, 2000, pp. 1160-1165, 1142-1144, with partial English translation.

Brakenhielm et al., "Angiogenesis Inhibitor, TNP-470, Prevents Diet-Induced and Genetic Obesity in Mice", Circ Res., vol. 94, 2004, pp. 1579-1588.
Vagnucci et al., "Alzheimer's disease and angiogenesis", The Lancet, vol. 361, Feb. 15, 2003, pp. 605-608.
O'Reilly et al., "Angiostatin induces and sustains dormancy of human primary tumors in mice", Nature Medicine, vol. 2, No. 6, Jun. 1996, pp. 689-692.
Sim et al., "A Recombinant Human Angiostatin Protein Inhibits Experimental Primary and Metastatic Cancer", Cancer Research, vol. 57, 1997, pp. 1329-1334.
O'Reilly et al., "Endostatin: An Endogenous Inhibitor of Angiogenesis and Tumor Growth", Cell, vol. 88, Jan. 24, 1997, pp. 277-285.
Ingber et al., "Synthetic analogues of fumagillin that inhibit angiogenesis and suppress tumour growth", Nature, vol. 348, Dec. 6, 1990, pp. 555-557.
Oikawa et al., "Effects of Cytogenin, a Novel Microbial Product, on Embryonic and Tumor Cell-Induced Angiogenic Responses in Vivo", Anticancer Reaserach, vol. 17, 1997, pp. 1881-1886.
Abstract of Taraboletti et al., "Inhibition of angiogenesis and murine hemangioma growth by batimastat, a synthetic inhibitor of matrix metalloproteinases", J Natl Cancer Inst., vol. 87, No. 4, Feb. 15, 1995, pp. 293-298.
Abstract of "Marimastat: BB 2516, TA 2516",Drugs R D, vol. 4, No. 3, 2003, pp. 198-203.
Iqbal et al., "Integration of novel agents in the treatment of colorectal cancer", Cancer Chemother Pharmacol, vol. 54, Suppl. 1, 2004, pp. S32-S39.
Taniyama et al., "Periostin regulation and cardiovascular disease", vol. 43, No. 14, 2011, pp. 38(582)-44(588), with partial English translation.
Kim et al., "Periostin alternative splicing variants", Cancer Society, vol. 65, 2006, P-572, p. 302, with partial English translation.
Ishibashi et al., "Comprehensive Strategy for Retinal Neuroprotection—Challenging the Clinical Application", Neuroprotection, vol. 116, No. 3, 2012, pp. 165-199, with English abstract.
Tai et al., "Periostin induction in tumor cell line explants and inhibition of in vitro cell growth by anti-periostin antibodies", Carcinogenesis, vol. 26, No. 5, 2005, pp. 908-915.
International Preliminary Report on Patentability dated Sep. 11, 2015 in corresponding International (PCT) Application No. PCT/JP2014/055861.
International Search Report dated May 27, 2014 in International (PCT) Application No. PCT/JP2014/055861.
McCarvil et al., "Expression of meningococcal epitopes in LamB of *Escherichia coli* and the stimulation of serosubtype-specific antibody responses", Molecular Microbiology, 10(1), 1993, pp. 203-213.
L. Yang et al., "Periostin Facilitates Skin Sclerosis via P13K/Akt Dependent Mechanism in Mouse Model of Scleroderma", PLoS ONE, 2012, vol. 7, Issue 7, e41994, pp. 1-11.
A. Lorts et al., "Deletion of periostin reduces muscular dystrophy and fibrosis in mice by modulating the transforming growth factor-$\beta$ pathway", Proc. Natl. Acad. Sci. U.S.A., 2012, vol. 109, No. 27, p. 10978-10983.
Human Periostin/OSF-2 Antibody, R&D systems, [online], <URL:https://www.rndsystems.com/products/human-periostin-osf-2-antibody_af3548>, <URL:https://www.rndsystems.com/products/human-periostin-osf-2-antibody af3548#citations>, pp. 1-5.
Periostin/OSF-2 Antibody, Novus Biologicals, [online], <URL:https:///www.novusbio.com/products/periostin-osf-2-antibody_nbp1-30042>, <URL: https://www.novusbio.com/products/periostin-osf-2-antibody_nbp1-30042#reviews-publications>, pp. 1-6.

\* cited by examiner

A (1) FN
(2) PN2
(3) PN2 / rIgG
(4) PN2 / ex21PoAb
(5) control

B

Analysis method : Bonferroni/Dunn

A

B

A

B

A

B

A

B

ANTIBODY AGAINST PEPTIDE ENCODED BY EXON-21 OF PERIOSTIN AND PHARMACEUTICAL COMPOSITION FOR PREVENTING OR TREATING INFLAMMATION-ASSOCIATED DISEASES CONTAINING THE SAME

TECHNICAL FIELD

The present invention relates to an antibody against a peptide encoded by Exon-21 of periostin and a pharmaceutical composition for preventing or treating inflammation-associated diseases containing the same.

BACKGROUND ART

Periostin is an extracellular matrix protein consisting of a polypeptide of a molecular weight of about 90,000. The polypeptide chain contains a signal sequence, a cysteine-rich domain, a fourfold repeated domain, and a C-terminal domain.

Periostin was initially designated osteoblast-specific factor-2 (OSF-2) and was isolated and identified as a gene specifically expressed in the mouse osteoblast cell line MC3T3-E1 (Patent Literature 1, Non Patent Literature 1). The protein was later renamed periostin and was reported to have adhesion-promoting activity in osteoblast cells (Non Patent Literature 2).

In early studies, periostin was considered to be an extracellular matrix specifically expressed in bone tissue. However, it has been revealed that periostin is highly expressed not only in bone tissue but also at the onset of heart failure (Non Patent Literature 3, Non Patent Literature 4), aneurysm (Non Patent Literature 5), cancers (Non Patent Literature 6 to 8), preeclampsia (Non Patent Literature 9), vascular restenosis (Non Patent Literature 10 to 15), inflammatory diseases ((i) esophagitis (Non Patent Literature 16), (ii) sinusitis and asthma (Non Patent Literature 17), (iii) asthma (Non Patent Literature 18), (iv) angiogenesis (Non Patent Literature 6, Non Patent Literature 19 to 22)), etc. and that the protein is very slightly expressed in normal tissue. It has also been revealed that some periostin splice variants are expressed in osteoblasts (Non Patent Literature 1 and 2, Non Patent Literature 23, Patent Literature 2).

As to the functions of periostin, a periostin splice variant of 811 amino acids corresponding to PN-2 in FIG. 1) (Non Patent Literature 2) and a periostin splice variant of 783 amino acids (corresponding to PN-4 in FIG. 1) (Non Patent Literature 24) have been reported to have cell adhesion properties. In contrast, some periostin splice variants lack cell adhesion properties and they include a periostin splice variant of 838 amino acids (corresponding to PN-1 in FIG. 1) (Patent Literature 2) and a periostin splice variant of 810 amino acids (corresponding to PN-3 in FIG. 1) (Patent Literature 4).

As regards cancers, cancer metastasis is mediated by processes such as invasion of cancer cells from the primary tumor into blood vessels or lymph vessels, selective migration of cancer cells to metastatic organs, invasion of cancer cells from blood vessels into metastatic organs, growth of cancer cells supported by the microenvironment where metastasis occurred, and angiogenesis-associated growth of a tumor whose diameter exceeds several millimeters (Non Patent Literature 25 and 26). Among these complex processes for metastasis establishment, invasion and metastasis induced by the enhanced motility of cancer cells are very important stages (Non Patent Literature 27). Until now, it has been reported that highly metastatic cancer cells produce an autocrine motility factor by themselves to enhance their own motion (Non Patent Literature 28). Inhibitory substances against this malignant factor are expected as metastasis inhibitors, but no specific inhibitor has been found at present.

Various reports have been issued on high level expression of periostin in highly metastatic cancers (pancreatic cancer (Non Patent Literature 29), oral cancer (Non Patent Literature 21), pancreatic cancer (Non Patent Literature 30), breast cancer (Non Patent Literature 31), head and neck cancer (Non Patent Literature 32), colon cancer (Non Patent Literature 19), breast cancer (Non Patent Literature 6, 8 and 33), thymic cancer (Non Patent Literature 34 and 35), non-small cell lung cancer (Non Patent Literature 36 and 37), ovarian cancer (Non Patent Literature 38), prostate cancer (Non Patent Literature 39), liver cancer and bile duct cancer (Non Patent Literature 40), esophagus squamous cancer (Non Patent Literature 41), prostate cancer (Non Patent Literature 42), thyroid cancer (Non Patent Literature 43)). The high level expression of the transcription factor Twist in highly metastatic cancers has been reported (Non Patent Literature 44 and 45) and received attention. There has been a report showing that Twist is also located in the promoter region of periostin (Non Patent Literature 46). In addition, it has been reported that the invasion ability of the human embryonic kidney epithelial cell line 293T is enhanced when the periostin gene is introduced into the cell line (Non Patent Literature 47). It has also been reported that a periostin splice variant of 811 amino acids (corresponding to PN-2 in FIG. 1) was less expressed in various cancer cells, and introduction of the periostin gene into melanoma cells inhibited their metastasis to the lung (Non Patent Literature 48).

As regards vascular restenosis, a bare metal stent (BMS) has been widely used. Three to eight months after BMS implantation, in-stent restenosis (ISR) occurs in 10 to 40% of cases. The mechanism of ISR is considered to be principally neointimal hyperplasia associated with migration of smooth muscle cells from the tunica media of the coronary artery into the stent and subsequent proliferation of the cells (Non Patent Literature 49). To overcome the drawback, a drug-eluting stent (DES), which is a stent with the surface coated with a drug, was developed as a sirolimus-eluting stent (SES) by Sousa et al. in 1999. However, late stent thrombosis caused by DES has been reported, and accordingly a drug for safely inhibiting restenosis has been desired. Various papers have reported high level expression of periostin in vessel smooth muscle of an animal model with balloon injury-induced restenosis (Non Patent Literature 10 to 15).

As regards inflammations, antiinflammatory drugs have been clinically used and they include steroidal and non-steroidal antiinflammatory drugs for acute and chronic inflammatory diseases, and immunosuppressants and gold preparations for chronic progressive inflammatory diseases (for example, rheumatism, osteoarthritis, etc.). The main mechanism of action of non-steroidal antiinflammatory drugs is the inhibition of inflammatory mediators. The drugs provide symptomatic treatment and are effective for acute diseases, but less effective for chronic inflammatory diseases. Steroidal antiinflammatory drugs are highly effective for acute and chronic inflammatory diseases, but have been reported to concomitantly cause serious side effects. Accordingly, care should be taken when the drugs are used. Gold preparations are not applied to acute inflammation diseases, but are used for chronic rheumatism. Gold preparations have immunoregulatory activity and thus exert delayed effects. Gold preparations, however, also have been reported to cause side effects, including mucosal and cutaneous symptoms, myelosuppression, renal dysfunction and respiratory dysfunction. Accordingly, as with the case of steroidal antiinflammatory drugs, sufficient care should be taken when gold preparations are used. Some of immunosuppressants have also received attention in terms of clinical application to chronic rheumatism, but the side effects characteristic of immunosuppressants are of a concern.

Enhanced expression of periostin in inflammatory diseases has been reported (Non Patent Literature 16 to 18, 50 and 51).

Angiogenesis is closely associated with, in addition to cancers, aggravation of some diseases including diabetic retinopathy, atherosclerosis, periodontosis, scleroderma, glaucoma, age-related macular degeneration, and diabetes mellitus type II. Angiogenesis also plays pivotal roles in the onset and aggravation of rheumatoid arthritis, Kaposi sarcoma, psoriasis and Basedow disease (Non Patent Literature 52). It has been also shown that expansion of adipose tissue depends on angiogenesis, and the inhibition of angiogenesis has been reported to be effective for the prevention of obesity etc. (Non Patent Literature 53). In Alzheimer's disease, cerebral endothelial cells activated by angiogenesis secrete a precursor substrate for β-amyloid and a neurotoxic peptide that selectively kills cortical neurons, and hence the inhibition of angiogenesis has been reported to be effective for the prevention and treatment of Alzheimer's disease (Non Patent Literature 54). Based on these studies, angiogenesis inhibitors have been used to treat and prevent the above diseases in recent years, and there has been a demand for substances effective for inhibiting angiogenesis.

Angiogenesis inhibitors that have been found are angiostatin (Non Patent Literature 55 and 56); endostatin (Non Patent Literature 57); fumagillin derived from *Aspergillus fumigatus* and its synthetic derivative TNP-470 (Non Patent Literature 58); cytogenin (Non Patent Literature 59); synthetic chemical substances, such as metalloproteinase inhibitors, batimastat (BB-94) and marimastat (BB-2516) (Non Patent Literature 60 and 61); and monoclonal antibodies that inhibit the binding of angiogenesis factors (EGF, TGF-α, VEGF, etc.) to the corresponding receptors (Non Patent Literature 62). These substances, however, require careful consideration of the side effects, and the safety of the substances to a human body is not fully guaranteed.

Expression of periostin has been reported to be closely related to angiogenesis in the onset of cancers (Non Patent Literature 6, Non Patent Literature 19, Non Patent Literature 21 and 22). Induction of angiogenesis by periostin has been reported to be achieved through the expression of VEGF receptor-2 (Flk-1/KDR) in vascular endothelial cells (Non Patent Literature 20).

As described above, it has been indicated that periostin gene expression is related to vascular restenosis conditions, cancers, inflammations and angiogenesis conditions. Reports have also been made on an antibody relating to the inhibition of cell migration mediated by periostin (Non Patent Literature 12) and an antibody having inhibitory activity against periostin-induced cell growth (Non Patent Literature 13). However, the relation of the structure of a periostin splice variant to vascular restenosis, cancers, inflammations and angiogenesis still remains unclear.

CITATION LIST

Patent Literature

Patent Literature 1: JP 5-268982 A
Patent Literature 2: WO 2005/019471
Patent Literature 3: WO 2007/077934
Patent Literature 4: WO 02/020055

Non Patent Literature

Non Patent Literature 1: Takeshita S. et al., Biochem J (1993) 294, 271-278.
Non Patent Literature 2: Horiuchi K. et al., J. Bone Miner. Res. (1999) 14, 1239-1249.
Non Patent Literature 3: Katsuragi N. et al., Circulation (2004) 110, 1806-1813.
Non Patent Literature 4: Wang D. et al., Hypertension (2003) 42, 88-95.
Non Patent Literature 5: Peters D G. et al., Stroke (2001) 32, 1036-1042.
Non Patent Literature 6: Shao R. et al., Mol Cell Biol. (2004) 24(9), 3992-4003.
Non Patent Literature 7: Gonzalez H E. et al., Arch Otolaryngol Head Neck Surg. (2003) 129, 754-759.
Non Patent Literature 8: Sasaki H. et al., Breast Cancer Res Treat. (2003) 77(3), 245-252.
Non Patent Literature 9: Sasaki H. et al., Am J Obstet Gynecol. (2002) 186, 103-108.
Non Patent Literature 10: Lindner V. et al., Arterioscler Thromb Vasc Biol. (2005) 25, 77-83.
Non Patent Literature 11: Litvin J. et al., Am J Physiol Cell Physiol (2007) 292, C1672-C1680.
Non Patent Literature 12: Butcher J T. et al., Dev Biol. (2007) 302(1), 256-266.
Non Patent Literature 13: Li G. et al., Atherosclerosis (2006) 188(2), 292-300.
Non Patent Literature 14: Roy S. et al., Proc Natl Acad Sci USA. (2007) 104(36), 14472-14477.
Non Patent Literature 15: Goetsch S C. et al., Physiol Genomics (2003) 14(3), 261-271.
Non Patent Literature 16: Blanchard C, et al., Mucosal Immunol. (2008) 1(4), 289-296.
Non Patent Literature 17: Stankovic K M, et al., Laryngoscope (2008) 118(5), 881-889.
Non Patent Literature 18: Woodruff P G, et al., Proc Natl Acad Sci USA. (2007) 104(40), 15858-15863.
Non Patent Literature 19: Bao S. et al., Cancer Cell (2004) 5(4), 329-339.
Non Patent Literature 20: Shao R. et al., Biochem Biophys Res Commun. (2004) 321(4), 788-794.
Non Patent Literature 21: Siriwardena B S. et al., Br J Cancer. (2006) 95 (10), 1396-1403.
Non Patent Literature 22: Takanami I. et al., Int J Biol Markers (2008) 23(3), 182-186.
Non Patent Literature 23: Litvin J. et al., J Cell Biochem. (2004) 92, 1044-1061.
Non Patent Literature 24: Gillan L. et al., Cancer Res. (2002) 62, 5358-5364.
Non Patent Literature 25: Folkman J. Semin. Cancer Biol (1992) 3, 65-71.
Non Patent Literature 26: Hanahan D. et al., Cell (1996) 86, 353-364.
Non Patent Literature 27: Liotta L A. et al., Cell (1991) 64, 327-336.
Non Patent Literature 28: Liotta L A. et al., Proc. Natl. Acad. Sci. (1986) 83, 3302-3306.
Non Patent Literature 29: Erkan M. et al., Gastroenterology (2007) 132(4), 1447-1464.
Non Patent Literature 30: Baril P. et al., Oncogene (2007) 26(14), 2082-2094.
Non Patent Literature 31: Grigoriadis A. et al., Breast Cancer Res. (2006) 8 (5), R56.

Non Patent Literature 32: Kudo Y. et al., Cancer Res. (2006) 66(14), 6928-6935.

Non Patent Literature 33: Tie S, et al., Int J Cancer. (2010) 16.

Non Patent Literature 34: Sasaki H. et al., Cancer Lett. (2001) 72(1), 37-42.

Non Patent Literature 35: Erratum in: Cancer Lett. (2003) 202(1), 117.

Non Patent Literature 36: Sasaki H. et al., Cancer (2001) 92(4), 843-848.

Non Patent Literature 37: Erratum in: Cancer (2002) 95(12), 2580.

Non Patent Literature 38: Zhu M et al., Gynecol Oncol. (2010) 119(2): 337-344.

Non Patent Literature 39: Tischler V et al., BMC Cancer. (2010) 9; 10: 273.

Non Patent Literature 40: Riener M O et al., Histopathology. (2010) 56(5): 600-6.

Non Patent Literature 41: Kwon Y J et al., Oncol Res. (2009) 18(4): 141-151.

Non Patent Literature 42: Tsunoda T et al., Prostate. (2009) 15; 69(13): 1398-1403.

Non Patent Literature 43: Puppin C et al., Endocrinol. (2008) 197(2): 401-408.

Non Patent Literature 44: Thiery J P. et al., Nat Med. (2004) 10(8), 777-778.

Non Patent Literature 45: Yang J, et al., Cell (2004) 117 (7), 927-939.

Non Patent Literature 46: Oshima A. et al., J Cell Biochem. (2002) 86(4), 792-804.

Non Patent Literature 47: Yan W. et al., J Biol Chem. (2006) 281(28), 19700-19708.

Non Patent Literature 48: Kim C J. et al., Int J Cancer (2005) 117(1), 51-58.

Non Patent Literature 49: Kornowski R. et al., J Am Coll Cardiol (1998) 31, 224-230.

Non Patent Literature 50: Hakuno D et al., J Clin Invest. 2010; 120(7): 2292-306.

Non Patent Literature 51: Zhou H M. et al., J Cell Commun Signal. 2010 4(2): 99-107.

Non Patent Literature 52: Saibo Kogaku, Vol. 19, No. 8, 2000, Tanpakushitsu Kakusan Koso, Vol. 45, No. 6, 1182-1187.

Non Patent Literature 53: Brakenhielm E. et al., Circ Res. (2004) 94(12), 1579-1588.

Non Patent Literature 54: Vagnucci A H Jr. et al., Lancet (2003) 361(9357), 605-608.

Non Patent Literature 55: M. S. O'Reilly, et al., Nature Medicine, 1996, 2, 689-692.

Non Patent Literature 56: B. K. Sim, et al., Cancer Research., 1997, 57, 1329-1334.

Non Patent Literature 57: M. S. O'Reilly, et al., Cell, 1997, 88, 277-285.

Non Patent Literature 58: D. Ingber, et al., Nature, 1990, 348, 555-557.

Non Patent Literature 59: T. Oikawa, et al., Anticancer Research, 1997, 17, 1881-1886.

Non Patent Literature 60: G. Taraboletti, et al., Journal of National Cancer Institute., 1995, 87, 293-298.

Non Patent Literature 61: Marimastat: BB 2516, TA 2516., Drugs in R&D, 2003, 4(3), 198-203.

Non Patent Literature 62: S. Iqbal and H. J. Lenz, HYPERLINK "http://www.ingentaconnect.com/content/klu/280" ¥o "Cancer Chemotherapy and Pharmacology" Cancer Chemotherapy and Pharmacology, 2004, 54 Suppl. 1, S32-39.

SUMMARY OF INVENTION

Technical Problem

An object of the present invention is to provide an inhibitor of a periostin isoform having cell adhesion activity. Another object of the present invention is to provide a novel agent for preventing or treating vascular restenosis, cancers, inflammations, angiogenesis and arteriosclerosis, the agent having a mechanism different from that of existing agents and being capable of improving the quality of life and long-term prognosis. Further, another object of the present invention is to provide a therapeutic method, a diagnostic method and a diagnostic reagent for vascular restenosis, cancers, inflammations and angiogenesis.

Solution to Problem

The inventors forced periostin splice variants PN-2 and PN-4 to be expressed, purified the proteins, and coated a plate with each of the proteins to investigate the adhesion of fibroblasts to the plate. The adhesion of the fibroblasts varied with the types of the splice variants. Periostin splice variant PN-2 showed significantly stronger cell adhesion activity than the negative control albumin (BSA) and the uncoated group, whereas periostin splice variant PN-4 showed weaker cell adhesion activity than the uncoated group and merely had very weak cell adhesion activity compared with the negative control albumin (BSA) (FIG. 2). The difference in adhesion ability indicated that the Exon-21 region is involved in cell adhesion. Based on this, the inventors presumed that an anti-periostin Exon-21 polyclonal antibody produced by using the Exon-21 region as an antigen will inhibit the cell adhesion by PN-2.

Analysis of periostin splice variants highly expressed in vascular restenosis, cancers, inflammatory colitis or angiogenesis conditions revealed that the C-terminal domain from which the splice variants are derived consists of Exons 15 to 23, and that rats have the following variants (1) to (4) (see FIG. 1).

(1) a variant retaining all the exons (called PN-1; consisting of 838 amino acids of SEQ ID NO: 1; the cDNA sequence is shown in SEQ ID NO: 2)

(2) a variant lacking Exon-17 (called PN-2; consisting of 811 amino acids of SEQ ID NO: 3; 27 amino acids (Exon-17) of SEQ ID NO: 4 are deleted from PN-1; the cDNA sequence is shown in SEQ ID NO: 5)

(3) a variant lacking Exon-21 (called PN-3; consisting of 810 amino acids; the amino acids at positions 785 to 812 from the N-terminus (28 amino acids of SEQ ID NO: 6 (Exon-21)) are deleted from PN-1)

(4) a variant lacking Exon-17 and Exon-21 (called PN-4; consisting of 783 amino acids of SEQ ID NO: 7; 28 amino acids (Exon-21) of SEQ ID NO: 6 are deleted from PN-2; the cDNA sequence is shown in SEQ ID NO: 8)

In addition to the rat splice variants, mouse and human PN-2 and PN-4 were also found (mouse PN-2 (SEQ ID NO: 9 (amino acid sequence), SEQ ID NO: 10 (cDNA sequence)); mouse PN-4 (SEQ ID NO: 11 (amino acid sequence), SEQ ID NO: 12 (cDNA sequence)); human PN-2 (SEQ ID NO: 13 (amino acid sequence), SEQ ID NO: 14 (cDNA sequence)); human PN-4 (SEQ ID NO: 15 (amino acid sequence), SEQ ID NO: 16 (cDNA sequence))).

The inventors attempted to produce an antibody specifically recognizing the amino acid residues encoded by Exon- 21 as an inhibitor of the exon, which exon is the structural difference between PN-2 and PN-4 and exclusively found in PN-2.

In order to produce an antibody, the material used as an immunogen must be hydrophilic, and when part of a large polypeptide, such as a protein, is used to produce an antibody, the part to be used as an immunogen must be exposed on the surface of the protein and form an epitope. Thus, in order to examine the possibility of using the Exon-21 peptide chain as an antigen, an epitope search was initially performed using Accelrys software Mac Vector 7.2, which is widely used in the bioinformatics field. The exon region showed some "hydrophilicity", but it was suggested from the "surface probability" and "antigenicity" that the amino acid sequence of the Exon-21 region of SEQ ID NO: 6 (EVSKVTKFIEGGDGHLFEDEAIKRLLQG) is very unlikely to be exposed on the surface of the protein molecule and has no immunogenicity. It was therefore presumed that the exon region cannot be used as an immunogen to produce an antibody, and that it would be difficult to practically produce an antibody against the exon region.

However, based on the belief that the use of an antibody against the polypeptide region encoded by Exon-21 found in PN-2 would be optimal for the specific inhibition of the PN-2 protein functions, the inventors attempted to produce an antibody against the amino acid sequence encoded by Exon-21. The inventors synthesized a peptide consisting of 28 amino acids constituting the peptide encoded by the Exon-21 region, immunized rabbits with the peptide, and purified an IgG fraction from the serum, thereby succeeding in the production of an anti-rat Exon-21 peptide polyclonal antibody.

The inventors conducted an investigation to determine whether the anti-rat Exon-21 polyclonal antibody has inhibitory activity against the adhesion activity of periostin. Mouse PN-2 protein was coated on rat vascular smooth muscle cells that had been cultured to subconfluence, and monocyte-derived THP-1 cells were seeded thereon, resulting in the adhesion of the THP-1 cells. Separately, PN-2 protein was mixed with the antibody, and the mixture and THP-1 cells were seeded, resulting in the inhibition of the adhesion of the THP-1 cells. The overall results confirmed that the anti-rat Exon-21 polyclonal antibody has inhibitory activity against the adhesion activity of periostin. The anti-rat Exon-21 polyclonal antibody inhibits the adhesion of THP-1 cells, thereby inhibiting the differentiation of the cells into macrophages. Hence the antibody has an inhibitory function against macrophage invasion into organs. Macrophages are often associated with various inflammatory diseases, and the anti-rat Exon-21 polyclonal antibody, therefore, was shown to have anti-inflammatory activity (FIG. 3).

The inventors investigated the inhibitory effect on vascular intimal hyperplasia using an animal model. Injury was induced in the left carotid artery of SD rats with the use of a balloon catheter, and simultaneously the anti-rat Exon-21 polyclonal antibody was intravascularly administered. After a certain period of time, the blood vessels were harvested, fixed, and stained with HE. The area ratio of the intima to the media was calculated and the severity of intimal hyperplasia was examined. No significant difference was found in the area of the media, but a significant difference was observed in the intima/media ratio between the anti-rat Exon-21 polyclonal antibody administration group and the scratching-alone group. The results showed the inhibition of intimal hyperplasia (FIG. 4A).

Based on the report of the association of PN-2 protein with inflammations, the inventors investigated the effect on arteriosclerosis by the anti-rat Exon-21 polyclonal antibody (ex21PoAb) (the polyclonal antibody against the peptide encoded by Exon-21 of rat periostin). The investigation was performed using a model of ApoE knockout (KO) mice, which are generally considered to be an arteriosclerosis-prone model, loaded with a high-fat diet for three months. The anti-rat Exon-21 polyclonal antibody (ex21PoAb)-administered mice showed significant inhibition of arteriosclerosis in the thoracic aorta (the upper part of the aorta), as evaluated by Oil red O staining, compared with the rabbit control IgG antibody (rIgG)-administered mice. The results revealed the arteriosclerosis inhibitory effect of the anti-rat Exon-21 polyclonal antibody (FIG. 5).

The inventors investigated the anti-inflammatory effect of an anti-human Exon-21 monoclonal antibody (ex21MoAb) in a model with Crohn's disease, which is inflammatory colitis typifying inflammatory diseases. The anti-human Exon-21 monoclonal antibody (ex21MoAb) or a mouse control IgG antibody (mIgG) was administered to male C57B6 mice at 8 weeks of age, and 1.75% dextran sulfate sodium (DDS) was administered via drinking water. Two weeks later, the length of the large intestine was significantly well maintained in the anti-human Exon-21 monoclonal antibody (ex21MoAb) administration group as compared with the mouse control IgG antibody (mIgG) administration group (FIG. 6). The anti-human Exon-21 monoclonal antibody (ex21MoAb) showed anti-inflammatory activity in the mouse colitis model.

Based on the report of the association of PN-2 protein with angiogenesis, the inventors investigated the angiogenesis inhibitory effect of the anti-rat Exon-21 polyclonal antibody (ex21PoAb) and the anti-human Exon-21 monoclonal antibody (ex21MoAb) in an animal model. After confirmation of the expression of the PN-2 gene in a lower extremity ischemia mouse model, the anti-rat Exon-21 polyclonal antibody (ex21PoAb) was administered, as a result of which a significant inhibitory effect on angiogenesis was observed (FIG. 7B). Immunostaining of the blood vessels in the tissue with a CD31 antibody showed significant inhibition of angiogenesis in the anti-rat Exon-21 polyclonal antibody (ex21PoAb) administration group (FIG. 8). The anti-human Exon-21 monoclonal antibody (ex21MoAb) also showed an inhibitory effect on the lower extremity blood flow (FIG. 9). The angiogenesis inhibitory effect of the anti-Exon-21 antibodies suggested potential inhibitory effect of the anti-Exon-21 antibodies on pathological angiogenesis.

The inventors performed Matrigel assay using cultured cells. The supernatant of MDA-MB231 human breast cancer cells significantly increased angiogenesis in human endothelial cells, whereas addition of the anti-rat Exon-21 polyclonal antibody (ex21PoAb) or the anti-human Exon-21 monoclonal antibody (ex21MoAb) significantly inhibited angiogenesis (FIGS. 10A and 10B). It was also shown that PN-2 induced angiogenesis in a dose-dependent manner (FIGS. 11A and 11B). The results showed that the anti-Exon-21 antibodies inhibit angiogenesis induced by a cancer.

The inventors investigated the effect of the anti-rat Exon-21 polyclonal antibody (ex21PoAb) on the proliferative capacity of cultured mouse 4T1 breast cancer cells, and as a result, significant cytostatic activity was observed by MTS assay, as compared with the administration of a rabbit control IgG antibody (rIgG) (FIG. 12A). The inventors also investigated the effect of the anti-human Exon-21 monoclonal antibody (ex21MoAb) on the necrosis of mouse 4T1 breast cancer cells, and as a result, significant necrosis induction activity was observed by the measurement of LDH in the supernatant, as compared with the administration of a mouse control IgG antibody (mIgG). The results confirmed the direct proliferation inhibitory effect and direct necrosis induction effect of the anti-Exon-21 antibodies on mouse 4T1 breast cancer cells (FIG. 12B).

Mouse 4T1 breast cancer cells were injected into the foot pad of mice to establish lung metastasis model mice, and then the anti-rat Exon-21 polyclonal antibody (ex21PoAb) was administered to the model mice once a week. Three to five weeks after the establishment of the model, significant inhibition of primary tumor growth as well as of the number of lung metastatic colonies from the primary tumors was observed, as compared with a rabbit control IgG antibody (rIgG) administration group (FIGS. 13A and 13B). The anti-human Exon-21 monoclonal antibody (ex21MoAb) was administered in the same manner as above, and as a result, significant inhibition of lung metastasis was observed as compared with a mouse control IgG antibody (mIgG) administration group (FIG. 14).

B16F10 mouse melanoma cells were injected into the footpad of mice to establish lung metastasis model mice, and then the anti-rat Exon-21 polyclonal antibody (ex21PoAb) was administered to the model mice once a week. Three weeks after the establishment of the model, significant inhibition of primary tumor growth as well as of the number of lung metastatic colonies from the primary tumors was observed, as compared with a rabbit control IgG antibody (rIgG) administration group (FIGS. 15A and 15B). The neutralizing antibodies against PN-2 (the anti-Exon-21 antibodies) were assumed to inhibit the PN-2 functions, such as the promoting effect for the adhesion of macrophages and the angiogenic effect, and thereby to inhibit the growth and lung metastasis of breast cancer cells or melanoma cells. This assumption suggested the potential of the neutralizing antibodies as novel therapeutic agents. The experimental results revealed that the anti-Exon-21 antibodies have inhibitory activity on primary tumor growth, which proceeds along with the progression of the cancer conditions, and also have inhibitory activity on lung metastasis from the primary tumors.

The inventors investigated the effect of the anti-human Exon-21 monoclonal antibody (ex21MoAb) on arteriosclerosis. The anti-human Exon-21 monoclonal antibody (ex21MoAb) was administered to an aneurysm mouse model once a week, and as a result, significant inhibition of the expansion of the diameter of the aorta was observed as measured with an ultrasound scanner, as compared with a mouse control IgG antibody (mIgG) administration group. The results revealed the aneurysm inhibitory effect of the anti-human Exon-21 monoclonal antibody (ex21MoAb) (FIG. 16). Thus the inventors completed the present invention.

The present invention solves the above problems. The present invention provides an antibody against a periostin isoform having cell adhesion activity that is specifically expressed in various inflammation-associated conditions including cancers. In particular, the present invention provides a composition for treating various inflammation-associated diseases including cancers, the composition comprising an antibody that recognizes the splice site of the periostin isoform as an antigen.

That is, the present invention includes the following.

(1) An antibody binding to one or more peptides selected from the group consisting of a peptide consisting of an amino acid sequence of SEQ ID NO: 6, a peptide consisting of an amino acid sequence of SEQ ID NO: 17 and a peptide consisting of an amino acid sequence of SEQ ID NO: 18.

(2) An antibody specifically binding to one or more peptides selected from the group consisting of a peptide consisting of an amino acid sequence of SEQ ID NO: 19, a peptide consisting of an amino acid sequence of SEQ ID NO: 20, a peptide consisting of an amino acid sequence of SEQ ID NO: 21 and a peptide consisting of an amino acid sequence of SEQ ID NO: 22.

(3) The antibody according to the above (1) or (2), which specifically recognizes a cell adhesion activity-related region of a periostin isoform having cell adhesion activity and neutralizes the cell adhesion activity of the periostin isoform.

(4) The antibody according to any one of the above (1) to (3), which is a polyclonal antibody, a monoclonal antibody, a chimeric antibody, a humanized antibody or a human antibody.

(5) The antibody according to the above (4), which is a monoclonal antibody.

(6) The antibody according to the above (5), which is produced by a hybridoma cell line designated as NITE BP-01546.

(7) An antibody fragment consisting of a partial fragment of the monoclonal antibody according to the above (5) or (6).

(8) An antibody derivative comprising a protein or low molecular weight drug linked to the antibody according to any one of the above (1) to (6) or the antibody fragment according to the above (7).

(9) A hybridoma producing the antibody according to any one of the above (1) to (5).

(10) A hybridoma cell line designated as NITE BP-01546.

(11) A method for producing the antibody according to the above (4), the method comprising
immunizing a non-human mammal with a peptide consisting of an amino acid sequence selected from the group consisting of an amino acid sequence of SEQ ID NO: 6, an amino acid sequence of SEQ ID NO: 17 and an amino acid sequence of SEQ ID NO: 18, or the peptide having a Cys residue added to the N-terminus,
fusing an antibody-producing cell of the animal with a myeloma cell to form a hybridoma, and
culturing the hybridoma.

(12) The production method according to the above (11), wherein the hybridoma is a hybridoma cell line designated as NITE BP-01546.

(13) A pharmaceutical composition for inhibiting a periostin isoform having cell adhesion activity, the composition comprising the antibody according to any one of the above (1) to (6), the antibody fragment according to the above (7) or the antibody derivative according to the above (8).

(14) A pharmaceutical composition for preventing or treating an inflammation-associated disease in which a periostin isoform having cell adhesion activity is involved, the composition comprising the antibody according to any one of the above (1) to (6), the antibody fragment according to the above (7) or the antibody derivative according to the above (8).

(15) A pharmaceutical composition for inhibiting vascular intimal hyperplasia in which a periostin isoform having cell adhesion activity is involved, treating a cancer in which a periostin isoform having cell adhesion activity is involved, inhibiting angiogenesis in which a periostin isoform having cell adhesion activity is involved, or preventing or treating aneurysm in which a periostin isoform having cell adhesion activity is involved, the composition comprising the antibody according to any one of the above (1) to (6), the antibody fragment according to the above (7) or the antibody derivative according to the above (8).

(16) A method for detecting or quantifying a periostin isoform having cell adhesion activity in a biological sample by using the antibody according to any one of the above (1) to (6), the antibody fragment according to the above (7) or the antibody derivative according to the above (8).

The term "an amino acid sequence of SEQ ID NO: XX" herein includes an amino acid sequence of SEQ ID NO: XX having deletion, substitution or addition of one to several amino acids. The term "several" means usually 2 to 8, preferably 2 to 5, more preferably 2 to 3.

Advantageous Effects of Invention

An inhibitor of a periostin isoform having cell adhesion activity, the inhibitor comprising the antibody of the present invention, is used to inhibit a particular periostin variant highly expressed in vascular intimal hyperplasia, cancers, inflammations including inflammatory colitis, diseases accompanied by angiogenesis, or the like, thereby inhibiting the exacerbation of the conditions of the diseases and treating the diseases. The antibody can also be used for the measurement of the amount of such a periostin variant in a patient sample to determine the presence or absence of a disease and the progression of the disease conditions.

DESCRIPTION OF EMBODIMENTS

Figure 1:
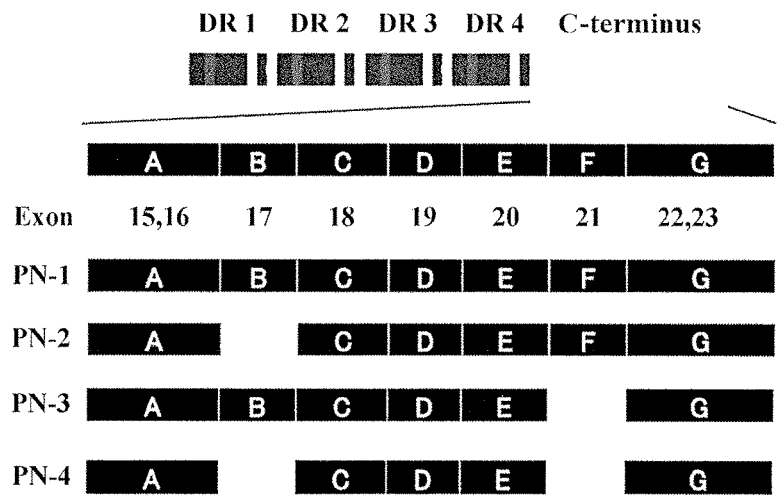
FIG. 1 is a schematic view showing mouse periostin splice variants.

An embodiment of the present invention provides an antibody against a periostin isoform having cell adhesion activity. Periostin is one of extracellular matrix proteins and several splice variants of periostin are known. Some of periostin splice variants are specifically expressed in cancer conditions etc. In general, antibodies are highly specific, are safe for humans and have other advantages, and therefore, in the present invention, an antibody can be used as a substance for inhibition (i.e., an inhibitory drug) against the functions of periostin splicing variants specifically expressed in cancer conditions etc. In the present invention, an antibody can be produced using, as an antigen, a chemically synthesized peptide consisting of the amino acid sequence encoded by Exon-21 in the C-terminal domain from which splice variants specific to cancer conditions and the like are derived. However, such a peptide can also be produced by enzymatic digestion of periostin proteins or by genetic engineering techniques, and the origin is not particularly limited.

The term "having cell adhesion activity" herein means the possession of cell adhesion-promoting activity. An investigation to determine whether a protein has cell adhesion activity can be performed as follows. A 10 μg/mL sample is placed in a petri dish to allow a protein to adhere to the surface overnight. Cultured cells such as cardiac fibroblasts are then added to the dish. Three to six hours later, the dish is washed and detached cells are removed. The remaining cells are dyed. The state of the remaining adherent cells is examined.

In the present invention, the periostin isoform having cell adhesion activity is not particularly limited, but preferred are a periostin isoform consisting of an amino acid sequence of SEQ ID NO: 3 (rat periostin PN-2, 811 amino acids), a periostin isoform consisting of an amino acid sequence of SEQ ID NO: 9 (mouse periostin PN-2, 811 amino acids), a periostin isoform consisting of an amino acid sequence of SEQ ID NO: 13 (human periostin PN-2, 809 amino acids), which is easily predicted to have adhesion activity since the amino acid sequence of human periostin is almost identical to those of mouse and rat periostins, a periostin splice variant having the amino acids constituting the peptide encoding Exon-21 but lacking the amino acids constituting the peptide encoding Exon-17, etc.

Periostin isoforms having cell adhesion activity include periostin isoforms having an amino acid sequence of SEQ ID NO: 6 (28 amino acids encoded by Exon-21 of rat periostin), SEQ ID NO: 17 (28 amino acids encoded by Exon-21 of mouse periostin) or SEQ ID NO: 18 (28 amino acids encoded by Exon-21 of human periostin).

Periostin isoforms that can serve as an epitope for an antibody include a periostin isoform having an amino acid sequence of SEQ ID NO: 19 (6 amino acids at positions 2 to 7 from the N-terminus of the amino acid sequence encoded by Exon-21 of human periostin (SEQ ID NO: 18)), a periostin isoform having an amino acid sequence of SEQ ID NO: 20 (7 amino acids at positions 17 to 23 from the N-terminus of the amino acid sequence encoded by Exon-21 of human periostin (SEQ ID NO: 18)), a periostin isoform having an amino acid sequence of SEQ ID NO: 21 (5 amino acids at positions 3 to 7 from the N-terminus of the amino acid sequence encoded by Exon-21 of human periostin (SEQ ID NO: 18)), a periostin isoform having an 8-amino acid sequence of SEQ ID NO: 22 consisting of 2 amino acids at positions 27 and 28 from the N-terminus of the amino acid sequence encoded by Exon-21 of human periostin (SEQ ID NO: 18) and the subsequent 6 amino acids, etc.

The regions responsible for the cell adhesion activity of periostin include, for example, Exon-21. Specific examples of the regions include the amino acid residues of SEQ ID NO: 6 representing a portion of a periostin isoform having an amino acid sequence of SEQ ID NO: 3 (the amino acids at positions 758 to 785 of SEQ ID NO: 3), the amino acid residues of SEQ ID NO: 17 representing a portion of a periostin isoform having an amino acid sequence of SEQ ID NO: 9 (the amino acids at positions 758 to 785 of SEQ ID NO: 9), the amino acid residues of SEQ ID NO: 18 representing a portion of a periostin isoform having an amino acid sequence of SEQ ID NO: 13 (the amino acids at positions 756 to 783 of SEQ ID NO: 13), etc.

In a preferred embodiment of the present invention, the phrase "specifically recognizes a site involved in cell adhesion" means to specifically recognize preferably a cell adhesion-related region of a periostin isoform containing Exon-21. Preferred antibodies that specifically recognize a site involved in the cell adhesion activity of a periostin isoform include, for example, antibodies against the amino acid residues of SEQ ID NO: 6 representing a portion of a periostin isoform having an amino acid sequence of SEQ ID NO: 3 (the amino acids at positions 758 to 785 of SEQ ID NO: 3), the amino acid residues of SEQ ID NO: 17 representing a portion of a periostin isoform having an amino acid sequence of SEQ ID NO: 9 (the amino acids at positions 758 to 785 of SEQ ID NO: 9), the amino acid residues of SEQ ID NO: 18 representing a portion of a periostin isoform having an amino acid sequence of SEQ ID NO: 13 (the amino acids at positions 756 to 783 of SEQ ID NO: 13), or part of any of the amino acid residues. Further examples of the antibodies include antibodies against a polypeptide having an amino acid sequence of SEQ ID NO: 19 or 20, an amino acid sequence of SEQ ID NO: 21 or 22, or part of the amino acid sequences.

The phrase "inhibits a region involved in the cell adhesion activity of periostin" means inhibition of the effect or activity of the above-described "region involved in the cell adhesion activity of periostin". In particular, for example, the phrase means inhibition of the effect or activity of periostin using the above-described antibody that specifically recognizes a site involved in the cell adhesion activity.

In an embodiment, the antibody of the present invention includes a monoclonal antibody and a polyclonal antibody produced by using any of the antigens as described above. The term "monoclonal antibody" herein refers to any monoclonal antibody reactive against any of the antigens as described above. The "monoclonal antibody" include natural antibodies produced by immunizing mammals such as mice, rats, hamsters, guinea pigs and rabbits with any of the antigens; antibodies that can be produced by using genetic recombination techniques, such as chimeric monoclonal antibodies (chimeric antibodies) and humanized monoclonal antibodies (humanized antibodies, i.e., CDR-grafted antibodies); and human monoclonal antibodies (human antibodies) that can be produced by using human antibody-producing transgenic animals or the like. The antibody of the present invention include monoclonal antibodies of any isotype, such as IgG (IgG1, IgG2, IgG3, IgG4), IgM, IgA, IgD and IgE. The antibody of the present invention is preferably IgG (IgG1, IgG2, IgG3, IgG4) or IgM.

When any of the peptides described above is to be used as an antigen, the peptide can be used alone as an antigen. Alternatively, to increase its antigenicity, the peptide can be adsorbed to a macromolecular material such as polyvinyl pyrrolidone, latex and polymethyl methacrylate and used for immunization, or can be conjugated to a carrier protein such as KLH (keyhole limpet hemocyanin) and BSA (bovine serum albumin), and any method can be used to increase the antigenicity. Generally, the peptide is preferably conjugated to a carrier protein by known methods (e.g., see "Zoku Iyakuhin no Kaihatsu, vol. 14, Hirokawa-Shoten Ltd., 1991").

For directional conjugation of the peptide to a carrier protein, a cysteine residue is added to the C- or N-terminus of the peptide, and via the cysteine residue, the peptide is conjugated to the carrier protein. As long as conjugation suitable for this purpose is achieved, any crosslinker commonly used in the art can be used. Suitable crosslinkers include succinimidyl-4-(N-maleimidomethyl)cyclohexane-1-carboxylate (hereinafter abbreviated to "SMCC"), 3-maleimidobenzoic acid-N-hydroxysuccinimide ester (MBS), etc. The monoclonal antibody is produced by generating a hybridoma by the cell fusion method of Kohler and Milstein (G. Kohler et al Nature (1975) 256, 495-7), culturing the hybridoma to allow the hybridoma to secrete an antibody, and isolating the antibody from the culture. In particular, a mammal is immunized with a peptide having an amino acid sequence encoded by Exon-21 or the like and then the antibody-producing cells of the animal are fused to myeloma cells to generate a hybridoma. Screening for a hybridoma producing an antibody binding to Exon-21 is performed by, e.g., enzyme-linked immunosorbent assay (hereinafter abbreviated to "ELISA") on the hybridoma supernatant using a microplate on which the antigen has been immobilized.

The animal to be immunized is not particularly limited, and include various mammals such as mice, rats, guinea pigs, rabbits, sheep, goats, cats, dogs, etc. Of the listed animals for immunization, Balb/c mice are generally used for production of monoclonal antibodies because of ease of handling or other advantages, but other strains of mice can also be used. The concentration of the antigen used for immunization is determined so that a sufficient amount of antigenically stimulated lymphocytes are produced. Preferably, 1 to 100 µg of the antigen is diluted to an appropriate concentration in physiological saline or the like, suspended in Freund's complete adjuvant or Freund's incomplete adjuvant or the like, and administered to an animal by intraperitoneal or subcutaneous injection or other means. The administration is performed once to several times at intervals of 2 to 4 weeks. The final immunization is normally performed by administering a solution of 1 to 100 µg of the antigen in physiological saline by intravenous or subcutaneous injection or other means. Several days after the final immunization, antibody-producing cells such as lymphocytes, preferably spleen cells or lymph node cells, are harvested from the immunized animal for cell fusion.

Cell fusion using spleen cells as antibody-producing cells will be explained below, but antibody-producing cells other than spleen cells can also be used for cell fusion. Spleen cells prepared from the spleen aseptically removed 3 to 4 days after the final immunization are fused to appropriate myeloma cells in the presence of a fusion promoter. The myeloma cells used for fusion may be any myeloma cells as long as they are derived from mammals, but generally preferred are those derived from the same species as the animal used for immunization. Various cell lines are already known. For example, preferred cell lines used for mice are SP2/0-Ag14 (SP2) [Nature, 276, 269 (1978)], NS-1-Ag4/1 (NS-1), P3-X63Ag8U.1 (P3U1) [Curr. Top. Microbiol. Immunol. 81, 1-7 (1978), available from ATCC under ATCC No. CRL-1597], P3-NS1-1-Ag4-1, P3-X63Ag8 (P3), FO, X63Ag8.653 (X63.653), 210.RCY3.Ag1.2.3, S194/5XXO.BU1, SKO-007, GM15006TG-A12, etc. Preferred cell lines used for rats are Y3.Ag1.2.3 etc. Preferred fusion promoters include polyethylene glycol (PEG) having a molecular weight of 1,000 to 6,000 and Sendai virus. Generally, the ratio of spleen cells and myeloma cells for cell fusion is preferably 10:1 to 2:1.

Hybridomas can be separated from fused cells by culturing a mixture of unfused spleen cells, unfused myeloma cells and fused cells in a selective medium that inhibits the survival of unfused myeloma cells for an appropriate period of time until unfused cells die (about 1 week). The selective medium may be, for example, HAT medium (a medium containing hypoxanthine, aminopterin and thymidine). In this selective medium, unfused myeloma cells die, and non-tumorous cells, i.e., unfused spleen cells die after a certain period of time (after about 1 week), as a result of which hybridomas are selected as viable cells. The hybridomas can be subjected to conventional limiting dilution for screening to select a strain producing the desired antibody and for cloning of the strain. Thus obtained hybridoma producing a monoclonal antibody of the present invention can be grown in medium suitable for the growth and can be easily stored in a deep freezer or liquid nitrogen for a long period of time.

The thus obtained hybridoma can be grown in nutrient medium or in the abdominal cavity of a mammal for antibody production. The produced antibodies can be purified from the culture supernatant or the ascites or serum of the mammal.

As a hybridoma of the present invention, a hybridoma that was internationally deposited with Incorporated Administrative Agency, National Institute of Technology and Evaluation, Patent Microorganisms Depositary (NPMD) (Deposit date: Feb. 26, 2013, Accession No.: NITE BP-01546, Identification Reference: KS-0259#8, 080611 Kohjin Bio) can be used.

Purification of the antibodies can be performed by conventional isolation/purification methods such as centrifugation, dialysis, salting out with ammonium sulfate or the like, ion exchange chromatography using a DEAF column or the like, gel filtration, affinity chromatography, etc.

The isotype and subclass determination of the thus obtained monoclonal antibody can be performed by an identification method such as the Ouchterlony method, ELISA and RIA. The Ouchterlony method is convenient but requires the condensation of the monoclonal antibody when the concentration is low. When ELISA or RIA is used, the isotype and subclass of the monoclonal antibody can be identified by direct reaction of the culture supernatant with an antigen-adsorbed solid phase, followed by reaction with antibodies against different immunoglobulin isotypes and subclasses as secondary antibodies. More conveniently, commercially available identification kits (e.g., Mouse Typer Kit (Bio-Rad)) or the like can be used. Protein quantification can be performed by the Folin-Lowry method or by calculation from the absorbance at 280 nm [1.4 (OD 280)=1 mg/mL immunoglobulin].

The thus obtained monoclonal antibody of the present invention specifically recognizes a periostin isoform having an amino acid sequence of SEQ ID NO: 3, SEQ ID NO: 9 or SEQ ID NO: 13 (PN-2); a periostin isoform having an amino acid sequence of SEQ ID NO: 6, SEQ ID NO: 17 or SEQ ID NO: 18; a periostin isoform having an amino acid sequence of SEQ ID NO: 19 or 20; a peptide consisting of an amino acid sequence of SEQ ID NO: 6, SEQ ID NO: 17 or SEQ ID NO: 18; or a peptide having an amino acid sequence of SEQ ID NO: 19 or 20. Preferably, the monoclonal antibody of the present invention specifically recognizes and binds to a peptide (SEQ ID NO: 19) consisting of the amino acid residues from valine (V) at position 2 to lysine (K) at position 7 from the N-terminus of the amino acid sequence of the human periostin Exon-21 peptide chain (SEQ ID NO: 18), and a peptide (SEQ ID NO: 20) consisting of the amino acid residues from phenylalanine (F) at position 17 to lysine (K) at position 23 from the N-terminus of the amino acid sequence of the human periostin Exon-21 peptide chain (SEQ ID NO: 18). That is, the monoclonal antibody of the present invention specifically recognizes the amino acid sequence VTKVTK (SEQ ID NO: 19) consisting of the amino acid residues from valine at position 2 to lysine at position 7 from the N-terminus of the amino acid sequence of the human periostin Exon-21 peptide chain (SEQ ID NO: 18), the amino acid sequence FEDEEIK (SEQ ID NO: 20) consisting of the amino acid residues from phenylalanine (F) at position 17 to lysine (K) at position 23 from the N-terminus of the amino acid sequence of the human periostin Exon-21 peptide chain (SEQ ID NO: 18), or part of the amino acid sequences.

The monoclonal antibody of the present invention inhibits or prevents the cell adhesion properties of human periostin-1 protein, i.e., the monoclonal antibody has the activity to neutralize the cell adhesion properties of human periostin-1 protein. The monoclonal antibody of the present invention also inhibits invasion, inflammations and angiogenesis in cancer conditions or the like, and prevents or treats inflammation-associated diseases.

When a polyclonal antibody is used as the antibody of the present invention, the polyclonal antibody can be produced by conventional methods such as the method described in "Shin Seikagaku Jikken Koza, vol. 12, edited by the Japanese Biochemical Society, Tokyo Kagaku Dozin Co. Ltd., 1992".

The animal to be immunized is not particularly limited, and include horses, goats, sheep, rabbits, guinea pigs, mice, chickens, etc. When a rabbit is to be immunized, an antigen is diluted to an appropriate concentration in physiological saline or the like and suspended in Freund's complete adjuvant, Freund's incomplete adjuvant, aluminum hydroxide adjuvant, or the like, and injected at a dose of 10 to 1,000 µg/animal per injection, followed by 1 to 3 booster injections 2 to 4 weeks after the immunization to give antisera. Multi-site subcutaneous injection is preferred. Preparation of polyclonal antibodies from antisera can be performed in the same manner as described for the purification of the monoclonal antibody.

The thus obtained polyclonal antibody of the present invention specifically recognizes a periostin isoform having an amino acid sequence of SEQ ID NO: 3, SEQ ID NO: 9 or SEQ ID NO: 13 (PN-2); a periostin isoform having an amino acid sequence of SEQ ID NO: 6, SEQ ID NO: 17 or SEQ ID NO: 18; a periostin isoform having an amino acid sequence of SEQ ID NO: 19 or 20; a peptide consisting of an amino acid sequence of SEQ ID NO: 6, SEQ ID NO: 17 or SEQ ID NO: 18; or a peptide having an amino acid sequence of SEQ ID NO: 19 or 20. Preferably, the polyclonal antibody of the present invention specifically recognizes and binds to a peptide (SEQ ID NO: 19) consisting of the amino acid residues from lysine (K) at position 7 to glycine (G) at position 11 from the N-terminus of the amino acid sequence of the human periostin Exon-21 peptide chain (SEQ ID NO: 18), and a peptide (SEQ ID NO: 20) consisting of the amino acid residues from lysine (K) at position 23 to leucine (L) at position 26 from the N-terminus of the amino acid sequence of the human periostin Exon-21 peptide chain (SEQ ID NO: 18). The polyclonal antibody of the present invention specifically recognizes the amino acid sequence TKVTK (SEQ ID NO: 21) consisting of the amino acid residues from position 3 to position 7 from the N-terminus of the amino acid sequence of the human periostin Exon-21 peptide chain (SEQ ID NO: 18), the amino acid sequence QGDTPVRK (SEQ ID NO: 22) consisting of the amino acid residues at positions 27 and 28 from the N-terminus of the amino acid sequence of the human periostin Exon-21 peptide chain (SEQ ID NO: 18) and the subsequent 6 amino acids, or part of the amino acid sequences.

The polyclonal antibody of the present invention inhibits or prevents the cell adhesion properties of human periostin-1 protein, i.e., the polyclonal antibody has the activity to neutralize the cell adhesion properties of human periostin-1 protein. The polyclonal antibody of the present invention also inhibits invasion, inflammations and angiogenesis in cancer conditions or the like, and prevents or treats inflammation-associated diseases.

The present invention also provides a composition for inhibiting vascular intimal hyperplasia, treating a cancer or inhibiting angiogenesis, the composition comprising an anti-periostin antibody that recognizes a periostin splice variant having cell adhesion properties.

Production of Humanized Antibodies

Immunoglobulin G (hereinafter simply referred to as "IgG") consists of two light polypeptide chains having a molecular weight of about 23,000 (hereinafter referred to as "light chains") and two heavy polypeptide chains having a molecular weight of about 50,000 (hereinafter referred to as "heavy chains"). The heavy and light chains both have repeating units of a conserved amino acid sequence of about 110 residues, and these units are the basic elements of the three-dimensional structure of IgG (hereinafter referred to as "domains"). The heavy and light chains consist of 4 and 2 successive domains, respectively. The amino terminal domains of the heavy and light chains are more variable in amino acid sequence between antibody molecules than other domains, and thus the amino terminal domains are called the variable domains (hereinafter referred to as "V domains"). At each amino terminal domain of IgG, the heavy chain V domain and the light chain V domain complementarily associate to form a variable region. The remaining domains collectively form a constant region. The sequence of the constant region is divergent between animal species. For example, the constant region of mouse IgG differs from the constant region of human IgG, and hence mouse IgG is recognized as a foreign body by the human immune system, resulting in a Human Anti-Mouse Antibody (hereinafter referred to as "HAMA") response (Schroff R W. et al. Cancer Res. (1985) 45, 879-85). Mouse antibodies thus cannot be repeatedly administered to humans. In order to administer such antibodies to humans, the antibody molecules must be modified to prevent a HAMA response while maintaining the specificity of the antibodies.

According to the results of X-ray crystal structural analysis, domains are generally in the form of a long cylindrical structure made up of a stack of two antiparallel beta sheets consisting of 3 to 5 beta chains. In terms of the variable region, three loops are assembled to form an antigen-binding site in each of the V domains of the heavy and light chains. These loops are called complementarity determining regions (hereinafter referred to as "CDRs"), which are most variable in amino acid sequence. The remaining parts of the variable region other than the CDRs serve to maintain the structures of the CDRs and are called "framework". Kabatt et al. collected a large number of the primary sequences of heavy and light chain variable regions, and provided a table in which the primary sequences are classified into CDRs and frameworks on the basis of sequence conservation (Kabatt et al. SEQUENCES OF IMMUNOLOGICAL INTEREST, 5th edition, NIH publication, No. 91-3242, E.A.).

The frameworks were further classified into a plurality of subgroups based on shared amino acid sequence patterns. The existence of consensus framework between human and mouse was also found. Such studies on the structural features of IgG led to the development of the methods for producing humanized antibodies described below. At an early stage of the studies, chimeric antibodies having a variable region from a mouse antibody fused to a constant region from a human antibody were proposed (Morrison S L. et al Proc Natl Acad Sci USA. (1984) 81, 6851-5). However, since such chimeric antibodies still contain many non-human amino acid residues, the antibodies may induce a HAMA response, especially when they are administered for a long term (Begent et al., Br. J. Cancer, (1990) 62, 487).

A method for further reducing amino acid residues derived from a non-human mammal that may induce a HAMA response to humans was proposed, and the method involved grafting only the CDRs into a human antibody (Peter T et al. Nature, (1986) 321, 522-5). However, grafting of only the CDRs was normally insufficient to exhibit immunoglobulin activity against an antigen. In 1987, Chothia et al. used X-ray crystal structural analysis data to find the following: (a) the amino acid sequences of the CDRs contain the sites that directly bind to an antigen and the sites that maintain the structures of the CDRs, and possible three-dimensional structures of the CDRs are classified into several typical patterns (canonical structures); and (b) the canonical structure classes are determined by not only the CDRs but also the types of the amino acids located at specific positions in the framework (Chothia C. et al. J. Mol. Biol. (1987) 196, 901-17). These findings suggested that, when CDR grafting is performed, part of the amino acid residues in the framework should also be grafted into a human antibody in addition to the CDR sequences (JP 4-502408 T).

An non-human mammal antibody having a CDR(s) to be grafted to a human antibody is in general defined as "donor", and the human antibody into which the CDR(s) is(are) to be grafted is defined as "acceptor". In CDR grafting, the structure(s) of the CDR(s) should be conserved as much as possible to ensure the retention of the activity of the immunoglobulin molecule. To achieve this, key points to note are: (a) from which subgroup the acceptor should be selected, and (b) which amino acid residues should be selected from the donor framework.

Queen et al. proposed a method for designing a humanized antibody, involving grafting the amino acid residues from a donor framework together with the CDR sequences into an acceptor with the proviso that the amino acid residues from the donor framework satisfy at least one of the following criteria (JP 4-502408 T):
(a) the amino acids to be substituted are rare for their positions in the acceptor framework region, and the corresponding amino acids from the donor are common for their positions in the acceptor framework region;
(b) the amino acids are immediately adjacent to one of the CDRs; and
(c) the amino acids are predicted to have a side chain atom within about 3 angstroms of the CDRs in a three-dimensional immunoglobulin model and to be capable of interacting with an antigen or with the CDRs of the humanized antibody.

The DNA encoding the heavy or light chain of an anti-Exon-21 monoclonal antibody of the present invention can be produced by preparing mRNA from hybridoma cells that produce the anti-Exon-21 monoclonal antibody, converting the mRNA to cDNA with a reverse transcriptase, and isolating the DNA encoding the heavy or light chain of the antibody.

Production of Human Antibodies

The term "human antibody" or "human immunoglobulin" herein means an immunoglobulin in which its constituent regions, including the heavy chain variable regions (VH) and the heavy chain constant regions (CH) as well as the light chain variable regions (VL) and the light chain constant regions (CL), are all derived from a gene encoding a human immunoglobulin. In other words, the term means an antibody in which the heavy chains are derived from a human immunoglobulin heavy chain gene and the light chains are derived from a human immunoglobulin light chain gene.

A human antibody can be produced by conventional methods. For example, at least a human immunoglobulin gene is integrated into a locus of the gene of a non-human mammal such as a mouse to generate a transgenic animal, and the transgenic animal is immunized with an antigen, followed by the same procedures as described above for the production of monoclonal antibodies. Transgenic mice producing human antibodies can be generated, for example, by the methods described in prior documents (Mendez M J et al. Nature Genetics (1997) 15, 146-56; Green L L et al. Nature Genetics (1994) 7, 13-21; JP 4-504365 T; WO 94/25585; Nikkei Science, June, pp. 40-50, 1995; Nils Lonberg et al. Nature (1994) 368, 856-9; and JP 6-500233 T).

The antibody used in the present invention is not limited to the whole antibody molecule and may be an antibody fragment or derivative as long as the fragment or derivative neutralizes the activity of a periostin isoform having cell adhesion activity.

The antibody fragment may be, for example, a Fab, a $F(ab')_2$, Fv, a single chain antibody (scFv), a disulfide-stabilized antibody (dsFv), a CDR-containing peptide, or the like.

The antibody fragment Fab, $F(ab')_2$, or the like of the present invention can be produced by treating an antibody inhibiting the cell adhesion activity of periostin with a protease such as papain or pepsin, or alternatively, can be produced by constructing a gene encoding the antibody fragment and introducing the construct into an expression vector, followed by expression in an appropriate host cell.

The antibody fragment scFv of the present invention can be produced by linking an H chain V region with an L chain V region from an antibody inhibiting the cell adhesion activity of periostin via an appropriate peptide linker etc. Alternatively, the scFv can, be produced by constructing DNA segments encoding the entire sequences or desired amino acid sequences of genes encoding the H chain or H chain V region and encoding the L chain or L chain V region of the antibody, and introducing the constructs into an expression vector, followed by expression in an appropriate host cell.

The antibody fragment dsFv of the present invention is an antibody fragment produced by preparing the H chain V region and the L chain V region from an antibody inhibiting the cell adhesion activity of periostin, subjecting the regions to substitution of one amino acid residue for a cysteine residue to give two modified polypeptides, and linking the polypeptides between the cysteine residues via a disulfide linkage. The amino acid residue to be substituted for a cysteine residue can be selected using protein structure prediction of the antibody. Alternatively, the dsFv can be produced by constructing a DNA segment encoding the entire sequence or desired amino acid sequence of a gene encoding the antibody fragment, and introducing the construct into an expression vector, followed by expression in an appropriate host cell.

The antibody fragment CDR-containing peptide of the present invention is produced so as to comprise at least one or more CDR regions selected from the CDR regions in the H or L chains of an antibody inhibiting the cell adhesion activity of periostin. Alternatively, several CDR regions may be linked by techniques using an appropriate peptide linker or the like. The CDR-containing peptide can also be produced by constructing a DNA segment encoding the entire sequence or desired amino acid sequence of a gene encoding the peptide, and introducing the construct into an expression vector, followed by expression in an appropriate host cell. Alternatively, the CDR-containing peptide can also be produced by chemical synthesis such as the Fmoc or tBoc method.

In the present invention, a derivative comprising the above antibody or antibody fragment linked to a protein or low-molecular compound can also be used. Such modification may be accomplished by known techniques.

A DNA encoding the antibody, the antibody fragment or their protein-linked derivative of the present invention can be determined by a conventional method. The DNA can be used to produce a recombinant vector containing the DNA by a conventional method, and the recombinant vector can be introduced into a host cell by a conventional method to give a transformant. The transformant can be cultured by a conventional method to produce the antibody, the antibody fragment or their protein-linked derivative in the culture. From the culture, the antibody, the antibody fragment or their protein-linked derivative can be harvested. In this manner, the antibody, the antibody fragment, and their protein-linked derivative can be produced.

In an embodiment of the present invention, the antibody, the antibody fragment and/or the antibody derivative of the present invention can be used to prevent or treat inflammation-associated diseases in which a periostin isoform having cell adhesion activity is involved.

The term "inflammation-associated diseases in which a periostin isoform having cell adhesion activity is involved" refers to diseases during which the gene of a periostin isoform having cell adhesion activity is highly expressed and during which the production of the protein isoform encoded by the gene is increased. The term also refers to diseases whose pathology is exacerbated by an increase in the gene or protein expression.

Such inflammation-associated diseases in which a periostin isoform having cell adhesion activity is involved are not particularly limited, and include diseases of which the primary cause is vascular intimal hyperplasia, cancers and other inflammation-associated diseases. Examples of the diseases of which the primary cause is vascular intimal hyperplasia include arteriosclerosis, restenosis primarily caused by vascular intimal hyperplasia observed after coronary angioplasty, etc. Cancers to which the antibody, the antibody fragment and/or the antibody derivative of the present invention can be applied include, but are not limited to, for example, brain tumor, leukemia, osteosarcoma, breast cancer, colorectal cancer, melanoma, bone cancer, stomach cancer, lung cancer, liver cancer, renal cancer, pancreatic cancer, gall bladder cancer, skin cancer, uterine cancer, ovarian cancer, rectal cancer, colon cancer, tubal cancer, esophagus cancer, small intestine cancer, thyroid cancer, parathyroid cancer, adrenal cancer, prostate cancer, bladder cancer, malignant lymphoma, etc. Particularly suitable cancers are breast cancer, colorectal cancer, lung cancer and melanoma. Examples of said other inflammation-associated diseases include autoimmune arthritis, atopic dermatitis, asthma, pulmonary emphysema, Behcet disease, multiple sclerosis, spinocerebellar degeneration, uveitis, Guillain-Barre syndrome, Fisher syndrome, chronic inflammatory demyelinating polyneuropathy, polymyositis, scleroderma, autoimmune hepatitis, sarcoidosis, chronic pancreatitis, inflammatory enterocolitis, Crohn's disease, solid cancers, multiple myeloma, angiofibroma, atherosclerosis, arteriovenous malformations, granuloma, hemangioma, hypertrophic scars, keloids, progeria, psoriasis, pyrogenic granuloma, verrucae, hemarthrosis, ununited fractures, rheumatoid arthritis (e.g., malignant rheumatoid arthritis etc.), osteoarthritis, follicular cysts, ovarian hypertrophy syndrome, polycystic ovary syndrome, age-related macular degeneration, diabetic retinopathy, neovascular glaucoma, trachoma, pulmonary emphysema, chronic bronchitis, obesity, periodontosis, angiogenesis associated with corneal graft, aneurysm, etc. Angiogenesis is involved in many of the above inflammation-associated diseases.

Another embodiment of the present invention includes a diagnostic reagent for inflammation-associated diseases in which a periostin isoform having cell adhesion activity is involved, the diagnostic reagent being produced by labeling any of the above antibodies with a marker. The marker is not particularly limited and examples thereof include enzymes, radioisotopes, fluorescent dyes, etc. The enzymes used herein are not particularly limited as long as they satisfy certain conditions, such as having a high turnover number, remaining stable even after conjugation, and specifically reacting with their substrates to develop color, etc. Enzymes used in conventional enzyme immunoassay (EIA) can be used. Examples of preferred enzymes include peroxidases, β-galactosidases, alkaline phosphatases, glucose oxidase, acetylcholine esterase, glucose-6-phosphate dehydrogenase, malate dehydrogenase, etc. Enzyme inhibitors and coenzymes etc. can also be used.

Conjugation of the enzyme and antibody can be performed by a known method using a known crosslinker such as maleimide compounds. Substrates that can be used are known substances selected depending on the enzyme used. For example, when the enzyme used is a peroxidase, 3,3', 5,5'-tetramethylbenzidine can be used. When the enzyme used is an alkaline phosphatase, paranitrophenol or the like can be used. Radioisotopes that can be used as a marker include those used in conventional radioimmunoassay (RIA) such as $^{125}I$ and $^{3}H$. Fluorescent dyes that can be used are those used in conventional fluoroimmunoassay such as fluorescence isothiocyanate (FITC) and tetramethyl rhodamine isothiocyanate (TRITC). The present diagnostic reagent can also be used for immunohistological staining that specifically stains cancer cells and the surrounding fibroblasts. When the diagnostic reagent is labeled with a radioisotope, the diagnostic reagent can also be internally administered for imaging of cancer lesions etc.

Another embodiment of the present invention provides a method for detecting or quantifying a periostin isoform having cell adhesion activity in a biological sample, i.e., serum, prepared from human or animal blood, the method using the antibody, the antibody fragment and/or the antibody derivative of the present invention. The present invention also provides a method for diagnosing an inflammation-associated disease (e.g., heart failure etc.) in which a periostin isoform having cell adhesion activity is involved, the method comprising detecting or quantifying the periostin isoform. In the present methods, a periostin isoform having cell adhesion activity can be detected by so-called sandwich ELISA (enzyme-linked immunosorbent assay). A diagnostic kit of the present invention is used as follows. An anti-periostin primary antibody is immobilized on a plate, a sample is contacted with the plate to form a complex with the primary antibody, then an anti-periostin secondary antibody labeled with a marker is allowed to bind to the complex, and the signal intensity of the marker in the ternary complex is measured to detect and quantify a periostin isoform having cell adhesion activity. Since a periostin isoform having cell adhesion activity is a splice variant that is specifically expressed in conditions such as cancers, monitoring of the production of the periostin isoform can be used to diagnose the conditions such as cancers.

As described above, the antibody of the present invention can be labeled and used as a secondary antibody.

Another embodiment of the present invention provides a pharmaceutical composition for inhibiting a periostin isoform having cell adhesion activity, the composition comprising the antibody, the antibody fragment and/or the antibody derivative of the present invention as an active ingredient. Since the antibody, the antibody fragment and/or the derivative has an inhibitory activity on a periostin isoform having cell adhesion activity, the pharmaceutical composition inhibits angiogenesis, inhibits vascular intimal hyperplasia, treats a cancer, and prevents or treats aneurysm. That is, the present invention provides a composition for inhibiting vascular intimal hyperplasia, treating a cancer, inhibiting angiogenesis, or preventing or treating aneurysm, the composition comprising an anti-periostin antibody that recognizes a periostin splice variant having cell adhesion properties. The composition of the present invention can be used to treat and prevent restenosis that is primarily caused by vascular intimal hyperplasia observed after coronary angioplasty, to prevent or treat a cancer, to treat or prevent diseases accompanied by angiogenesis, and to prevent or treat aneurysm.

Another embodiment of the present invention provides a pharmaceutical composition for preventing or treating an inflammation-associated disease in which a periostin isoform having cell adhesion activity is involved, the composition comprising the antibody, the antibody fragment and/or the derivative of the present invention as an active ingredient. Examples of the embodiment of the present invention include a pharmaceutical composition for inhibiting vascular intimal hyperplasia, the composition comprising the antibody, the antibody fragment and/or the antibody derivative as an active ingredient; a pharmaceutical composition for treating a cancer, the composition comprising the antibody, the antibody fragment and/or the antibody derivative as an active ingredient; a pharmaceutical composition for inhibiting angiogenesis, the composition comprising the antibody, the antibody fragment and/or the antibody derivative as an active ingredient; a pharmaceutical composition for preventing or treating aneurysm, the composition comprising the antibody, the antibody fragment and/or the antibody derivative as an active ingredient; etc.

The composition of the present invention for treating a cancer exhibits the effects of inhibiting the growth of cancer foci and of inhibiting the metastasis of a cancer. The composition, hence, can be used with the intended purpose of inhibiting the growth of cancer foci or of inhibiting the metastasis of a cancer, or both purposes.

The pharmaceutical composition comprising the antibody, the antibody fragment and/or the antibody derivative of the present invention as an active ingredient is prepared with the use of known pharmacologically acceptable additives that are commonly used in a conventional preparation method, including a carrier, an excipient, and other additives.

The active ingredient of the pharmaceutical composition according to the present invention is preferably administered in admixture with a known pharmacologically acceptable carrier, excipient, diluent, or the like by any mode of administration commonly used in the pharmaceutical field (for example, by oral administration or parenteral administration such as intravenous, intramuscular and subcutaneous administrations). The pharmaceutical composition of the present invention can be prepared by, for example, mixing the active ingredient with a pharmacologically acceptable carrier, flavor, excipient, stabilizer, diluent, emulsifier, solution, suspension, syrup, or the like, as needed. The dosage form of the pharmaceutical composition of the present invention is not particularly limited and examples thereof include tablets, powders, granules, solutions, etc. Additives that can be incorporated into tablets or the like include, for example, binders such as gelatin and lubricants such as corn starch. The pharmaceutical composition may be coated with a sugar or a gastric or enteric film. When the dosage form is a capsule, the composition can further comprises a liquid carrier. The composition can be formulated into an injectable sterile composition with a conventional pharmaceutical formula. Injectable aqueous vehicles include isotonic solutions containing glucose etc., and such isotonic solutions may be used in combination with an appropriate solubilizer such as polyethylene glycol. The pharmaceutical composition may be incorporated with a buffer, a stabilizer, a preservative, an antioxidant, a soothing agent, or the like. For oral administration, when the active ingredient is likely to be decomposed in the digestive tract, the composition may be made into a formulation that are resistant to decomposition in the digestive tract (for example, liposome microcapsules encapsulating the active ingredient) and then orally administered. Other modes of administration for absorption through mucous membrane other than the digestive tract are also possible, including rectal, intranasal, sublingual and transpulmonary routes. In these cases, the composition can be administered in the form of a suppository, a nose drop, a sublingual tablet, a transpulmonary agent, or the like.

When the pharmaceutical composition of the present invention is used for therapeutic purposes, the dosage is determined so as to be therapeutically effective. The therapeutically effective dosage varies with, e.g., the age, the body weight and the severity of the symptoms of a subject to which the composition is to be administered, and the route of administration. For these reasons, the dosage is determined on an individual basis. In general, the daily dosage for an adult by oral administration is about 0.1 to 1,000 mg, and the dosage is given as a single dose or one to several divided doses (twice, three times, etc.). For continuous intravenous administration, the composition can be administered at a dosage of 0.01 µg/kg·min to 1.0 µg/kg·min, desirably 0.025 µg/kg·min to 0.1 µg/kg·min.

Other embodiments of the present invention provide "a method for inhibiting a periostin isoform having cell adhesion activity by using an antibody against the periostin isoform", "a method for preventing or treating an inflammation-associated disease in which a periostin isoform having cell adhesion activity is involved, the method comprising administering, to a cancer patient, a therapeutically effective amount of an anti-periostin antibody that recognizes a periostin splice variant having cell adhesion properties", etc. Other embodiments of the present invention provide "use of an antibody against a periostin isoform having cell adhesion activity for production of a pharmaceutical composition for inhibiting the periostin isoform", "use of an antibody against a periostin isoform having cell adhesion activity for production of a pharmaceutical composition for preventing or treating an inflammation-associated disease in which the periostin isoform is involved", etc. The anti-periostin antibody includes the above-described antibodies, antibody fragments and/or antibody derivatives. The inflammation-associated disease includes the above-described inflammation-associated diseases.

EXAMPLES

The present invention will be described in more detail with reference to Examples, but is not limited to thereto. Various modifications may be made by a person having ordinary skill in the art, without departing from the technical idea of the present invention.

Preparation Example 1

Search for Periostin by Subtraction
1-1 Establishment of Pathological Model Rats of Heart Failure and Harvest of Left Ventricular Samples Male Dahl salt-sensitive rats (Dahl-S) (Shimizu Laboratory Supplies Co., Ltd.) were raised on an 8% high salt diet from 6 weeks of age, and the left ventricles were harvested from three animals at the cardiac hypertrophy stage (11 weeks of age) and from three animals at the heart failure stage (14 weeks of age).
1-2 Preparation of mRNAs
Total RNAs were prepared from about 500 mg of each left ventricle using ISOGEN (Nippon Gene) as instructed by the manufacturer. The total RNAs from the three animals at the cardiac hypertrophy stage and the total RNAs from the three animals at the heart failure stage were separately combined. mRNAs were purified from about 400 µg of each of the combined total RNAs using Fast Track 2.0 Kit (Invitrogen) as instructed by the manufacturer to recover about 3 µg of mRNA from each stage.
1-3 cDNA Subtraction
cDNA subtraction was performed using PCR-Select cDNA Subtraction Kit (Clontech) as instructed by the manufacturer. Briefly, cDNAs were synthesized from 2 µg of each mRNA obtained in the above section 1-2 and digested with restriction enzyme RsaI. The cDNA synthesized from the animals at 14 weeks of age was used as tester cDNA and the cDNA synthesized from the animals at 11 weeks of age was used as driver cDNA. To the tester cDNA, two types of adapters included in the kit were separately ligated. Subtraction hybridization was performed. PCR was then performed using primers complementary to the adapters to specifically amplify differentially expressed cDNA fragments to give amplification product 1.
Another subtraction operation was performed in the same manner as above except that the cDNA synthesized from the animals at 11 weeks of age was used as tester cDNA and that the cDNA synthesized from the animals at 14 weeks of age was used as driver cDNA to give amplification product 2.
1-4 Dot Blot Screening
A. Preparation of Dot Blots
Amplification product 1 was TA cloned into PCR II vector (Invitrogen) and clones with the insert fragment were selected. The insert fragment of each clone was amplified by PCR reaction, and 1 µL of each amplified product was heat-treated, then dot-blotted on two nylon membrane filters (Boehringer) and fixed with a UV crosslinker (Stratagene).

B. Preparation of cDNA Probes
Amplification product 1 was digested with restriction enzymes RsaI, EaeI and SmaI to remove the adapters. The product was then subjected to random prime labeling with DIG-dUTP using DIG High Prime DNA Labeling and Detection Kit II (Boehringer) as instructed by the manufacturer to prepare cDNA probe 1. In the same manner, cDNA probe 2 was prepared from amplification product 2.
C. Screening
One of the dot blot membranes prepared in the above section A was hybridized with cDNA probe 1 and the other was hybridized with cDNA probe 2. Specifically, hybridization was performed in a hybridization solution (DIG Easy Hyb solution) at 42° C. overnight using DIG High Prime DNA Labeling and Detection Kit II (Boehringer) as instructed by the manufacturer. The membranes were washed twice with 2×SSC and 0.1% SDS at room temperature for 5 minutes and then twice with 0.1×SSC and 0.1% SDS at 68° C. for 15 minutes. The membranes were then reacted with the alkaline phosphatase-conjugated DIG antibody in blocking buffer included in the kit. A chemiluminescence substrate (CSPD ready-to-use) was added to allow chemiluminescent reaction to proceed. The membranes were exposed to X-ray films. Clones showing a stronger signal with cDNA probe 1 than with cDNA probe 2 were selected as positive clones and sequenced.
1-5 Sequencing
The nucleotide sequences were determined by analysis on an automated DNA sequencer, Model 373A (PE Applied Biosystems), using a dye terminator sequencing kit (trade name: Thermo Sequenase™ II Dye Terminator Cycle Sequencing Kit (Amersham Pharmacia)). The obtained gene sequences were compared with sequences available from the GenBank databank. One of the clones (SF014) was found to have a gene having 86% homology to mouse periostin (GenBank Accession No. D13664).

Preparation Example 2

Cloning of Rat Periostin-1 cDNA

Rat periostin cDNA was isolated as follows. A rat aorta cDNA library (Clontech) was inserted into λgt 11 vector to generate 10 phage subpools of about 4,000 clones (a total of about 40,000 clones). The phage subpools were screened by PCR using primers (1) 5'-GTTCATTGAAGGTGGCGATG-GTC-3' (SEQ ID NO: 23) and (2) 5'-GAGATAAAATCCCT-GCATGGTCCT-3' (SEQ ID NO: 24) that were designed based on the nucleotide sequence of SF014. As a result of the screening, three positive subpools were obtained. One of the subpools was screened by hybridization using the above fragment amplified by PCR as a probe, labeled with alkaline phosphatase using AlkPhos Direct™ (Amersham Pharmacia), to give one positive clone rat periostin #1. Its insert fragment was subcloned into the EcoRI site of pBluescript II (Stratagene) and the complete nucleotide sequence was determined by the method described in 1-5 of Preparation example 1.
The resulting clone had a length of about 3 kb, corresponding to the nucleotides from position 292 to the 3' end of mouse periostin (GenBank Accession No. D13664). The results suggest that the clone was a 5'-truncated clone.
A SMART RACE cDNA amplification kit (trade name: SMART™ RACE cDNA Amplification Kit (Clontech)) was used as instructed by the manufacturer to perform 5'-RACE reaction using rat aorta cDNA as a template and primers (2) 5'-GAGATAAAATCCCTGCATGGTCCT-3' (SEQ ID NO: 24) as described above and (3) 5'-CACGGTCGAT- GACATGGACAACACC-3' (SEQ ID NO: 25) designed based on the nucleotide sequence of rat periostin #1. The resulting PCR product was TA cloned into PCR II vector (Invitrogen) to give a clone. The clone was designated as rat periostin 5' RACE #1. The nucleotide sequence was determined by the method described in 1-5 of Preparation example 1.

The results showed that rat periostin 5' RACE #1 was a clone of which the nucleotide sequence is longer than that of the initially obtained rat periostin #1 by about 300 by in the 5' direction, and that the 5' end of rat periostin 5' RACE #1 is longer by 15 by than the 5' end of mouse periostin (GenBank Accession No. D13664). The above ten phage subpools of about 40,000 clones (a total of about 400,000 clones) prepared from the rat aorta cDNA library were screened by PCR using primers (4) 5'-ACGGAGCTCA-GGGCTGAAGATG-3' (SEQ ID NO: 26) designed based on the nucleotide sequence of rat periostin 5' RACE #1 and (3) 5'-CACGGTCGATGACATGGACAACACC-3' (SEQ ID NO: 25) as described above, to give two positive subpools. One of the subpools was screened by hybridization using the above fragment amplified by PCR as a probe to give one positive clone. The clone was designated as rat periostin #2. Its insert fragment was subcloned into the EcoRI site of pBluescript II (Stratagene) and the nucleotide sequence was determined by the method described in 1-5 of Preparation example 1.

The resulting clone had a length of about 2.6 kb. The 5' end was identical to that of the clone obtained from the 5'-RACE reaction and the 3' end corresponded to the nucleotides up to position 2410 of mouse periostin (GenBank Accession No. D13664). The nucleotide sequence of rat periostin 5' RACE #1 previously obtained was identical to the nucleotide sequence of the relevant region of rat periostin #2. The full length of rat periostin cDNA was completed by rat periostin #1 and rat periostin #2. The nucleotide sequence of the full-length cDNA is shown in SEQ ID NO: 2, and the amino acid sequence translated from the nucleotide sequence is shown in SEQ ID NO: 1.

Preparation Example 3

Cloning of cDNAs of Rat Periostins-2 and -4

PCR was performed from the cDNA of the Dahl rats at the cardiac hypertrophy stage used in Preparation example 1 and the gene sequence cloned in Preparation example 2 using primers 5'-AAGCTAGCGAAGATGGTTCCTCTCCTGC-CCT-3' (SEQ ID NO: 27) and 5'-CTTTGGGTTTTTCCA-GCCTC-3' (SEQ ID NO: 28). The PCR product was TA cloned into pCR4 Blunt TOPO vector (Invitrogen). From the resulting colonies, 96 colonies were selected and transferred to a 96-well plate so as to be 1 colony/well. Screening for candidate rat periostin-2 and -4 genes was performed using primers 5'-CCCCATGACTGTCTATAGACCT-3' (SEQ ID NO: 29) and 5'-ATTTCCCTTAAAAATCAGATTG-3' (SEQ ID NO: 30). The selected clones were further screened by sequencing for clones with no PCR errors.

Preparation Example 4

Construction of Baculovirus Expression Vectors

The plasmids pCR4 Blunt TOPO/rat periostin-2 and pCR4 Blunt TOPO/rat periostin-4 prepared in Preparation example 3 were digested with restriction enzymes Spe I and Not I to excise rat periostin-2 and -4 fragments. The fragments were separately ligated using a ligation kit (Takara Bio Inc.) to a pFastBacHTc (Invitrogen) vector fragment digested with restriction enzymes pe I and Not I to give expression vectors. The vectors were designated as pFastBac/rat periostin-2 and pFastBac/rat periostin-4, respectively. The nucleotide sequences of the inserts were confirmed by the method described in 1-5 of Preparation example 1.

Preparation Example 5

Preparation and Culture of Recombinant Baculoviruses

*Escherichia coli* DH10BAC cells were transformed separately with each of pFastBac/rat periostin-2 and pFastBac/rat periostin-4 prepared in Preparation example 4 to produce recombinant baculoviruses. The insertion of the desired inserts in the resulting baculoviruses was confirmed by electrophoresis and PCR.

Insect Sf9 cells ($2\times10^6$ cells/mL) were infected separately with each of the recombinant baculoviruses at MCI=0.1, and then cultured in serum-free medium (2,000 mL of Sf-900 II SFM (Invitrogen) containing 50 µg/mL gentamicin) at 28° C. for 4 to 5 days. The culture supernatants were harvested.

Preparation Example 6

Purification of Rat Periostin Proteins

To SP Sepharose Fast Flow columns (10 mL bed volume) equilibrated with equilibration buffer (50 mM sodium acetate buffer, pH 6.0, 0.1 M sodium chloride) were separately applied 2,000 mL of each of the culture supernatants obtained in Preparation example 5, and the resulting flow-through fractions were separately pooled to give SP Sepharose flow-through fractions.

The columns were washed with the equilibration buffer (about 100 mL) until the absorbance at 280 nm approached zero to give SP Sepharose wash fractions.

The columns were eluted with 100 mL of elution buffer (50 mM sodium dihydrogen phosphate (pH 8.0), 0.5 M sodium chloride, 5 mM imidazole) to give SP Sepharose eluate fractions.

The SP Sepharose eluate fractions each in an amount of 100 mL were separately applied to Ni-NTA agarose columns (5 mL bed volume) equilibrated with 50 mM sodium phosphate buffer, pH 8.0, 0.5 M sodium chloride and 5 mM imidazole. The resulting flow-through fractions were separately pooled to give Ni-NTA agarose flow-through fractions.

The columns were washed with about 50 mL of washing buffer (50 mL sodium dihydrogen phosphate, pH 8.0, 0.5 M sodium chloride, 5 mM imidazole) to give Ni-NTA agarose wash fractions.

The columns were eluted with about 25 mL of each of the following elution buffers: (1) 50 mM sodium dihydrogen phosphate, 0.5 M sodium chloride, 20 mM imidazole, followed by elution buffers with the same formulations except that the imidazole concentrations were (2) 30 mM, (3) 40 mM, (4) 50 mM and (5) 60 mM, to give Ni-NTA agarose eluate fractions (1) to (5).

The fractions shown to contain the desired proteins by Western blotting were concentrated to 1 mL or less.

The concentrated samples were applied to gel filtration columns (Sephacryl S-200HR, 11 mm diameter×95 cm; 90 bed volume) equilibrated with degassed PBS (−) (137 mM NaCl, 8.1 mM $Na_2HPO_4$, 2.68 mM KCl, 1.47 mM $KH_2PO_4$), and were eluted with PBS (−). The eluates were lyophilized to give purified rat periostin proteins.

Example 1

Figure 2:
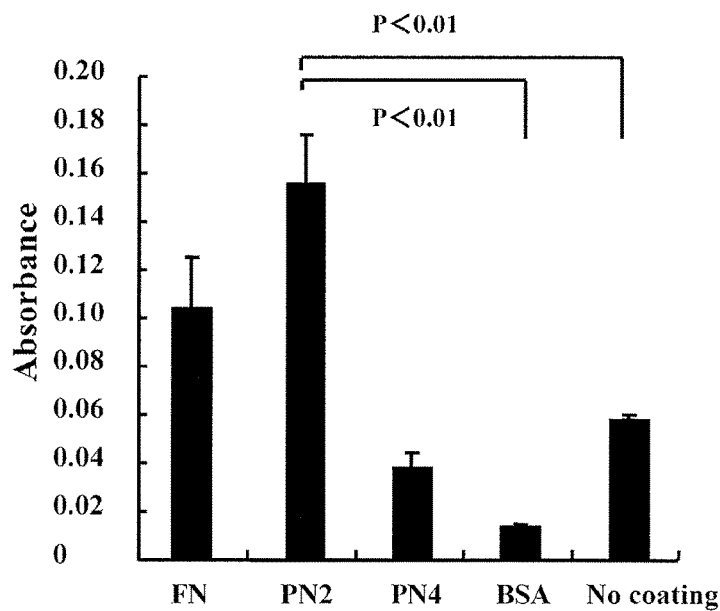
FIG. 2 is a chart showing the assay results of the cell adhesion properties of rat PN-2 and PN-4 proteins in Example 1.

In Vitro Study of the Presence or Absence of Cell Adhesion Activity of Rat PN-2 and PN-4 Proteins To a 96-well cell culture multi-well plate, 10 μg/mL fibronectin, 100 μg/mL BSA, 10 μg/mL PN-2 protein, and 10 μg/mL PN-4 protein were separately added and incubated at 4° C. overnight so that the wells were coated with each protein. After removal of the protein solution from the wells, rat neonatal cardiac fibroblasts suspended in DMEM (10% BSA, PC/SM) were added at $10^4$ cells/well and cultured in a 37° C. incubator for 3 hours. The level of cell adhesion was measured as follows. After removal of the culture supernatant, the cells were fixed in 2.5% glutaraldehyde for 30 minutes, stained with 0.02% crystal violet and then measured for their absorbance at OD 550 nm with a plate reader (BIO-RAD, Model 680 MICRO PLATE READER). Uncoated wells were stained as background samples and used to correct the absorbance values for comparison purposes. Data analysis was made by the Fisher's PLSD test (FIG. 2). The positive control fibronectin (indicated by FN in the figure) showed cell adhesion, whereas the negative control BSA showed no cell adhesion. The wells without protein coating also showed cell adhesion, but the level was smaller than that of the positive control fibronectin. The group to which rat PN-2 protein was added showed a cell adhesion level equal to or higher than that of the fibronectin group, whereas the group to which rat PN-4 protein was added showed a cell adhesion level merely equal to that of the uncoated wells.

Example 2

Synthesis of Rat Exon-21 Peptide Chain and Production of Polyclonal Antibodies

In Example 1, rat PN-4 protein was shown to have lower cell adhesion properties than rat PN-2 protein. From this fact and the results of sequence comparison of the proteins, the structure specific to rat PN-2 protein was revealed to be the Exon-21 sequence. Based on this, a peptide having a Cys residue added to the N-terminus of the amino acid sequence constituting Exon-21 was chemically synthesized in a 10 mg yield at a purity of 80% or more. Rabbits (Kbl:JW) were immunized with the polypeptide conjugated to 6 mg of a carrier protein KLH. FCA (Freund's complete adjuvant) was used in the primary immunization (administration), and FIA (Freund's incomplete adjuvant) was used in the secondary and subsequent immunizations. Administration was performed at 20 dorsal subcutaneous sites at weeks 2, 4 and 6 after the primary administration, using a peptide dose of 800 μg/animal in the primary immunization and 400 μg/animal in the secondary and subsequent immunizations. The antibody titer was determined by ELISA and the total serum was collected at week 7 after the initiation of the administration. An affinity column was prepared by use of the synthetic peptide, and the antibodies specifically reacting to the Exon-21 peptide were isolated. The polyclonal antibodies against the peptide encoded by Exon-21 of rat periostin were referred to as anti-rat Exon-21 polyclonal antibodies.

Example 3

Confirmation of the Binding Capacity to Rat Periostin Protein (PN-2)

The two types of polyclonal antibodies (No. 1 and No. 3) produced in Example 2 were assayed by dot blotting to confirm their binding capacity to rat periostin protein (PN-2). The purified proteins (30 μg/mL) produced in Preparation example 6 were each spotted in a 5 μL volume on a Hybond-ECL nitrocellulose membrane (GE Healthcare Bio-Sciences KK) and the membrane was washed once with TBS solution (10 mM Tris-HCl (pH 8.0), 150 mM NaCl). Blocking buffer (Block Ace, Snow Brand Milk Products Co., Ltd.) was added and the membrane was shaken at room temperature for 1 hour. After a 1 μg/mL solution of each monoclonal antibody (primary antibody) was added to the membrane, the membrane was shaken for 3 hours and washing with TBS solution under 10-minute shaking was repeated four times. After a 0.4 μg/mL solution of an HRP-conjugated anti-rabbit IgG antibody (Promega) (secondary antibody) was added to the membrane, the membrane was shaken at room temperature for 1 hour and washing with TBS solution under 10-minute shaking was repeated four times. A detection reagent (ECL Plus Western Blotting Detection System, GE Healthcare Bio-Sciences KK) was added and reacted for 1 minute to detect chemiluminescence. The assay confirmed that the two types of polyclonal antibodies bind to rat periostin PN-2.

Example 4

Figure 3:
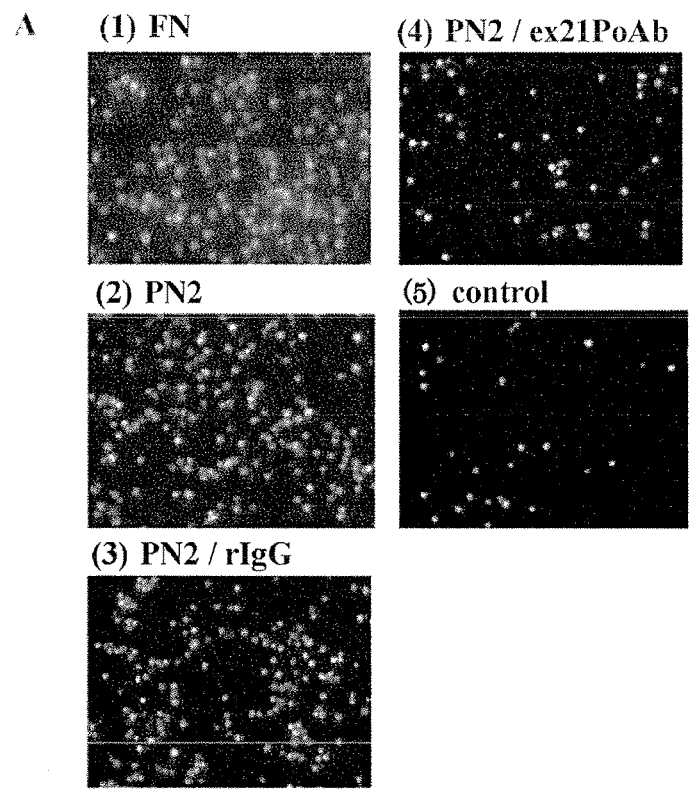
FIGS. 3A and 3B are images and a chart showing the results of the study in Example 4. The images and chart indicates that mouse PN-2 protein promotes the adhesion of THP-1 cells and induces differentiation into macrophages, whereas an anti-rat Exon-21 polyclonal antibody inhibits the adhesion of THP-1 cells and inhibits differentiation into macrophages.
Figure 3:
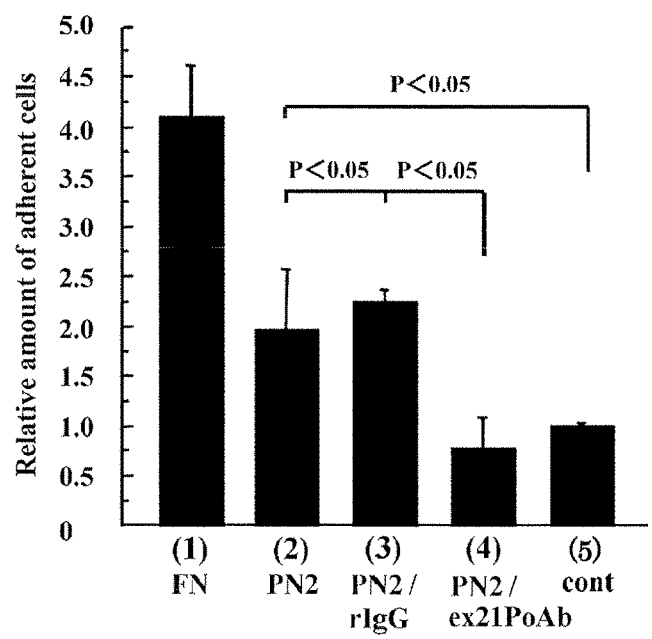

In Vitro Study of the Neutralizing Activity of Anti-Rat Exon-21 Polyclonal Antibody DB1X rat vascular smooth muscle cells A7r5 (Cat. No. 09-1444, Sumitomo Dainippon Pharma Co., Ltd.) were seeded in a 96-well cell culture multi-well plate at a density of 0.5 to $1 \times 10^4$ cells/well and cultured to subconfluence, and then the medium was replaced with a serum (−) medium. Separately, in order to fluorescently label THP-1 cells (human acute monocytic leukemia, Cat. No. 06-202, Sumitomo Dainippon Pharma Co., Ltd.), 2 nM BCECF-AM (BCECF-AM special packaging, Cat. No. B221, Dojindo Laboratories Co., Ltd.) was added to the THP-1 cells, incubated for 30 minutes, centrifuged, and washed twice with PBS (−). For the measurement of the adhesion of the fluorescently labeled THP-1 cells, the anti-rat Exon-21 polyclonal antibody (ex21PoAb) or a rabbit control IgG antibody (rIgG) was mixed with PN-2 protein and reacted at room temperature for 1 hour, and then the reacted mixture and $1 \times 10^4$ cells/well of the fluorescently labeled THP-1 cells were added to the A7r5-seeded wells. As controls, (1) fibronectin, (2) PN-2, (3) PN-2+ rabbit control IgG antibody (rIgG), and (5) THP-1 alone were used. The above mixture and the controls were incubated for 6 hours. RPMI 1640 medium was then slowly added to each well to fill it up, and the plate was covered with parafilm to exclude air. The plate was turned upside down and incubated for 30 minutes. The parafilm was then carefully removed, the medium was aspirated, and the plate was washed three times with PBS (−). As a measure of cell adhesion, the fluorescence intensity was determined with a plate reader (Wallac 1420 ARVOmx/light (Perkin-Elmer)) at an excitation wavelength of 485 nm and a fluorescence wavelength of 535 nm. As shown in FIGS. 3A and 3B, cell adhesion was observed in (1) fibronectin group, (2) PN-2 group and (3) PN-2+ rabbit control IgG antibody (rIgG)

group, whereas no significant adhesion was observed in (4) anti-rat Exon-21 polyclonal antibody (ex21PoAb) treatment group as with the case of (5) THP-1 alone. The results revealed that the anti-rat Exon-21 polyclonal antibody has inhibitory activity, i.e., neutralizing activity, against the cell adhesion properties of PN-2.

Example 5

Production of Monoclonal Antibodies Against Human Periostin Exon-21 Peptide Chain (1) Antigen Production A peptide (antigen peptide; CEVTKVTKFIE GGDGHLFEDE EIKRLLQG (SEQ ID NO: 31)) having a Cys residue added to the N-terminus of the amino acid sequence constituting human periostin Exon-21 (SEQ ID NO: 18) was chemically synthesized by the Fmoc method in a 10 mg yield at a purity of 90% or more. Then, 5 mg of a carrier protein KLH (CALBIOCHEM) was conjugated to 5 mg of the antigen peptide to give an antigen solution. Briefly, KLH was dissolved in PBS (0.01 M) to a concentration of 3.3 mg/mL. To this, a 0.2524 mg/mL MBS solution (GE Healthcare Bio-Sciences KK) was added dropwise, and the mixture was reacted with stirring at room temperature for 60 minutes. Dichloromethane was used to remove free MBS to give KLH-MB. Then, 5 mg of KLH-MB was mixed with a solution of 5 mg of the antigen peptide in 0.01 M sodium phosphate buffer (pH 7.2), and the mixture was reacted with stirring at 4° C. for 12 hours to give an antigen solution.

(2) Immunization

The antigen solution (50 μL) containing 100 μg of the KLH-conjugated antigen peptide obtained in the above (1) was mixed with FCA (Freund's complete adjuvant, 50 μL) to prepare an emulsion. The whole volume of the emulsion was subcutaneously injected into the hind paws of three female BALB/c mice at 6 weeks of age. The mice were then received additional injections twice at an interval of 2 weeks into the hind paws with a mixed emulsion of the above antigen solution and FIA (Freund's incomplete adjuvant) prepared at the time of use. The mice were then sacrificed by cervical dislocation and the lymph nodes in the paws were aseptically harvested.

The above lymph nodes were crushed in RPMI medium (Kohjin Bio Co., Ltd.) and passed through a mesh of about 10 μm pore size to give a suspension of the lymph node cells in RPMI medium. The suspension was centrifuged at 1,000 rpm for 10 minutes to give a pellet fraction of the lymph node cells. The red blood cells contained in the pellet fraction was hemolyzed with 1 mL of a solution prepared by adding 20 mM HEPES buffer (pH 7.4) to a 0.84% ammonium chloride solution. After the removal of the red blood cells, the fraction was centrifuged at 1,000 rpm for 5 minutes. The resulting pellet fraction (cell fraction) was washed several times with RPMI medium and then used for cell fusion.

(3) Preparation of Myeloma Cells

The mouse myeloma cell line P3X63Ag8U.1 (P3U1), which is resistant to 8-azaguanine and does not secrete immunoglobulin, was cultured in RPMI medium containing 20% fetal calf serum (FCS) in a 10% $CO_2$ incubator at 37° C. The cells in the logarithmic growth phase were collected and centrifuged at 1,000 rpm for 5 minutes to separate the cells as a pellet fraction. The pellet fraction was suspended in RPMI medium.

(4) Cell Fusion

The RPMI medium containing $1\times10^8$ to $3\times10^8$ immunized lymph node cells prepared in the above (2) was mixed with the RPMI medium containing $10^8$ myeloma cells prepared in the above (3). The mixture was centrifuged at 1,000 rpm for 10 minutes. The supernatant was gently removed to leave the cells as a pellet fraction, followed by addition of 1 mL of 25% (w/v) polyethylene glycol 1500 (PEG 1500, Boehringer). To this, RPMI medium was slowly added to a total volume of 10 mL. To this, 20% FCS-containing RPMI medium (10 mL) was added and allowed to stand for a while, followed by centrifugation at 1,000 rpm for 5 minutes. The resulting pellet fraction (cell fraction) was adjusted to a cell density of $10^6$ cells/mL by addition of 20% FCS-containing RPMI medium. The cell suspension was dispensed at 200 μL/well in 96-well culture plates (Corning). After culture of the cells in a 5% $CO_2$ incubator at 37° C. for 24 hours, HAT solution (Invitrogen) was added and culture was continued for additional 2 weeks.

(5) Screening by ELISA

Screening for positive wells containing the culture supernatant that showed reactivity with the antigen peptide was performed. An antigen solution used for the assay was a conjugate prepared by coupling the antigen peptide (2 mg) produced in the above (1) to ovalbumin (OVA) as a carrier protein.

Each well of a 96-well microtiter plate (Falcon 353912) was coated with the conjugate (1 μg/mL) at 4° C. overnight. After the plate was washed, 50 μL of the culture supernatant from the above (4) (containing monoclonal antibodies) was added dropwise to each well and allowed to stand in a 37° C. incubator for 2 hours, followed by washing with PBS (−) (phosphate buffered saline). After addition of alkaline phosphatase-conjugated sheep anti-mouse IgG antibody (Zymed), the plate was allowed to stand in a 37° C. incubator for 1 hour, and washed with PBS (−). A color development substrate (ALP) was added and color developed for 20 minutes. The absorbance (antibody titer) at OD 490 nm was measured for each well with a plate reader (BIO-RAD, Model 680 MICRO PLATE READER) to evaluate the reactivity with the antigen peptide and thereby to determine positive wells containing the culture supernatant that showed reactivity with the antigen peptide.

(6) Cloning of Antibody-producing Cells

Cloning of antibody-producing cell lines from the cells in the positive wells for which reactivity with the antigen peptide was confirmed by ELISA in the above (5) was performed by limiting dilution. Briefly, the cells in the positive wells were seeded into each well of a 96-well culture plate and cultured in a 5% $CO_2$ incubator at 37° C. for 2 weeks. For the culture supernatant in each well, reactivity with the antigen peptide was examined by ELISA in the same manner as in the above (5). For each positive well, cloning by limiting dilution was performed again to select 30 cells having a high reactivity with the antigen peptide and showing good colony growth. The cells were transferred to 24-well culture plates and cultured in a 5% $CO_2$ incubator at 37° C. for 2 weeks. For each culture supernatant, reactivity with the antigen peptide (antibody titer) was examined again by ELISA in the same manner as in the above (5). Cells in two wells showing a high absorbance at OD 490 nm, i.e., two hybridoma cell lines (No. 8 and No. 10) were determined to be useful as antibody-producing cells and were selected.

The thus obtained antibody-producing cells constantly produce anti-human Exon-21 monoclonal antibodies, i.e., the antibodies of the present invention, and hence the supernatant of the medium in which these antibody-producing cells have been cultured can be directly used as an antibody solution of the present invention.

The above antibody-producing cell line (hybridoma) No. 8, which produces an anti-human Exon-21 monoclonal antibody, was internationally deposited with Incorporated Administrative Agency, National Institute of Technology and Evaluation, Patent Microorganisms Depositary (NPMD) (Deposit Date: Feb. 26, 2013, Accession No.:NITE BP-01546, Identification Reference: KS-0259#8, 080611 Kohjin Bio).

(7) Confirmation of the Binding Capacity to Periostin Protein (PN-2)

Antibodies produced by the two antibody-producing cells obtained in the above (6) were assayed by dot blotting to confirm their binding capacity to mouse periostin protein (PN-2), based on the fact that mouse periostin has an almost identical amino acid sequence to that of human periostin. Briefly, mouse PN-2 protein (Recombinant Mouse Periostin/OSF-2, R&D SYSTEMS) (100 µg/mL) was spotted in 5 µL volumes on a Hybond-ECL nitrocellulose membrane (GE Healthcare Rio-Sciences KK) and the membrane was washed once with TBS solution (10 mM Tris-HCl (pH 8.0), 150 mM NaCl). Blocking buffer (Block Ace, Snow Brand Milk Products Co., Ltd.) was added and the membrane was shaken at room temperature for 1 hour. After a 1 µg/mL solution of each monoclonal antibody (primary antibody) obtained in the above (6) was added to the membrane, the membrane was shaken for 3 hours and washing with TBS solution under 10-minute shaking was repeated four times. After a 0.4 µg/mL solution of an HRP-conjugated anti-mouse IgG antibody (Promega) (secondary antibody) was added to the membrane, the membrane was shaken at room temperature for 1 hour and washing with TBS solution under 10-minute shaking was repeated four times. A detection reagent (ECL Plus Western Blotting Detection System, GE Healthcare Bio-Sciences KK) was added and reacted for 1 minute to detect chemiluminescence. The assay confirmed that the antibodies produced by the two antibody-producing cells cloned in the above (6) bind to human periostin PN-2.

(8) Mass Production and Purification of Monoclonal Antibodies

To BALE/c mice, 0.5 mL of pristine [2,6,10,14-tetramethylpentadecane (Wako Pure Chemical Industries, Ltd.)] was intraperitoneally administered and the mice were kept for 2 to 3 weeks. The monoclonal antibody-producing hybridomas No. 8 and No. 10 that had been maintained at the logarithmic growth phase were collected and centrifuged for removal of the culture supernatant. To each of the cell pellet fractions, FCS-free RPMI medium was added to prepare a cell suspension at a cell density of 1×10⁷ cells/mL. The cell suspension was intraperitoneally injected into the BALB/c mice pretreated with pristane. About three weeks later, the exuded ascites was collected from the abdominal with a syringe. The collected ascites was passed through a filter with a pore diameter of 0.22 µm, the filtrate was purified in a conventional manner by affinity chromatography on a Protein G-Sepharose column (Millipore, 11511324) to prepare two types of anti-human Exon-21 monoclonal antibodies.

Example 6

Epitope Analysis of Anti-Human Exon-21 Monoclonal Antibodies

Replitope (an array of 37 types of peptides fixed on a glass slide) was produced and used to identify the epitopes for the anti-human periostin Exon-21 peptide monoclonal antibodies (two types) and for the anti-rat periostin Exon-21 peptide polyclonal antibodies (two types).

As primary antibodies, the rabbit IgG No. 1 (0.51 mg/mL) and No. 3 (0.62 mg/mL) polyclonal antibodies, and the No. 8 Mouse IgG2b (2.21 mg/mL) and No. 10 Mouse IgG1 (1.35 mg/mL) monoclonal antibodies were used. As secondary antibodies, Cy5-conjugated anti-rabbit IgG (H+L) (JIR 111-175-144) and Dylight 649-conjugated anti-mouse IgG (Pierce, #35515) were used. The peptides were synthesized on cellulose membranes. The peptides were then transferred to microliter plates and spotted on a glass surface with a nano-pipetting system for peptide arrays (JPT Peptide Technologies GmbH, Berlin, Germany). The peptide microarray was incubated with blocking buffer (Pierce International, Superblock TBS, order #37536) for 2 hours. The microarray was incubated with the primary antibodies (10 µg/mL, in blocking buffer, total assay volume 200 µL) or blocking buffer alone in a microarray hybridization station (TECAN HS400 microarray hybridization station). The microarray was washed with TBS-buffer (50 mM TBS-buffer+0.1% Tween 20 (JPT), pH 7.2), and incubated with the fluorochrome-conjugated secondary antibodies (anti-rabbit IgG or anti-mouse IgG) at a final concentration of 1 µg/mL in blocking buffer. The microarray was washed three times with TBS-buffer and then washed with SSC-buffer (3 mM SSC-buffer (JPT), pH 7.0) and dried under nitrogen stream. The microarray was finally analyzed with a high-resolution fluorescence scanner (trade name: GenePix 4200AL, Axon, Inc.). Spot analysis was performed using a software GenePix 6.0.

As a result of the assay, the epitopes for the anti-rat Exon-21 polyclonal antibodies were identified to be the sequences TKVTK (SEQ ID NO: 21) and QGDTPVRK (SEQ ID NO: 22), and the epitopes for the anti-human Exon-21 monoclonal antibodies were identified to be the sequences VTKVTK (SEQ ID NO: 19) and FEDEEIK (SEQ ID NO: 20).

Example 7

Figure 4:
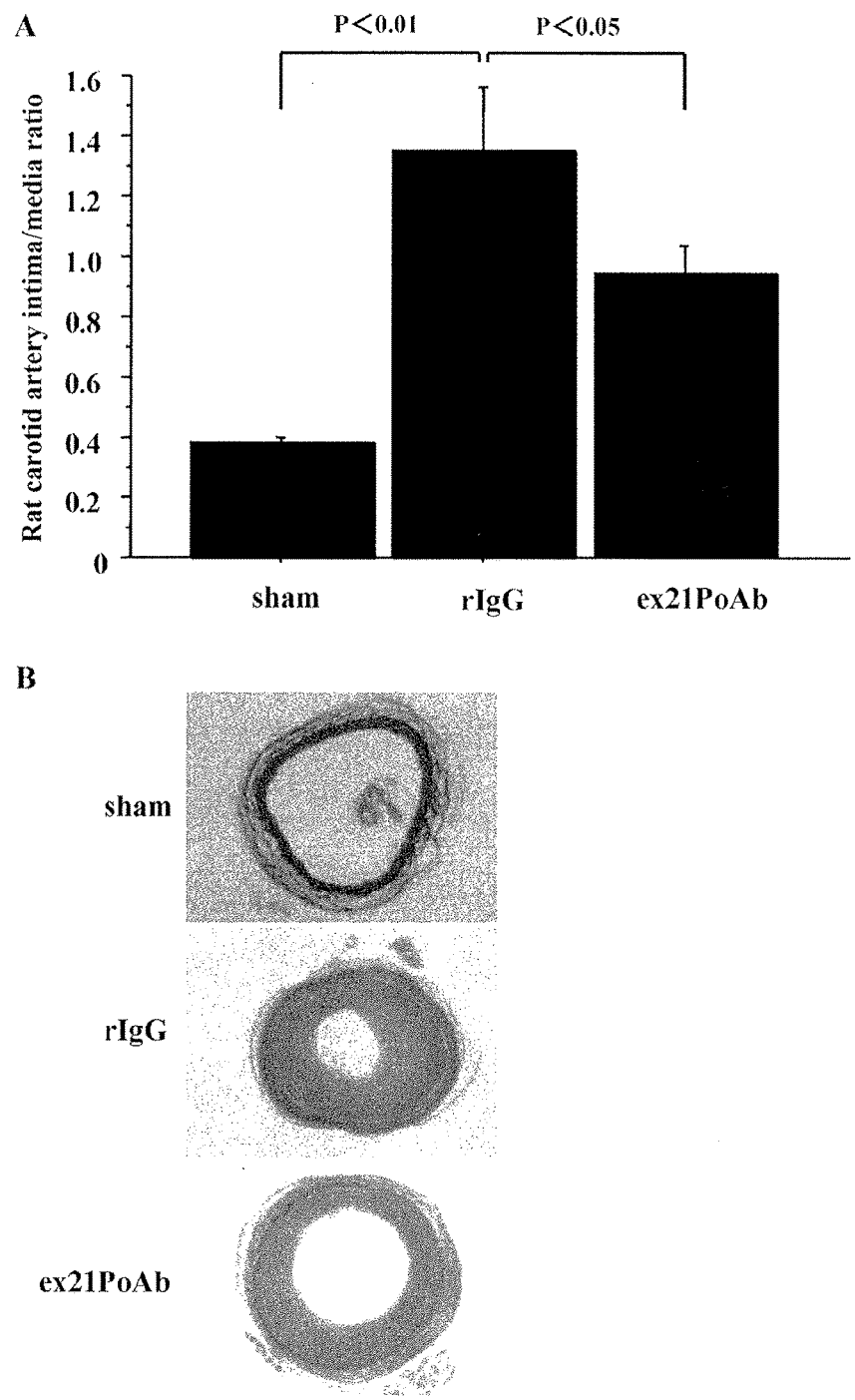
FIGS. 4A and 4B are a chart and images showing the results of the study on the neointimal hyperplasia inhibitory effect of the anti-rat Exon-21 polyclonal antibody in a rat carotid artery balloon injury model in Example 7.

Study of Inhibitory Effect of Anti-rat Exon-21 Polyclonal Antibody on Vascular Intimal Hyperplasia Using Rat Carotid Artery Balloon Injury Model Injury was induced in SD rats by scratching the left common carotid artery with a 2F (French) Fogarty balloon catheter, and simultaneously the anti-rat Exon-21 polyclonal antibody (ex21PoAb) or a rabbit control IgG antibody (rIgG) was intravascularly administered. One day, three days, one week, two weeks and three weeks after the production of the intimal injury models, five rats were fixed by perfusion for each time period. The blood vessels were harvested, and the balloon injury-induced carotid arteries as samples and the carotid arteries with no injury as controls were dissected in a length of about 1 cm from the blood vessels. About 2 to 3 mm segment of each of the dissected blood vessels was fixed in 4% paraformaldehyde, and the rest of each vessel was used for extraction of total RNA for cDNA synthesis. From the fixed tissue, sections were prepared and stained with HE (hematoxylin-eosine) (FIG. 4B). The areas of the tunica intima and the tunica media in all the HE stained sections were determined using a graphical analysis software (trade name: Graphic converter ver. 4.02). From the determined areas, the intima/media ratio was calculated, and the severity of intimal hyperplasia was examined. As shown in FIG. 4A, a significant difference of p=0.0362 (N=8) was observed in the intima/media ratio between the anti-rat Exon-21 polyclonal antibody (ex21PoAb) administration group and the rabbit control IgG antibody (rIgG) group. The results showed the inhibition of intimal hyperplasia (FIGS. 4A and 4B).

Example 8

Figure 5:
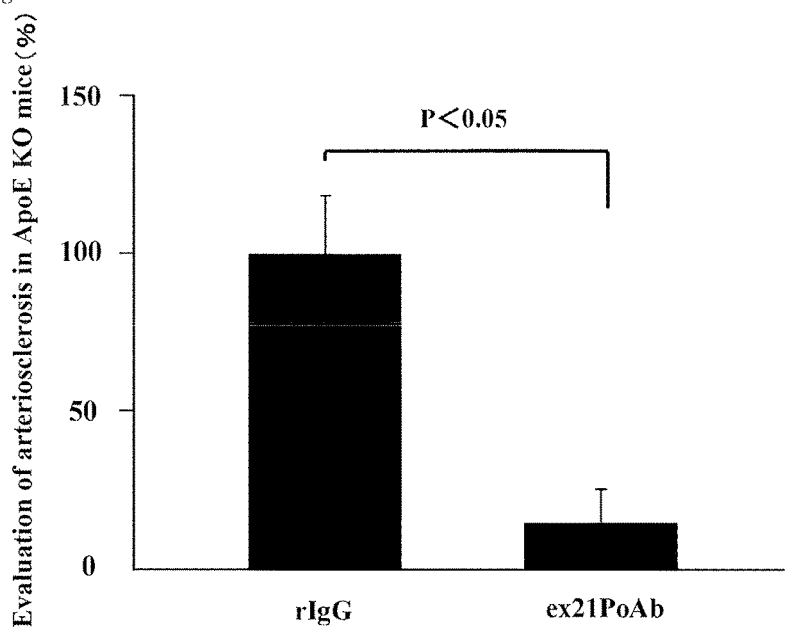
FIG. 5 is a chart showing the results of the study on the arteriosclerosis inhibitory effect of the anti-rat Exon-21 polyclonal antibody in an ApoE KO arteriosclerosis mouse model in Example 8.

Study of Inhibitory Effect of Anti-rat Exon-21 Polyclonal Antibody on Vascular Intimal Hyperplasia Using ApoE Knockout Mice ApoE knockout mice, an arteriosclerosis-prone model, were stimulated with a high-fat diet, and simultaneously with the start of high-fat diet feeding, the anti-rat Exon-21 polyclonal antibody (ex21PoAb) or a rabbit control IgG antibody (rIgG) was intraperitoneally administered at a dose of 100 μg/mL once a week. Three months later, the aorta was dissected. The developed arteriosclerotic lesions were compared in terms of the following two parameters: the severity of arteriosclerosis defined as the ratio of Oil red O stained positive area to the total blood vessel area; and the % change in the severity of arteriosclerosis defined as the severity of arteriosclerosis divided by the IgG administration group's average value of the severity of arteriosclerosis. The results showed significant inhibition of aortic arteriosclerosis in the anti-rat Exon-21 polyclonal antibody (ex21PoAb) administration group as compared with the rabbit control IgG antibody (rIgG) administration group (N=3) ($p<0.05$) (FIG. 5).

Example 9

Figure 6:
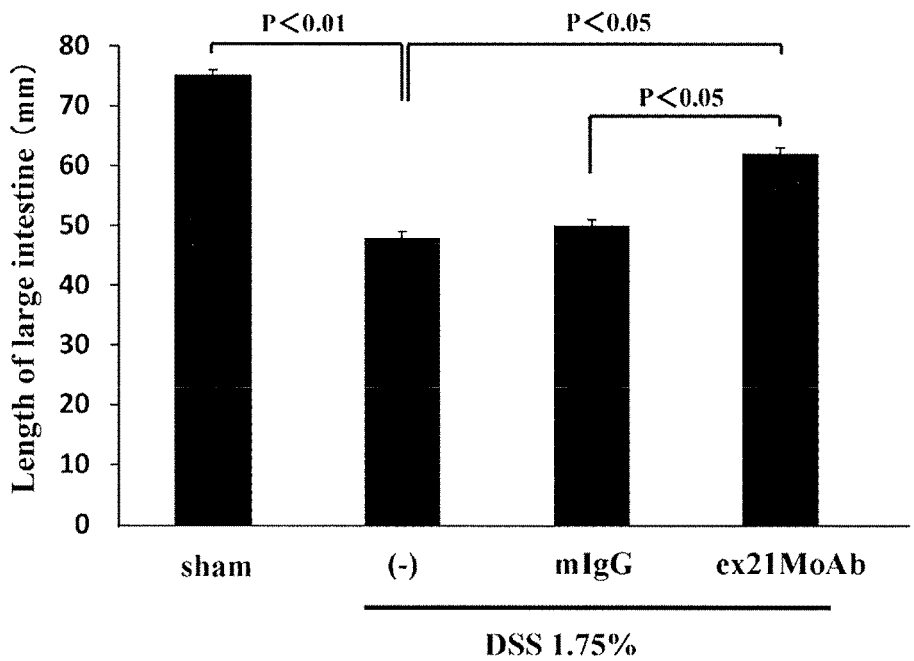
FIG. 6 is a chart showing the results of the study on the inflammation inhibitory effect of an anti-human Exon-21 monoclonal antibody in a mouse colitis model in Example 9.

Study of Anti-inflammatory Effect of Anti-human Exon-21 Monoclonal Antibody Using Mouse Colitis Model A study was performed to investigate the effect of the anti-human Exon-21 monoclonal antibody (ex21MoAb) or a mouse control IgG antibody (mIgG) on a mouse colitis model with 1.75% dextran sulfate sodium (DDS)-induced Crohn's disease. Simultaneously with DDS administration, each antibody was intraperitoneally administered at a dose of 100 μg/animal once a week. Two weeks later, the large intestines were harvested, and the lengths of the large intestines were measured and compared. Due to DDS administration, the lengths of the large intestines were significantly shortened as compared with the sham group (N=6) ($p<0.01$). However, the anti-human Exon-21 monoclonal antibody (ex21MoAb) administration group showed significant inhibition of the shortening of the length of the large intestine, as compared with the mouse control IgG antibody (mIgG) administration group and the DDS-alone administration group (N=6) ($p<0.05$) (FIG. 6).

Example 10

Figure 7:
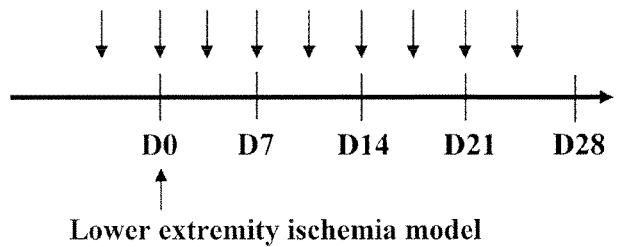
FIG. 7A is a chart showing the timing of the administration of an antibody in Example 10.
FIG. 7B is a chart showing the results of the study on the angiogenesis inhibitory effect of the anti-rat Exon-21 polyclonal antibody in an arteriosclerosis obliterans model in Example 10.
Figure 7:
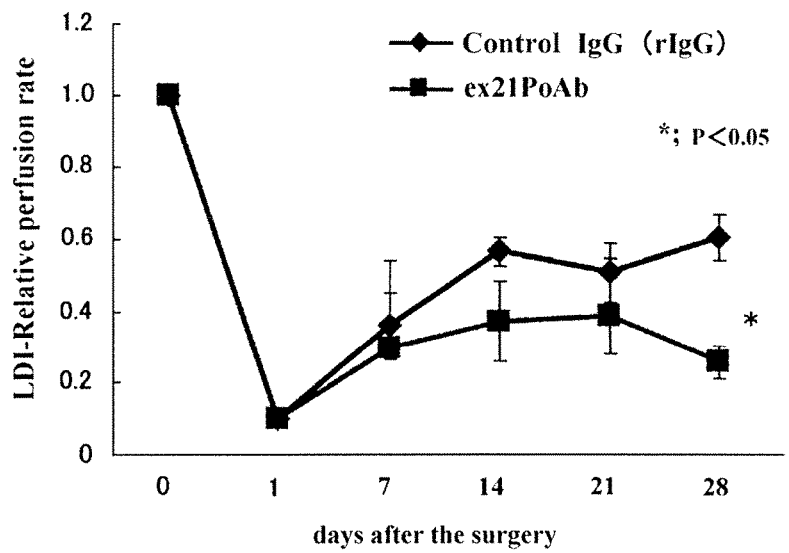
Figure 8:
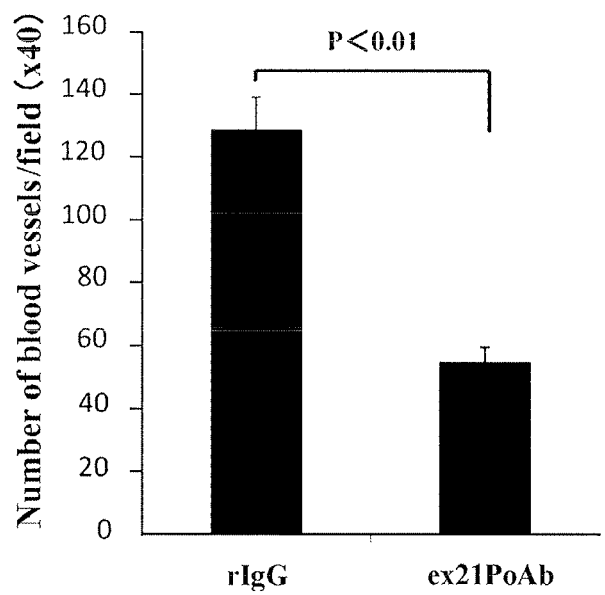
FIG. 8 is a chart showing the results of the study on the angiogenesis inhibitory effect of the anti-rat Exon-21 polyclonal antibody in an arteriosclerosis obliterans model in Example 10.
Figure 9:
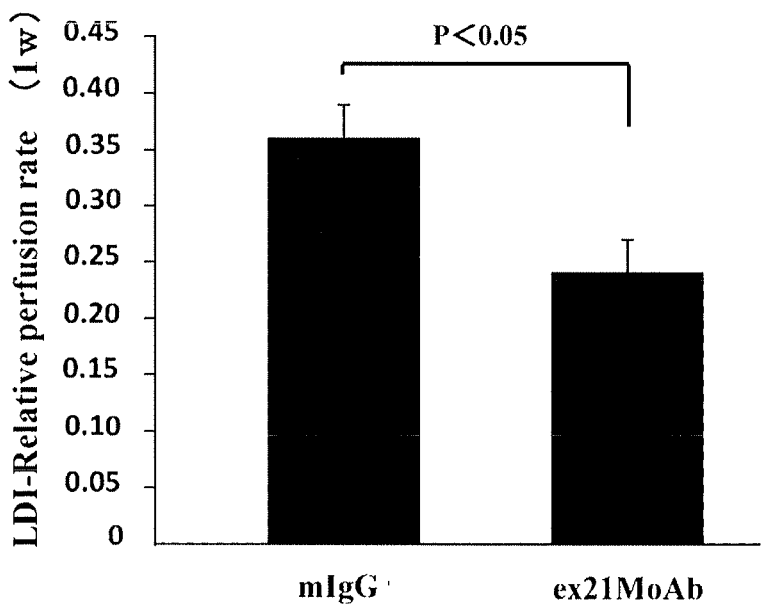
FIG. 9 is a chart showing the results of the study on the angiogenesis inhibitory effect of the anti-human Exon-21 monoclonal antibody in an arteriosclerosis obliterans model in Example 10.

Study of Inhibitory Effect of Anti-rat Exon-21 Polyclonal Antibody on Angiogenesis Using Lower Extremity Ischemia Model The lower extremity femoral artery of C57BL6N mice was ligated to prepare a lower extremity ischemia model. Three days before the ligation, the anti-rat Exon-21 polyclonal antibody (ex21PoAb) or a rabbit control IgG antibody (rIgG) was intraperitoneally administered at a dose of 40 μg/mL (twice a week). Zero day (immediately before the administration), and 1, 7, 14, 21 and 28 days after the administration, the lower extremity blood flow in the unaffected side and the affected side was measured with Laser Doppler Imager (LDI; Moor Instruments). The relative perfusion rate defined as the affected side flow/unaffected side flow was calculated for the evaluation of the lower extremity blood flow, and the groups were compared. The relative perfusion rate 28 days later showed a significant decrease in the lower extremity blood flow in the anti-rat Exon-21 polyclonal antibody (ex21PoAb) administration group as compared with the rabbit control IgG antibody (rIgG) administration group ($p<0.05$) (FIG. 7). The adducent muscles of the mice were harvested, and frozen sections were prepared, immunostained with a CD31 antibody, and subjected to the evaluation of the blood vessels. The number of the blood vessels per unit area was significantly smaller in the anti-rat Exon-21 polyclonal antibody (ex21PoAb) administration group than in the rabbit control IgG antibody (rIgG) administration group, which revealed significant inhibition of angiogenesis ($p<0.01$) (N=6) (FIG. 8). The same set of experiments was performed using the anti-human Exon-21 monoclonal antibody (ex21MoAb). As with the case of the polyclonal antibody, the relative perfusion rate computed with LDI indicated a significant decrease in the blood flow as compared with the mouse control IgG antibody (mIgG) administration group, which revealed inhibition of angiogenesis (FIG. 9).

Example 11

Figure 10:
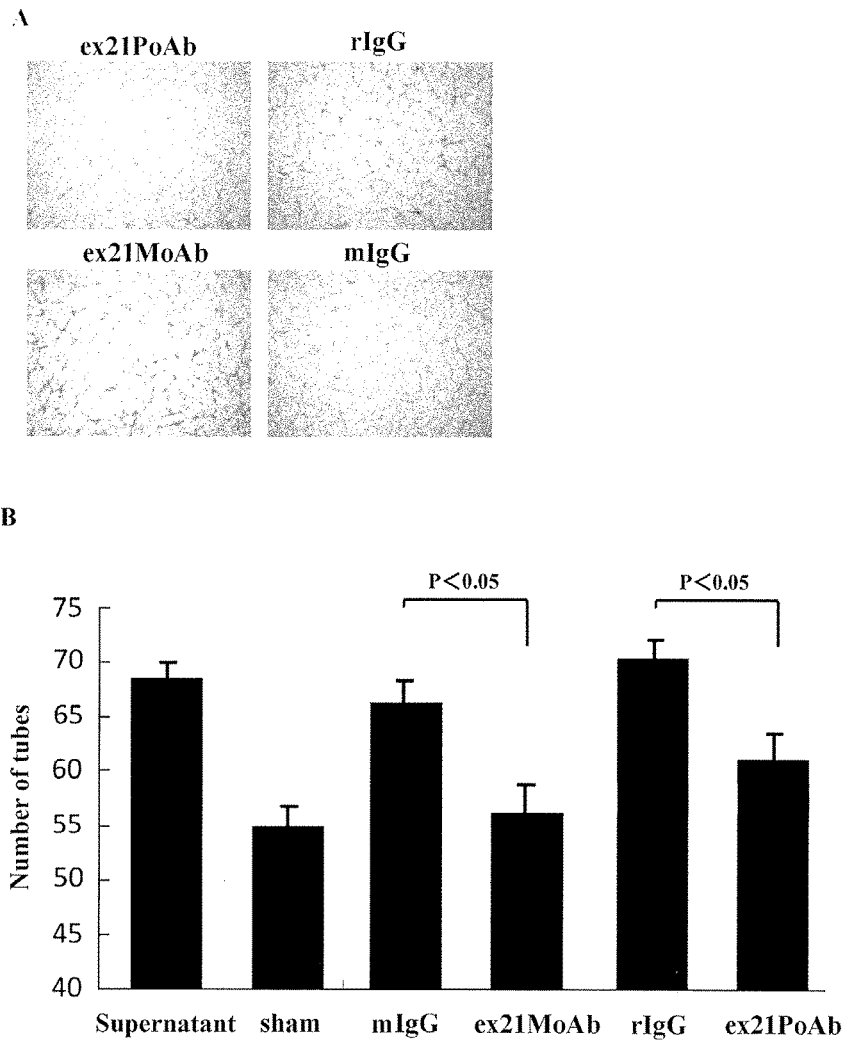
FIGS. 10A and 10B are images and a chart showing the results of the study on the angiogenesis inhibitory effect of the anti-rat Exon-21 polyclonal antibody and the anti-human Exon-21 monoclonal antibody in a Matrigel angiogenesis model using human endothelial cells in Example 11. In the chart, the term "sham" indicates a sham treatment group.
Figure 11:
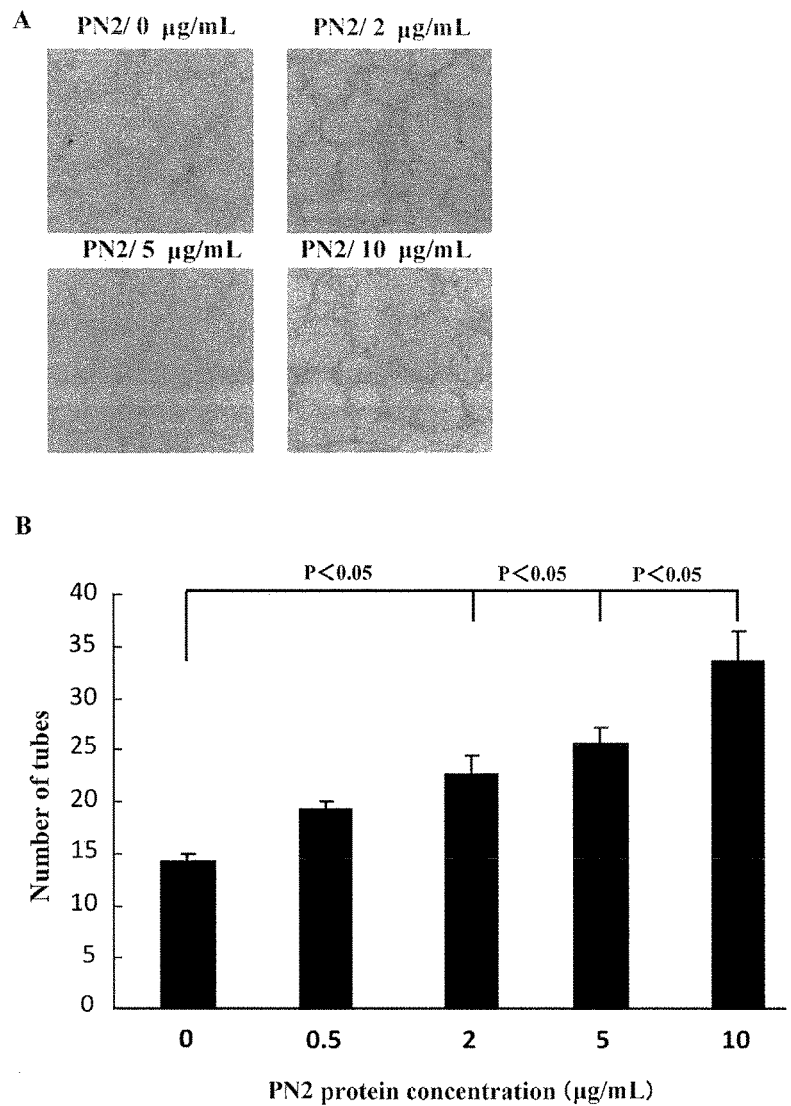
FIGS. 11A and 11B are images and a chart showing the results of the study on the angiogenesis inhibitory effect of the anti-rat Exon-21 polyclonal antibody and the anti-human Exon-21 monoclonal antibody in a Matrigel angiogenesis model using human endothelial cells in Example 11. In the chart, the term "sham" indicates a sham treatment group.

In Vitro Inhibitory Effect of Anti-rat Exon-21 Polyclonal Antibody on Tube Formation The supernatant of 4T1 breast cancer cells was added to Matrigel (BD Bioscience, No. 356231). To this, a mouse control IgG antibody (mIgG), the anti-human Exon-21 monoclonal antibody (ex21MoAb), a rabbit control IgG antibody (rIgG), and the anti-rat Exon-21 polyclonal antibody (ex21PoAb), each at a concentration of $\frac{1}{100}$, were separately added. Each mixture was added to a 96-well plate in an amount of 70 μL/well. The mixtures were incubated for 30 minutes to allow gel formation, and HUVECs (normal human umbilical vein endothelial cells) were seeded at a cell density of $1.5 \times 10^4$ cells/well. The cells were incubated for 5 hours, stained with a crystal violet solution, and photographed under a microscope. The number of tubes was counted. The angiogenic properties of the supernatant of 4T1 breast cancer cells were significantly inhibited by the anti-rat Exon-21 polyclonal antibody and the anti-human Exon-21 monoclonal antibody ($p<0.05$) (FIGS. 10A and 10B). Matrigel to which PN-2 protein in various concentrations was added was processed and evaluated in the same manner as above. The evaluation showed that, at concentrations of 5 μg/mL or more, PN-2 protein significantly induced tube formation in a dose-dependent manner, which indicated the angiogenic properties of PN-2 protein ($p<0.05$) (FIGS. 11A and 11B). The results of the study showed that the anti-Exon-21 antibodies have an angiogenesis inhibitory effect. The results also indicated the angiogenic properties of PN-2 protein.

Example 12

Figure 12:
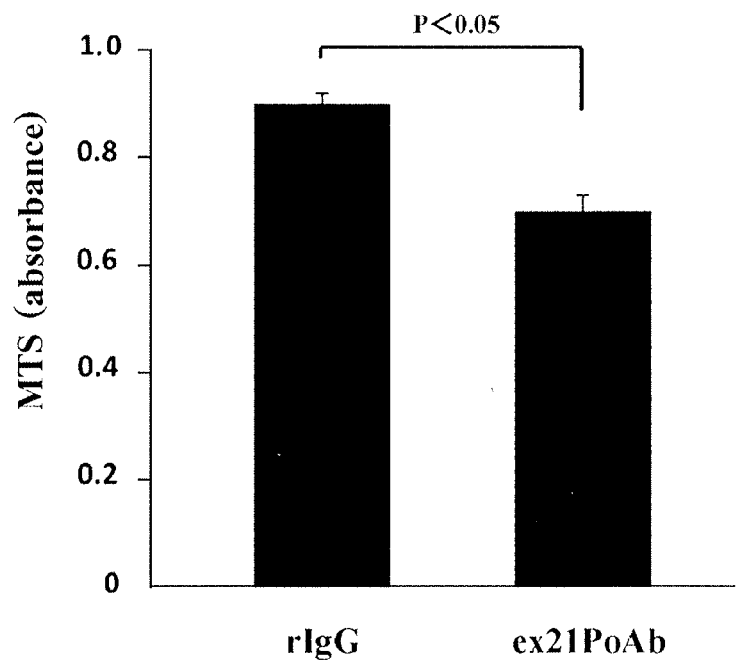
FIG. 12A is a chart showing the results of the study on the cancer cell proliferation inhibitory effect of the anti-rat Exon-21 polyclonal antibody on mouse 4T1 breast cancer cells in Example 12.
FIG. 12B is a chart showing the results of the study on the necrosis induction effect of the anti-human Exon-21 monoclonal antibody on mouse 4T1 breast cancer cells in Example 11.
Figure 12:
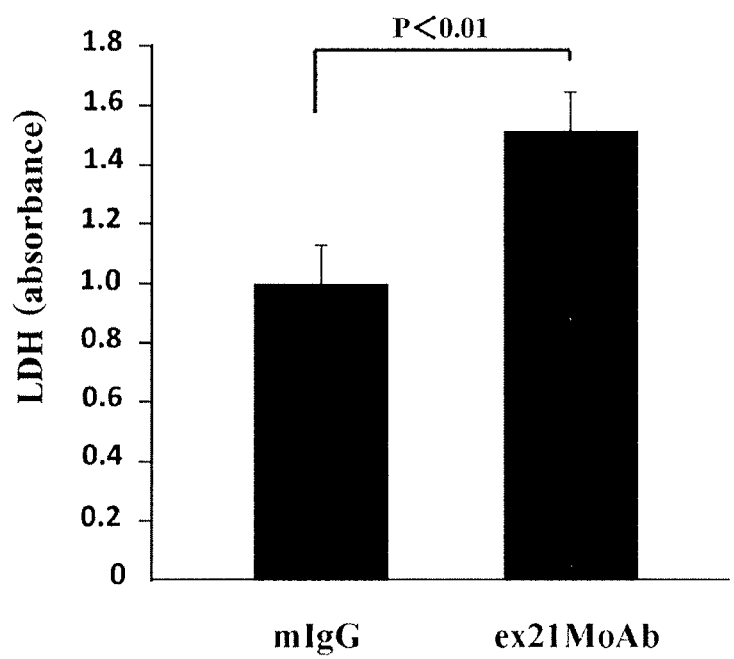

In Vitro Study of Influence of Anti-rat Exon-21 Polyclonal Antibody on Cell Growth Mouse 4T1 breast cancer cells were seeded in DMEM (serum free, PC/SM) in a 96-well cell culture multi-well plate at a density of $10^5$ cells/well and cultured in a 37° C. incubator overnight. After removal of the culture supernatant, to the wells was added DMEM (serum free, PC/SM) medium to which the anti-rat Exon-21 polyclonal antibody (ex21PoAb) or a rabbit control IgG antibody (rIgG) (each at 200 µg/mL) was added at a final concentration of 1 µg/mL. The cells were then cultured overnight. On the following day, the medium in all the wells was replaced with DMEM (10% BSA, PC/SM), and 20 µL of CellTiter Reagent of a cell proliferation assay kit (trade name: CellTiter 96 AQueous One Solution Cell Proliferation Assay kit, Promega) was added to 100 µL of the medium in the wells. The cells were cultured at 37° C. for 1 hour. The staining intensity of the cells was measured with a plate reader (BIO-RAD, Model 680 MICRO PLATE READER) at 490 nm (FIG. 12A). The results revealed that the anti-rat Exon-21 polyclonal antibody (ex21PoAb) exhibited cell growth inhibitory activity at a high concentration as compared with the rabbit control IgG antibody (rIgG) ($p<0.05$).

Another investigation was performed to determine whether the anti-human Exon-21 monoclonal antibody has cytotoxicity against mouse 4T1 breast cancer cells. Mouse F4T1 breast cancer cells were seeded in DMEM (serum free, PC/SM) in a 96-well cell culture multi-well plate at a density of $1\times10^4$ cells/well and cultured in a 37° C. incubator overnight. After removal of the culture supernatant, to the wells was added DMEM (serum free, PC/SM) medium to which the anti-human Exon-21 monoclonal antibody (ex21MoAb) or a mouse control IgG antibody (mIgG) (each at 100 µg/mL) was added at a final concentration of 1 µg/mL. The cells were then cultured for 6 hours. The culture supernatant was collected and lactate dehydrogenase (LDH) contained in the supernatant was measured by ELISA. For the measurement, a cytotoxicity assay kit (trade name: LDH Cytotoxicity Detection Kit, Takara Bio, Inc.) was used. LDH is an enzyme present in the cytoplasm and usually does not permeate through the cell membrane. When the cell membrane is damaged, LDH is released outside the cell, i.e., into the medium. LDH, therefore, can serve as an indicator of cytotoxicity. The supernatant was subjected to measurement with a plate reader (BIO-RAD, Model 680 MICRO PLATE READER) at 490 nm. The results revealed that the anti-human Exon-21 monoclonal antibody (ex21MoAb) exhibited significant cell growth inhibitory activity at a high concentration as compared with the mouse control IgG antibody (mIgG) ($P<0.01$) (FIG. 12B).

Example 13

Figure 13:
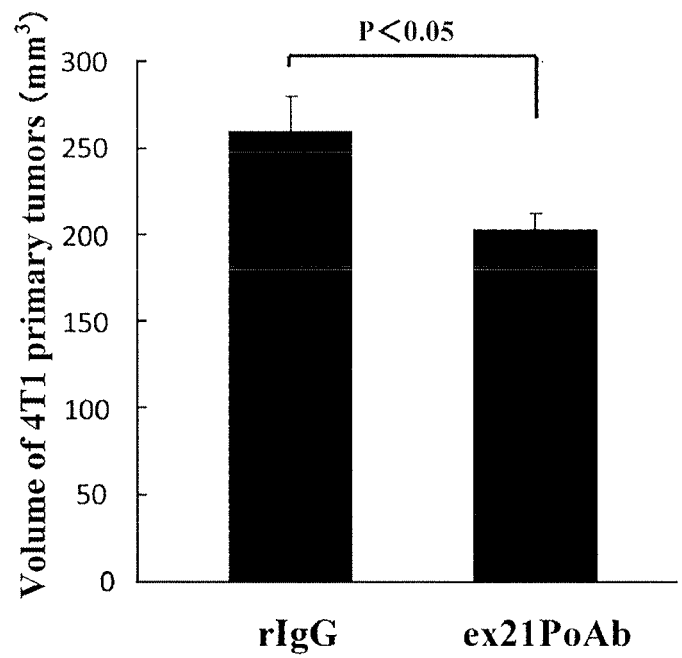
FIG. 13A is a chart showing the results of the study on the effect of the anti-rat Exon-21 polyclonal antibody using lung metastasis model mice of mouse 4T1 breast cancer cells in Example 13 (injection of mouse 4T1 breast cancer cells, followed by measurement of the volume of the primary tumors in the lower extremities three weeks after the injection).
FIG. 13B is a chart showing the results of the study on the effect of the anti-rat Exon-21 polyclonal antibody using lung metastasis model mice of mouse 4T1 breast cancer cells in Example 13 (injection of mouse 4T1 breast cancer cells, followed by the counting of metastatic colonies five weeks after the injection).
Figure 13:
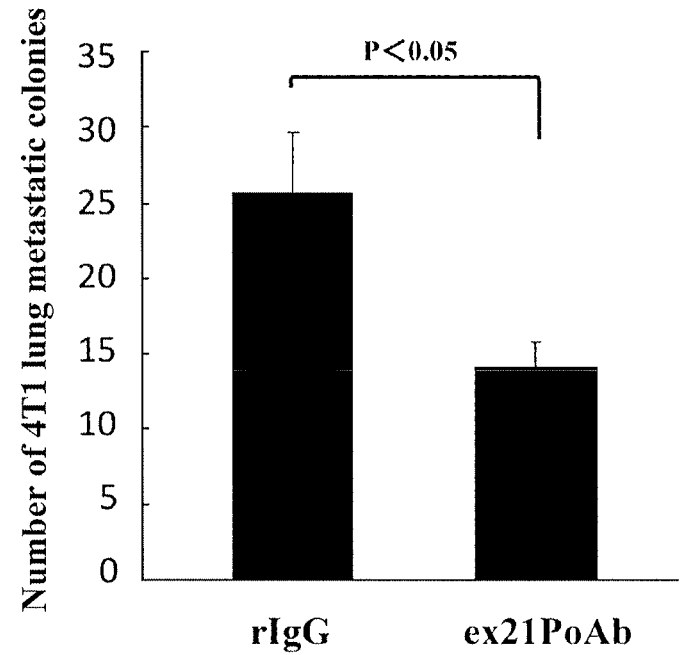
Figure 14:
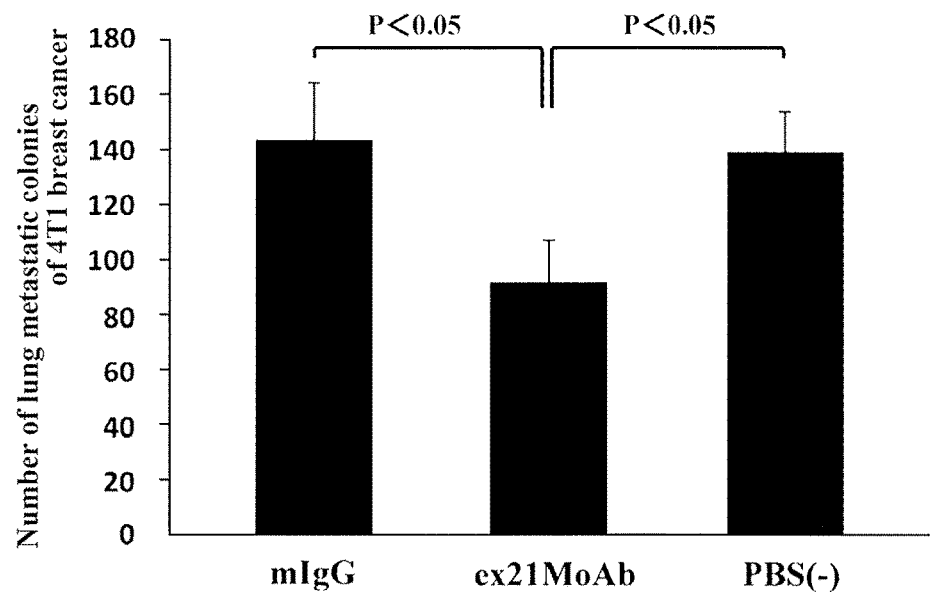
FIG. 14 is a chart showing the results of the study on the effect of the anti-human Exon-21 monoclonal antibody using lung metastasis model mice of mouse 4T1 breast cancer cells in Example 13 (injection of mouse 4T1 breast cancer cells, followed by the counting of metastatic colonies five weeks after the injection).

Study of Effect of Anti-rat Exon-21 Polyclonal Antibody Using Lung Metastasis Model Mice of Mouse 4T1 Breast Cancer Cells Mouse 4T1 cells (ATCC) were seeded on 10 cm Tissue Culture Dishes (Greiner) containing RPMI 1640 (Gibco) containing 10% bovine serum albumin (FBS) (Biowest) and Penicillin-streptomycin Mixed solution (Nacalai Tesque), and the cells were cultured in a 37° C. incubator for 24 hours. The culture supernatant was removed, and the cells were washed with PBS and then treated with trypsin/EDTA. The floating cells were collected and centrifuged at 1,500 rpm for 3 minutes. Subsequently, $1.5\times10^5$ cells were passaged and cultured in a 37° C. incubator for 72 hours. The cells in the logarithmic growth phase were suspended in 100 µL of PBS so as to be $1\times10^6$ cells/animal. The prepared cells were injected into the foot pad of female BALB/c mice at 8 weeks of age using an insulin syringe equipped with an injection needle, 29 G Myjector (TERMO), to establish lung metastasis model mice. To the model mice, the anti-rat Exon-21 polyclonal antibody (ex21PoAb) or a rabbit control IgG antibody (rIgG) was intraperitoneally administered at 100 µg/animal per week using an insulin syringe equipped with an injection needle, 29 G Myjector. For the experiment using the anti-rat Exon-21 polyclonal antibody (ex21PoAb) (1 mg/mL), the cell injection was performed simultaneously with the antibody administration, and one week after and two weeks after the cell injection, further antibody administrations were performed. The rabbit control IgG antibody (rIgG) used was Normal Rabbit IgG (R&D Systems). After the cell injection, the diameter of the swelling lesions in the lower extremities were measured with a caliper to evaluate the volume of the primary tumors. The evaluation was performed in accordance with Dethlefsen L A. et al. J. Natl. Cancer Inst., 40, 389 (1968), using the formula: (length of foot sole)×(width of foot sole)^2/2. The mice were dissected three weeks after the cell injection, and body weight measurement, an examination of the presence or absence of lung metastasis from the primary tumors, and the counting of the lung metastatic colonies were performed. The obtained data were analyzed by Student's t-test. The volume of the primary tumors in the lower extremities three weeks after the cell injection was significantly reduced by the administration of the anti-rat Exon-21 polyclonal antibody (ex21PoAb) ($p<0.05$) (FIG. 13A). A comparison of the number of the lung metastatic colonies five weeks after the cell injection revealed significant reduction in the number of the colonies by the administration of the anti-rat Exon-21 polyclonal antibody (ex21PoAb) ($P<0.05$) (FIG. 13B). The same set of experiments was performed using the anti-human Exon-21 monoclonal antibody (ex21MoAb). As with the case of the polyclonal antibody, significant reduction in the number of the lung metastatic colonies was observed, as compared with a mouse control IgG antibody (mIgG) administration group and with a PBS (−) administration group (FIG. 14). The results revealed the inhibitory effect of the anti-Exon-21 antibodies on the primary tumors and metastatic foci of 4T1 breast cancer cells.

Example 14

Study of Effect of Anti-rat Exon-21 Polyclonal Antibody Using Lung Metastasis Model Mice of Mouse B16F10 Melanoma Cells Mouse B16F10 melanoma cells (mouse melanoma cell line B16F10) were cultured in a 37° C. incubator, washed with PBS, and treated with trypsin/EDTA. The floating cells were collected and centrifuged at 1,500 rpm for 3 minutes. The collected cells were suspended in 100 µL of PBS so as to be $5\times10^5$ cells/animal. The prepared cells were injected into the foot pad of male C57BL/6N mice at 8 weeks of age using an insulin syringe equipped with an injection needle, 29 G Myjector (TERMO), to establish lung metastasis model mice. To the model mice, the anti-rat Exon-21 polyclonal antibody (ex21PoAb) or a rabbit control IgG antibody (rIgG) was administered at 100 µg/animal per week using an insulin syringe equipped with an injection needle, 29 G Myjector. The control used was Normal Rabbit IgG (R&D Systems).

Figure 15:
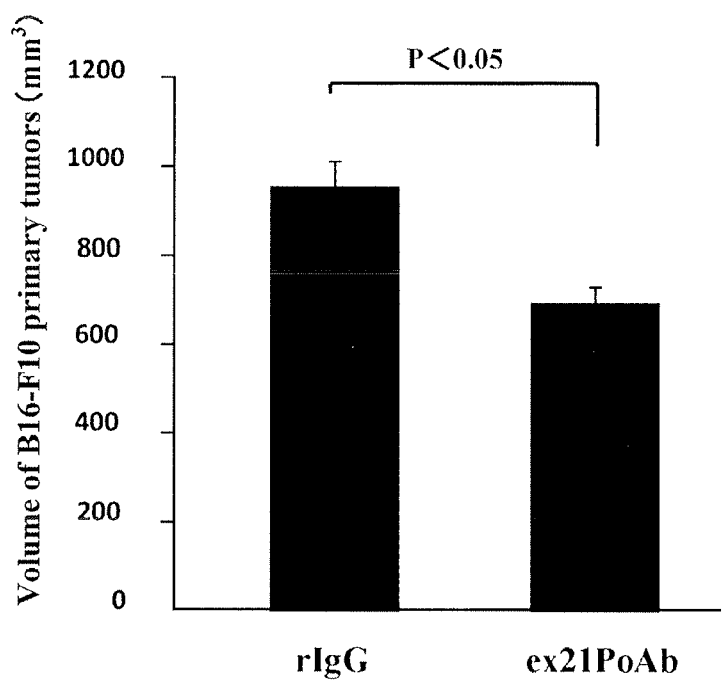
FIG. 15A is a chart showing the results of the study on the effect of the anti-rat Exon-21 polyclonal antibody using lung metastasis model mice of mouse melanoma B16-F10 cells in Example 14 (injection of mouse melanoma cells, followed by measurement of the volume of the primary tumors three weeks after the injection).
FIG. 15B is a chart showing the results of the study on the effect of the anti-rat Exon-21 polyclonal antibody using lung metastasis model mice of mouse melanoma B16-F10 cells in Example 14 (injection of mouse melanoma cells, followed by the counting of metastatic colonies five weeks after the injection).
Figure 15:
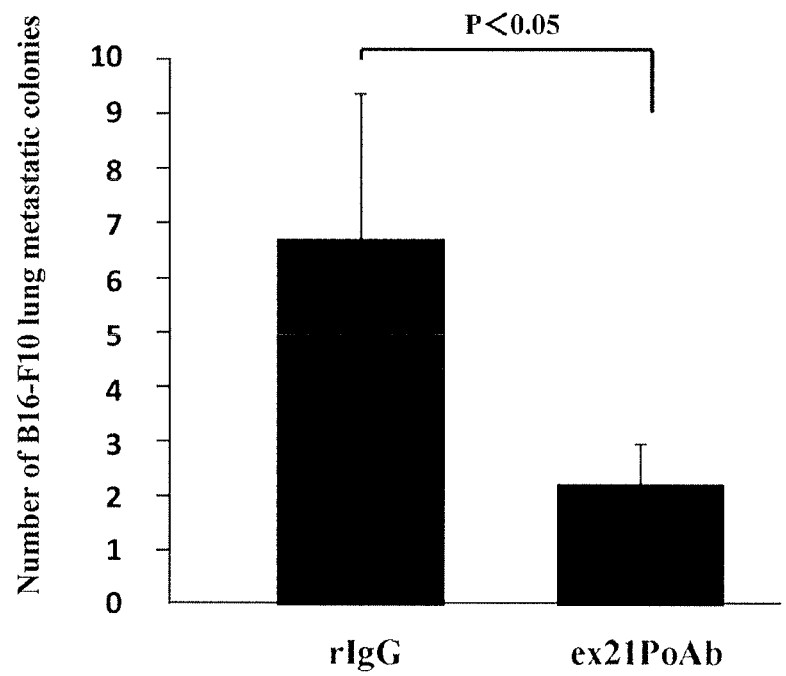

To reproduce the conditions close to the clinical situation, the administration of the anti-rat Exon-21 polyclonal antibody (ex21PoAb) (1 mg/mL) or a rabbit control IgG antibody (rIgG) (1 mg/mL) as a control at 100 µg/animal per week was performed one week after the injection of the mouse B16F10 melanoma cells. The primary tumors were measured with a caliper to evaluate the volume of the primary tumors. The evaluation was performed in accordance with Dethlefsen L A. et al. J. Natl. Cancer Inst., 40, 389 (1968), using the formula: (length of foot sole)×(width of foot sole)^2/2. Three weeks after the cell injection, the administration of the anti-rat Exon-21 polyclonal antibody significantly inhibited the growth of the primary tumors as compared the administration of the rabbit control IgG antibody (rIgG) ($p<0.05$) (FIG. 15A). The number of lung metastatic colonies was counted by visual inspection and compared. The results showed that, five weeks after the cell injection, the administration of the anti-rat Exon-21 polyclonal antibody (ex21PoAb) significantly inhibited lung metastasis as compared with the administration of the rabbit control IgG antibody (rIgG) ($p<0.05$) (FIG. 15B). The data analysis of the number of the lung metastatic colonies was performed by Mann-Whitney test.

Example 15

Study of Effect of Anti-human Exon-21 Monoclonal Antibody Using Aneurysm Model Mice The study was conducted using aged (6 months or more) ApoE knockout mice. Angiotensin II was dissolved in physiological saline. The angiotensin II (Sigma Aldrich, A9525) solution was loaded into an osmotic pump for continuous administration (Alzet, Muromachi Kikai Co., Ltd., Model: 2004). The dosage was set at 1,000 ng/kg·day. The adjusted osmotic pump was primed with physiological saline for a night and day. Vaporized isoflurane was administered to the mice by inhalation at a concentration of 2% and a flow rate of 1 L/min. After sufficient anesthesia was achieved, the mice were maintained in a prone position. The neck skin was sterilized with a 70% ethanol solution and a small incision was made. From the incision site, scissors were inserted under the mouse skin, and the skin was peeled off. A space for placing the pump was created, and the osmotic pump was implanted under the mouse skin. After implantation, the incision was closed with staples for small animal surgery (Fine Science Tools, Muromachi Kikai Co., Ltd., Model: 12040-01).

Figure 16:
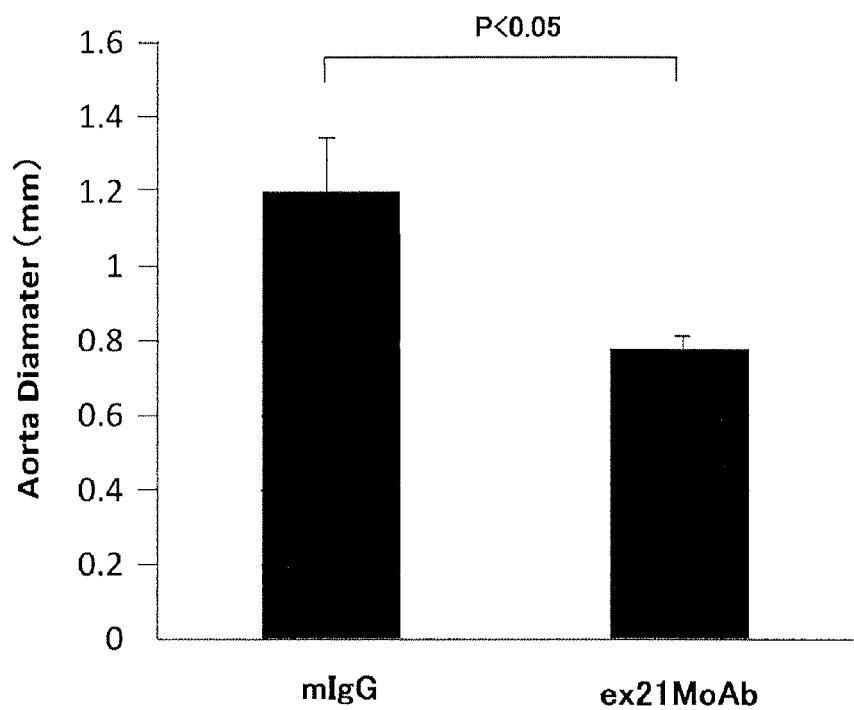
FIG. 16 is a chart showing the results of the study on the inhibitory effect of the anti-human Exon-21 monoclonal antibody on the expansion of the diameter of the aorta in an aneurysm model in Example 15.

A mouse control IgG antibody (mIgG, 100 μg/animal) or the anti-human Exon-21 monoclonal antibody (ex21MoAb; 100 μg/animal) was intraperitoneally administered once a week, starting from zero week. Four weeks later, the diameter of the aorta was measured with an ultrasound scanner (Toshiba Medical Systems Corporation, Aplio XV). The results revealed that the anti-human Exon-21 monoclonal antibody (ex21MoAb) significantly inhibited the expansion of the diameter of the aorta (FIG. 16).

INDUSTRIAL APPLICABILITY

An antibody against a periostin isoform having cell adhesion activity can be used to prevent and treat inflammation-associated diseases including cancers. The antibody can also be used for the measurement of the amount of such a periostin isoform in a patient sample to determine the presence or absence of a cancer and the progression of the disease conditions.

ACCESSION NO.
Identification of the Microorganism
    Identification Reference: KS-0259#8, 080611 Kohjin Bio
    Accession No.: NITE BP-01546
Deposit Date
    Feb. 26, 2013
International Depositary Authority
    Name: Incorporated Administrative Agency, National Institute of Technology and Evaluation, Patent Microorganisms Depositary
    Address: Room 122, 2-5-8, Kazusakamatari, Kisarazu-shi, Chiba 292-0818 JAPAN

The invention claimed is:

1. A method for inhibiting a periostin isoform having cell adhesion activity which comprises administering to a patient a therapeutically effective amount of an antibody binding to one or more peptides selected from the group consisting of a peptide consisting of an amino acid sequence of SEQ ID NO: 6, a peptide consisting of an amino acid sequence of SEQ ID NO: 17 and a peptide consisting of an amino acid sequence of SEQ ID NO: 18, wherein the antibody is produced by a hybridoma cell line designated as NITE BP-01546.

2. The method of claim 1, wherein the antibody is a fragment of a monoclonal antibody.

3. The method of claim 1, wherein the antibody is an antibody derivative comprising a protein or low molecular weight drug linked to the antibody.

4. A method for treating a disease during which periostin is expressed, the method comprising administering, to a patient, a therapeutically effective amount of an antibody binding to one or more peptides selected from the group consisting of a peptide consisting of an amino acid sequence of SEQ ID NO: 6, a peptide consisting of an amino acid sequence of SEQ ID NO: 17 and a peptide consisting of an amino acid sequence of SEQ ID NO: 18, wherein the antibody is produced by a hybridoma cell line designated as NITE BP-01546.

5. The method of claim 4, wherein the antibody is a fragment of a monoclonal antibody.

6. The method of claim 4, wherein the antibody is an antibody derivative comprising a protein or low molecular weight drug linked to the antibody.

7. The method according to claim 4, wherein the disease during which periostin is expressed is restenosis primarily caused by vascular intimal hyperplasia, a cancer, a disease accompanied by angiogenesis, or aneurysm.

8. The method according to claim 5, wherein the disease during which periostin is expressed is restenosis primarily caused by vascular intimal hyperplasia, a cancer, a disease accompanied by angiogenesis, or aneurysm.

9. The method according to claim 6, wherein the disease during which periostin is expressed is restenosis primarily caused by vascular intimal hyperplasia, a cancer, a disease accompanied by angiogenesis, or aneurysm.

10. The method of claim 4, wherein the disease during which periostin is expressed is selected from the group consisting of multiple sclerosis, chronic inflammatory demyelinating polyneuropathy, periodontosis, atopic dermatitis, asthma, diabetic retinopathy, arteriosclerosis, inflammatory enterocolitis, breast cancer, lung cancer, melanoma, aneurysm, and osteoarthritis cartilage.

11. The method of claim 4, wherein the disease during which periostin is expressed is selected from the group consisting of chronic inflammatory demyelinating polyneuropathy, periodontosis, diabetic retinopathy, arteriosclerosis, inflammatory enterocolitis, breast cancer, lung cancer, melanoma, and aneurysm.

* * * * *

SEQUENCE LISTING

```
<160> NUMBER OF SEQ ID NOS: 31

<210> SEQ ID NO 1
<211> LENGTH: 838
<212> TYPE: PRT
<213> ORGANISM: Rattus sp.

<400> SEQUENCE: 1

Met Val Pro Leu Leu Pro Leu Ser Ala Leu Leu Leu Leu Phe Leu Cys
1               5                   10                  15

Asp Val Asp Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Tyr Phe Ser Ser Cys Lys Asn
    50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110
```

-continued

Thr Thr Thr Gln His Tyr Ser Asp Val Ser Lys Leu Arg Glu Ile
        115                 120                 125
Glu Gly Lys Gly Ser Tyr Thr Tyr Phe Ala Pro Ser Asn Glu Ala Trp
130                 135                 140
Asp Asn Leu Asp Ser Asp Ile Arg Arg Gly Leu Glu Asn Asn Val Asn
145                 150                 155                 160
Val Glu Leu Leu Asn Ala Leu His Ser His Met Val Asn Lys Arg Met
                165                 170                 175
Leu Thr Lys Asp Leu Lys His Gly Met Val Ile Pro Ser Met Tyr Asn
            180                 185                 190
Asn Leu Gly Leu Phe Ile Asn His Tyr Pro Asn Gly Val Val Thr Val
        195                 200                 205
Asn Cys Ala Arg Val Ile His Gly Asn Gln Ile Ala Thr Asn Gly Val
210                 215                 220
Val His Val Ile Asp Arg Val Leu Thr Gln Ile Gly Thr Ser Ile Gln
225                 230                 235                 240
Asp Phe Ile Glu Ala Glu Asp Glu Leu Ser Ser Phe Arg Ala Ala Ala
                245                 250                 255
Ile Thr Ser Asp Leu Leu Glu Ser Leu Gly Arg Asp Gly His Phe Thr
            260                 265                 270
Leu Phe Ala Pro Thr Asn Glu Ala Phe Glu Lys Leu Pro Arg Gly Val
        275                 280                 285
Leu Glu Arg Ile Met Gly Asp Lys Val Ala Ser Glu Ala Leu Met Lys
290                 295                 300
Tyr His Ile Leu Asn Thr Leu Gln Cys Ser Glu Ala Ile Thr Gly Gly
305                 310                 315                 320
Ala Val Phe Glu Thr Met Glu Gly Asn Thr Ile Glu Ile Gly Cys Glu
                325                 330                 335
Gly Asp Ser Ile Ser Ile Asn Gly Ile Lys Met Val Asn Lys Lys Asp
            340                 345                 350
Ile Val Thr Lys Asn Gly Val Ile His Leu Ile Asp Glu Val Leu Ile
        355                 360                 365
Pro Asp Ser Ala Lys Gln Val Ile Glu Leu Ala Gly Lys Gln Gln Thr
370                 375                 380
Thr Phe Thr Asp Leu Val Ala Gln Leu Gly Leu Ala Ser Ser Leu Lys
385                 390                 395                 400
Pro Asp Gly Glu Tyr Thr Leu Leu Ala Pro Val Asn Asn Ala Phe Ser
                405                 410                 415
Asp Asp Thr Leu Ser Met Asp Gln Arg Leu Leu Lys Leu Ile Leu Gln
            420                 425                 430
Asn His Ile Leu Lys Val Lys Val Gly Leu Ser Asp Leu Tyr Asn Gly
        435                 440                 445
Gln Ile Leu Glu Thr Ile Gly Gly Lys Gln Leu Arg Val Phe Val Tyr
450                 455                 460
Arg Thr Ala Ile Cys Ile Glu Asn Ser Cys Met Val Arg Gly Ser Lys
465                 470                 475                 480
Gln Gly Arg Asn Gly Ala Ile His Ile Phe Arg Glu Ile Ile Gln Pro
                485                 490                 495
Ala Glu Lys Ser Leu His Glu Lys Leu Arg Gln Asp Lys Arg Phe Ser
            500                 505                 510
Ile Phe Leu Ser Leu Leu Glu Ala Ala Asp Leu Lys Asp Leu Leu Thr
        515                 520                 525
Gln Pro Gly Asp Trp Thr Leu Phe Ala Pro Thr Asn Asp Ala Phe Lys

```
         530                 535                 540
Gly Met Thr Asn Glu Glu Arg Glu Ile Leu Ile Gly Asp Lys Asn Ala
545                 550                 555                 560

Leu Gln Asn Ile Ile Leu Tyr His Leu Thr Pro Gly Val Tyr Ile Gly
                565                 570                 575

Lys Gly Phe Glu Pro Gly Val Thr Asn Ile Leu Lys Thr Thr Gln Gly
                580                 585                 590

Ser Lys Ile Tyr Val Lys Gly Val Asn Glu Thr Leu Leu Val Asn Glu
            595                 600                 605

Leu Lys Ser Lys Glu Ser Asp Ile Met Thr Thr Asn Gly Val Ile His
        610                 615                 620

Val Val Asp Lys Leu Leu Tyr Pro Ala Asp Ile Pro Val Gly Asn Asp
625                 630                 635                 640

Gln Leu Leu Glu Leu Leu Asn Lys Leu Ile Lys Tyr Ile Gln Ile Lys
                645                 650                 655

Phe Val Arg Gly Ser Thr Phe Lys Glu Ile Pro Met Thr Val Tyr Thr
                660                 665                 670

Thr Lys Ile Ile Thr Lys Leu Val Glu Pro Lys Ile Lys Val Ile Gln
            675                 680                 685

Gly Ser Leu Gln Pro Ile Ile Lys Thr Glu Gly Pro Ala Met Thr Lys
        690                 695                 700

Ile His Ile Glu Gly Glu Pro Asp Phe Arg Leu Ile Lys Glu Gly Glu
705                 710                 715                 720

Thr Val Thr Glu Val Ile His Gly Glu Pro Val Ile Lys Lys Tyr Thr
                725                 730                 735

Lys Ile Ile Asp Gly Val Pro Val Glu Ile Thr Glu Lys Glu Thr Arg
            740                 745                 750

Glu Glu Arg Ile Ile Thr Gly Pro Glu Ile Lys Tyr Thr Arg Ile Ser
        755                 760                 765

Thr Gly Gly Gly Glu Thr Glu Glu Thr Leu Gln Lys Phe Leu Gln Lys
770                 775                 780

Glu Val Ser Lys Val Thr Lys Phe Ile Glu Gly Gly Asp Gly His Leu
785                 790                 795                 800

Phe Glu Asp Glu Ala Ile Lys Arg Leu Leu Gln Gly Asp Thr Pro Ala
                805                 810                 815

Lys Lys Ile Gln Ala Asn Lys Arg Val Gln Gly Ser Arg Arg Arg Ser
            820                 825                 830

Arg Glu Gly Arg Ser Gln
        835

<210> SEQ ID NO 2
<211> LENGTH: 2517
<212> TYPE: DNA
<213> ORGANISM: Rattus sp.

<400> SEQUENCE: 2
atggttcctc tcctgccctt atctgctctg ctgctgctgt tcctgtgtga cgttgacccc     60
gcaaatgcca acagttacta tgacaaggtc ctagctcaca gccgcatcag gggtcgggat    120
cagggcccaa atgtctgtgc cctccagcag attctgggca ccaaaaagaa atacttcagc    180
tcctgtaaga actggtatca aggtgctatc tgcgggaaga aaccactgt gctatatgaa    240 tgctgccccg gctatatgag aatggaaggg atgaaaggct gcccagcagt gatgcccatt    300
gaccatgttt atggcacgct gggcatcgtg ggagccacga ccactcaaca ctattctgat    360
```

```
gtctcgaagc tcagggaaga gattgaagga aaagggtcct acacatactt cgcgccgagt       420
aacgaagctt gggacaacct ggattccgac atccgcagag gactagagaa caatgtcaat       480
gttgagttac tgaacgcttt acacagccac atggttaata agagaatgct aaccaaggac       540
ctgaaacacg gcatggttat tccttcaatg tacaacaatc tggggctttt tatcaatcat       600
tatcccaatg gggttgtcac tgtgaactgt gctcgagtaa tccacgggaa ccagattgcc       660
acaaatggtg ttgtccatgt catcgaccgt gtcctgacac aaattggcac tccatccaa        720 gacttcattg aagcagaaga tgagctttca tcattcagag cggctgccat cacttctgac       780
cttttggagt cccttggaag agacggtcac ttcacactct ttgctcccac caatgaggct       840
ttcgagaaac tcccacgagg agtcctagaa aggatcatgg gagacaaagt ggcttctgaa       900
gctctcatga agtaccacat cctgaatacc ctccagtgct ctgaggctat cacaggagga       960
gcggtgtttg agaccatgga aggaaacact attgaaatag ggtgtgaggg agacagcatc      1020
tccattaacg gaatcaagat ggtgaacaag aaagacattg tgacgaagaa tggtgtcatc      1080
cacctgattg atgaagtcct cattcctgat tctgctaaac aagttattga gctggctgga      1140
aaacagcaaa ccactttcac ggacctggta gcccagttag ggttggcgtc ttctctgaag      1200
ccggatggag agtacacgct gttagcgcct gtgaacaatg cgttctctga tgacactctg      1260
agcatggacc agcgccttct taagctaatt ctgcaaaatc acatattgaa agtaaaagtc      1320
ggccttagtg atctctacaa tggacagatt ctggagacca ttggaggcaa acaactccgt      1380
gtcttcgtgt atcggacggc tatctgcata gaaaactcat gcatggtgag aggaagcaag      1440
caggggagga acggtgccat tcacatattc gagagatca tccaaccggc ggagaagtcc      1500
ctgcacgaaa aactgcgcca agataagcgc ttcagcatct tcctcagcct cctcgaagct      1560
gcagatctga aagatcttct gacacagccc ggagattgga ccttgtttgc accaaccaat      1620
gatgccttca agggaatgac taatgaagaa agggagattc tgattgggga taaaaatgct      1680
ctccaaaaca tcattctta ccacctgacc ccagggggttt atattggaaa gggatttgaa      1740
cccggagtca ccaacatcct gaagaccaca cagggaagca aaatctatgt gaaaggagtc      1800
aatgagacgc ttttggtgaa tgagttgaag tccaaagaat ctgacatcat gacaacaaac      1860
ggcgtcattc acgttgtgga caaactcctc tatccagcag acattccggt tggaaatgat      1920
cagctcttgg aattactgaa caaactgata aaatacatcc aaattaagtt cgttcgtggc      1980
agcaccttca agaaatccc catgactgtc tatacaacta aaattataac caaactcgtg      2040
gaaccaaaaa ttaaagtcat tcaaggcagt cttcagccta ttatcaaaac agaaggacct      2100
gcaatgacga agatccacat tgaaggcgag cctgacttca ggctgattaa agaaggtgaa      2160
acagtgacag aagtgatcca cggagaacca gtcattaaaa agtacaccaa aatcatagac      2220
ggggttcctg ttgaaataac tgaaaaagag acccgggaag aacgcatcat cacaggtcct      2280
gagataaaat acactaggat ttccacagga ggtgggggaaa cagaagagac cctgcagaaa      2340
ttcttgcaaa aagaggtctc caaggtcaca aagttcattg aaggtggcga tggtcactta      2400
tttgaagatg aggcgattaa aagactgctt cagggagaca cacctgcaaa gaagatacaa      2460
gccaacaaaa gggttcaagg gtctagaagg cgatcaagag aaggccgttc tcagtga       2517
```

<210> SEQ ID NO 3
<211> LENGTH: 811
<212> TYPE: PRT
<213> ORGANISM: Rattus sp.

<400> SEQUENCE: 3

-continued

```
Met Val Pro Leu Leu Pro Leu Ser Ala Leu Leu Leu Phe Leu Cys
1               5                   10                  15

Asp Val Asp Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
            35                  40                  45

Gln Gln Ile Leu Gly Thr Lys Lys Tyr Phe Ser Ser Cys Lys Asn
50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
            85                  90                  95

Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
            115                 120                 125

Glu Gly Lys Gly Ser Tyr Thr Tyr Phe Ala Pro Ser Asn Glu Ala Trp
            130                 135                 140

Asp Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
            165                 170                 175

Leu Thr Lys Asp Leu Lys His Gly Met Val Ile Pro Ser Met Tyr Asn
            180                 185                 190

Asn Leu Gly Leu Phe Ile Asn His Tyr Pro Asn Gly Val Val Thr Val
            195                 200                 205

Asn Cys Ala Arg Val Ile His Gly Asn Gln Ile Ala Thr Asn Gly Val
            210                 215                 220

Val His Val Ile Asp Arg Val Leu Thr Gln Ile Gly Thr Ser Ile Gln
225                 230                 235                 240

Asp Phe Ile Glu Ala Glu Asp Glu Leu Ser Ser Phe Arg Ala Ala Ala
            245                 250                 255

Ile Thr Ser Asp Leu Leu Glu Ser Leu Gly Arg Asp Gly His Phe Thr
            260                 265                 270

Leu Phe Ala Pro Thr Asn Glu Ala Phe Glu Lys Leu Pro Arg Gly Val
            275                 280                 285

Leu Glu Arg Ile Met Gly Asp Lys Val Ala Ser Glu Ala Leu Met Lys
            290                 295                 300

Tyr His Ile Leu Asn Thr Leu Gln Cys Ser Glu Ala Ile Thr Gly Gly
305                 310                 315                 320

Ala Val Phe Glu Thr Met Glu Gly Asn Thr Ile Glu Ile Gly Cys Glu
            325                 330                 335

Gly Asp Ser Ile Ser Ile Asn Gly Ile Lys Met Val Asn Lys Lys Asp
            340                 345                 350

Ile Val Thr Lys Asn Gly Val Ile His Leu Ile Asp Glu Val Leu Ile
            355                 360                 365

Pro Asp Ser Ala Lys Gln Val Ile Glu Leu Ala Gly Lys Gln Gln Thr
            370                 375                 380

Thr Phe Thr Asp Leu Val Ala Gln Leu Gly Leu Ala Ser Ser Leu Lys
385                 390                 395                 400

Pro Asp Gly Glu Tyr Thr Leu Leu Ala Pro Val Asn Asn Ala Phe Ser
            405                 410                 415
```

-continued

Asp Asp Thr Leu Ser Met Asp Gln Arg Leu Leu Lys Leu Ile Leu Gln
            420                 425                 430

Asn His Ile Leu Lys Val Lys Val Gly Leu Ser Asp Leu Tyr Asn Gly
            435                 440                 445

Gln Ile Leu Glu Thr Ile Gly Gly Lys Gln Leu Arg Val Phe Val Tyr
            450                 455                 460

Arg Thr Ala Ile Cys Ile Glu Asn Ser Cys Met Val Arg Gly Ser Lys
465                 470                 475                 480

Gln Gly Arg Asn Gly Ala Ile His Ile Phe Arg Glu Ile Ile Gln Pro
                    485                 490                 495

Ala Glu Lys Ser Leu His Glu Lys Leu Arg Gln Asp Lys Arg Phe Ser
            500                 505                 510

Ile Phe Leu Ser Leu Leu Glu Ala Ala Asp Leu Lys Asp Leu Leu Thr
            515                 520                 525

Gln Pro Gly Asp Trp Thr Leu Phe Ala Pro Thr Asn Asp Ala Phe Lys
            530                 535                 540

Gly Met Thr Asn Glu Glu Arg Glu Ile Leu Ile Gly Asp Lys Asn Ala
545                 550                 555                 560

Leu Gln Asn Ile Ile Leu Tyr His Leu Thr Pro Gly Val Tyr Ile Gly
                    565                 570                 575

Lys Gly Phe Glu Pro Gly Val Thr Asn Ile Leu Lys Thr Thr Gln Gly
            580                 585                 590

Ser Lys Ile Tyr Val Lys Gly Val Asn Glu Thr Leu Leu Val Asn Glu
            595                 600                 605

Leu Lys Ser Lys Glu Ser Asp Ile Met Thr Thr Asn Gly Val Ile His
            610                 615                 620

Val Val Asp Lys Leu Leu Tyr Pro Ala Asp Ile Pro Val Gly Asn Asp
625                 630                 635                 640

Gln Leu Leu Glu Leu Leu Asn Lys Leu Ile Lys Tyr Ile Gln Ile Lys
                    645                 650                 655

Phe Val Arg Gly Ser Thr Phe Lys Glu Ile Pro Met Thr Val Tyr Arg
            660                 665                 670

Pro Ala Met Thr Lys Ile His Ile Glu Gly Glu Pro Asp Phe Arg Leu
            675                 680                 685

Ile Lys Glu Gly Glu Thr Val Thr Glu Val Ile His Gly Glu Pro Val
690                 695                 700

Ile Lys Lys Tyr Thr Lys Ile Ile Asp Gly Val Pro Val Glu Ile Thr
705                 710                 715                 720

Glu Lys Glu Thr Arg Glu Glu Arg Ile Ile Thr Gly Pro Glu Ile Lys
                    725                 730                 735

Tyr Thr Arg Ile Ser Thr Gly Gly Glu Thr Glu Glu Thr Leu Gln
            740                 745                 750

Lys Phe Leu Gln Lys Glu Val Ser Lys Val Thr Lys Phe Ile Glu Gly
            755                 760                 765

Gly Asp Gly His Leu Phe Glu Asp Glu Ala Ile Lys Arg Leu Leu Gln
            770                 775                 780

Gly Asp Thr Pro Ala Lys Lys Ile Gln Ala Asn Lys Arg Val Gln Gly
785                 790                 795                 800

Ser Arg Arg Arg Ser Arg Glu Gly Arg Ser Gln
                    805                 810

<210> SEQ ID NO 4
<211> LENGTH: 27
<212> TYPE: PRT

<213> ORGANISM: Rattus sp.

<400> SEQUENCE: 4

Thr Thr Lys Ile Ile Thr Lys Val Val Glu Pro Lys Ile Lys Val Ile
1               5                   10                  15
Glu Gly Ser Leu Gln Pro Ile Ile Lys Thr Glu
            20                  25

<210> SEQ ID NO 5
<211> LENGTH: 2436
<212> TYPE: DNA
<213> ORGANISM: Rattus sp.

<400> SEQUENCE: 5

| | | | | | |
|---|---|---|---|---|---|
| atggttcctc | tcctgccctt | atctgctctg | ctgctgctgt | tcctgtgtga | cgttgacccc | 60 |
| gcaaatgcca | acagttacta | tgacaaggtc | ctagctcaca | gccgcatcag | gggtcgggat | 120 |
| cagggcccaa | atgtctgtgc | cctccagcag | attctgggca | ccaaaaagaa | atacttcagc | 180 |
| tcctgtaaga | actggtatca | aggtgctatc | tgcgggaaga | aaaccactgt | gctatatgaa | 240 |
| tgctgccccg | gctatatgag | aatggaaggg | atgaaaggct | gcccagcagt | gatgcccatt | 300 |
| gaccatgttt | atggcacgct | gggcatcgtg | ggagccacga | ccactcaaca | ctattctgat | 360 |
| gtctcgaagc | tcagggaaga | gattgaagga | aaagggtcct | acacatactt | cgcgccgagt | 420 |
| aacgaagctt | gggacaacct | ggattccgac | atccgcagag | gactagagaa | caatgtcaat | 480 |
| gttgagttac | tgaacgcttt | acacagccac | atggttaata | gagaatgct | aaccaaggac | 540 |
| ctgaaacacg | gcatggttat | tccttcaatg | tacaacaatc | tggggctttt | tatcaatcat | 600 |
| tatcccaatg | gggttgtcac | tgtgaactgt | gctcgagtaa | tccacgggaa | ccagattgcc | 660 |
| acaaatggtg | ttgtccatgt | catcgaccgt | gtcctgacac | aaattggcac | ctccatccaa | 720 |
| gacttcattg | aagcagaaga | tgagctttca | tcattcagag | cggctgccat | cacttctgac | 780 |
| cttttggagt | cccttggaag | agacggtcac | ttcacactct | tgctcccac | caatgaggct | 840 |
| ttcgagaaac | tcccacgagg | agtcctagaa | aggatcatgg | agacaaagt | ggcttctgaa | 900 |
| gctctcatga | agtaccacat | cctgaatacc | ctccagtgct | ctgaggctat | acaggagga | 960 |
| gcggtgtttg | agaccatgga | aggaaacact | attgaaatag | ggtgtgaggg | agacagcatc | 1020 |
| tccattaacg | gaatcaagat | ggtgaacaag | aaagacattg | tgacgaagaa | tggtgtcatc | 1080 |
| cacctgattg | atgaagtcct | cattcctgat | tctgctaaac | aagttattga | gctggctgga | 1140 |
| aaacagcaaa | ccactttcac | ggacctggta | gcccagttag | ggttggcgtc | ttctctgaag | 1200 |
| ccggatggag | agtacacgct | gttagcgcct | gtgaacaatg | cgttctctga | tgacactctg | 1260 |
| agcatggacc | agcgccttct | taagctaatt | ctgcaaaatc | acatattgaa | agtaaaagtc | 1320 |
| ggccttagtg | atctctacaa | tggacagatt | ctggagacca | ttggaggcaa | acaactccgt | 1380 |
| gtcttcgtgt | atcggacggc | tatctgcata | gaaaactcat | gcatggtgag | aggaagcaag | 1440 |
| caggggagga | acggtgccat | tcacatattc | cgagagatca | tccaaccggc | ggagaagtcc | 1500 |
| ctgcacgaaa | aactgcgcca | agataagcgc | ttcagcatct | tcctcagcct | cctcgaagct | 1560 |
| gcagatctga | agatcttct | gacacagccc | ggagattgga | ccttgtttgc | accaaccaat | 1620 |
| gatgccttca | agggaatgac | taatgaagaa | agggagattc | tgattgggga | taaaaatgct | 1680 |
| ctccaaaaca | tcattcttta | ccacctgacc | ccagggtttt | atattggaaa | gggatttgaa | 1740 |
| cccgagtca | ccaacatcct | gaagaccaca | cagggaagca | aaatctatgt | gaaaggagtc | 1800 |
| aatgagacgc | ttttggtgaa | tgagttgaag | tccaaagaat | ctgacatcat | gacaacaaac | 1860 |

```
ggcgtcattc acgttgtgga caaactcctc tatccagcag acattccggt tggaaatgat    1920
cagctcttgg aattactgaa caaactgata aatacatcc aaattaagtt cgttcgtggc     1980
agcaccttca agaaatccc catgactgtc tatagacctg caatgacgaa gatccacatt    2040
gaaggcgagc ctgacttcag gctgattaaa gaaggtgaaa cagtgacaga agtgatccac    2100
ggagaaccag tcattaaaaa gtacaccaaa atcatagacg gggttcctgt tgaaataact    2160
gaaaaagaga cccgggaaga acgcatcatc acaggtcctg agataaaata cactaggatt    2220
tccacaggag gtggggaaac agaagagacc ctgcagaaat tcttgcaaaa agaggtctcc    2280
aaggtcacaa agttcattga aggtggcgat ggtcacttat ttgaagatga ggcgattaaa    2340
agactgcttc agggagacac acctgcaaag aagatacaag ccaacaaaag ggttcaaggg    2400
tctagaaggc gatcaagaga aggccgttct cagtga                             2436
```

<210> SEQ ID NO 6
<211> LENGTH: 28
<212> TYPE: PRT
<213> ORGANISM: Rattus sp.

<400> SEQUENCE: 6

Glu Val Ser Lys Val Thr Lys Phe Ile Glu Gly Gly Asp Gly His Leu
1               5                   10                  15

Phe Glu Asp Glu Ala Ile Lys Arg Leu Leu Gln Gly
            20                  25

<210> SEQ ID NO 7
<211> LENGTH: 783
<212> TYPE: PRT
<213> ORGANISM: Rattus sp.

<400> SEQUENCE: 7

Met Val Pro Leu Leu Pro Leu Ser Ala Leu Leu Leu Phe Leu Cys
1               5                   10                  15

Asp Val Asp Pro Ala Asn Ala Asn Ser Tyr Tyr Asp Lys Val Leu Ala
                20                  25                  30

His Ser Arg Ile Arg Gly Arg Asp Gln Gly Pro Asn Val Cys Ala Leu
            35                  40                  45

Gln Gln Ile Leu Gly Thr Lys Lys Lys Tyr Phe Ser Ser Cys Lys Asn
        50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
        115                 120                 125

Glu Gly Lys Gly Ser Tyr Thr Tyr Phe Ala Pro Ser Asn Glu Ala Trp
    130                 135                 140

Asp Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
                165                 170                 175

Leu Thr Lys Asp Leu Lys His Gly Met Val Ile Pro Ser Met Tyr Asn
            180                 185                 190

```
Asn Leu Gly Leu Phe Ile Asn His Tyr Pro Asn Gly Val Thr Val
        195                 200                 205
Asn Cys Ala Arg Val Ile His Gly Asn Gln Ile Ala Thr Asn Gly Val
210                 215                 220
Val His Val Ile Asp Arg Val Leu Thr Gln Ile Gly Thr Ser Ile Gln
225                 230                 235                 240
Asp Phe Ile Glu Ala Glu Asp Glu Leu Ser Ser Phe Arg Ala Ala Ala
                245                 250                 255
Ile Thr Ser Asp Leu Leu Glu Ser Leu Gly Arg Asp Gly His Phe Thr
        260                 265                 270
Leu Phe Ala Pro Thr Asn Glu Ala Phe Glu Lys Leu Pro Arg Gly Val
        275                 280                 285
Leu Glu Arg Ile Met Gly Asp Lys Val Ala Ser Glu Ala Leu Met Lys
    290                 295                 300
Tyr His Ile Leu Asn Thr Leu Gln Cys Ser Glu Ala Ile Thr Gly Gly
305                 310                 315                 320
Ala Val Phe Glu Thr Met Glu Gly Asn Thr Ile Glu Ile Gly Cys Glu
                325                 330                 335
Gly Asp Ser Ile Ser Ile Asn Gly Ile Lys Met Val Asn Lys Lys Asp
        340                 345                 350
Ile Val Thr Lys Asn Gly Val Ile His Leu Ile Asp Glu Val Leu Ile
    355                 360                 365
Pro Asp Ser Ala Lys Gln Val Ile Glu Leu Ala Gly Lys Gln Gln Thr
370                 375                 380
Thr Phe Thr Asp Leu Val Ala Gln Leu Gly Leu Ala Ser Ser Leu Lys
385                 390                 395                 400
Pro Asp Gly Glu Tyr Thr Leu Leu Ala Pro Val Asn Asn Ala Phe Ser
                405                 410                 415
Asp Asp Thr Leu Ser Met Asp Gln Arg Leu Leu Lys Leu Ile Leu Gln
        420                 425                 430
Asn His Ile Leu Lys Val Lys Val Gly Leu Ser Asp Leu Tyr Asn Gly
    435                 440                 445
Gln Ile Leu Glu Thr Ile Gly Gly Lys Gln Leu Arg Val Phe Val Tyr
450                 455                 460
Arg Thr Ala Ile Cys Ile Glu Asn Ser Cys Met Val Arg Gly Ser Lys
465                 470                 475                 480
Gln Gly Arg Asn Gly Ala Ile His Ile Phe Arg Glu Ile Ile Gln Pro
                485                 490                 495
Ala Glu Lys Ser Leu His Glu Lys Leu Arg Gln Asp Lys Arg Phe Ser
        500                 505                 510
Ile Phe Leu Ser Leu Leu Glu Ala Ala Asp Leu Lys Asp Leu Leu Thr
    515                 520                 525
Gln Pro Gly Asp Trp Thr Leu Phe Ala Pro Thr Asn Asp Ala Phe Lys
530                 535                 540
Gly Met Thr Asn Glu Glu Arg Glu Ile Leu Ile Gly Asp Lys Asn Ala
545                 550                 555                 560
Leu Gln Asn Ile Ile Leu Tyr His Leu Thr Pro Gly Val Tyr Ile Gly
                565                 570                 575
Lys Gly Phe Glu Pro Gly Val Thr Asn Ile Leu Lys Thr Thr Gln Gly
        580                 585                 590
Ser Lys Ile Tyr Val Lys Gly Val Asn Glu Thr Leu Leu Val Asn Glu
    595                 600                 605
Leu Lys Ser Lys Glu Ser Asp Ile Met Thr Thr Asn Gly Val Ile His
```

```
            610              615              620
Val Val Asp Lys Leu Leu Tyr Pro Ala Asp Ile Pro Val Gly Asn Asp
625             630              635              640

Gln Leu Leu Glu Leu Leu Asn Lys Leu Ile Lys Tyr Ile Gln Ile Lys
            645              650              655

Phe Val Arg Gly Ser Thr Phe Lys Glu Ile Pro Met Thr Val Tyr Arg
            660              665              670

Pro Ala Met Thr Lys Ile His Ile Glu Gly Glu Pro Asp Phe Arg Leu
            675              680              685

Ile Lys Glu Gly Glu Thr Val Thr Glu Val Ile His Gly Glu Pro Val
690             695              700

Ile Lys Lys Tyr Thr Lys Ile Ile Asp Gly Val Pro Val Glu Ile Thr
705             710              715              720

Glu Lys Glu Thr Arg Glu Glu Arg Ile Ile Thr Gly Pro Glu Ile Lys
            725              730              735

Tyr Thr Arg Ile Ser Thr Gly Gly Glu Thr Glu Glu Thr Leu Gln
            740              745              750

Lys Phe Leu Gln Lys Asp Thr Pro Ala Lys Lys Ile Gln Ala Asn Lys
            755              760              765

Arg Val Gln Gly Ser Arg Arg Ser Arg Glu Gly Arg Ser Gln
770             775              780

<210> SEQ ID NO 8
<211> LENGTH: 2352
<212> TYPE: DNA
<213> ORGANISM: Rattus sp.

<400> SEQUENCE: 8
atggttcctc tcctgccctt atctgctctg ctgctgctgt tcctgtgtga cgttgacccc      60
gcaaatgcca acagttacta tgacaaggtc ctagctcaca gccgcatcag ggtcgggat     120
cagggcccaa atgtctgtgc cctccagcag attctgggca ccaaaaagaa atacttcagc    180
tcctgtaaga actggtatca aggtgctatc tgcgggaaga aaaccactgt gctatatgaa    240
tgctgccccg ctatatgag aatggaaggg atgaaaggct gcccagcagt gatgcccatt     300
gaccatgttt atggcacgct gggcatcgtg ggagccacga ccactcaaca ctattctgat    360
gtctcgaagc tcagggaaga gattgaagga aagggtcct acacatactt cgcgccgagt    420
aacgaagctt gggacaacct ggattccgac atccgcagag actagagaa caatgtcaat     480
gttgagttac tgaacgcttt acacagccac atggttaata agagaatgct aaccaaggac    540
ctgaaacacg gcatggttat tccttcaatg tacaacaatc tggggctttt tatcaatcat    600
tatcccaatg gggttgtcac tgtgaactgt gctcgagtaa tccacgggaa ccagattgcc    660
acaaatggtg ttgtccatgt catcgaccgt gtcctgacac aaattggcac ctccatccaa    720
gacttcattg aagcagaaga tgagctttca tcattcagag cggctgccat cacttctgac    780
cttttggagt cccttggaag agacggtcac ttcacactct tgctcccac caatgaggct    840
ttcgagaaac tcccacgagg agtcctagaa aggatcatgg agacaaagt ggcttctgaa     900
gctctcatga gtaccacat cctgaatacc ctccagtgct ctgaggctat acaggagga    960
gcggtgtttg agaccatgga aggaaacact attgaaatag ggtgtgaggg agacagcatc   1020
tccattaacg gaatcaagat ggtgaacaag aaagacattg tgacgaagaa tggtgtcatc   1080
cacctgattg atgaagtcct cattcctgat tctgctaaac aagttattga gctggctgga   1140
aaacagcaaa ccactttcac ggacctggta gcccagttag ggttggcgtc ttctctgaag   1200
```

```
ccggatggag agtacacgct gttagcgcct gtgaacaatg cgttctctga tgacactctg    1260
agcatggacc agcgccttct taagctaatt ctgcaaaatc acatattgaa agtaaaagtc    1320
ggccttagtg atctctacaa tggacagatt ctggagacca ttggaggcaa acaactccgt    1380
gtcttcgtgt atcggacggc tatctgcata gaaaactcat gcatggtgag aggaagcaag    1440
caggggagga acggtgccat tcacatattc cgagagatca tccaaccggc ggagaagtcc    1500
ctgcacgaaa aactgcgcca agataagcgc ttcagcatct tcctcagcct cctcgaagct    1560
gcagatctga aagatcttct gacacagccc ggagattgga ccttgtttgc accaaccaat    1620
gatgccttca agggaatgac taatgaagaa gggagattc tgattgggga taaaaatgct    1680
ctccaaaaca tcattcttta ccacctgacc ccaggggttt atattggaaa gggatttgaa    1740
cccggagtca ccaacatcct gaagaccaca caggaagca aatctatgt gaaaggagtc    1800 aatgagacgc ttttggtgaa tgagttgaag tccaaagaat ctgacatcat gacaacaaac    1860
ggcgtcattc acgttgtgga caaactcctc tatccagcag acattccggt tggaaatgat    1920
cagctcttgg aattactgaa caaactgata aaatacatcc aaattaagtt cgttcgtggc    1980
agcaccttca agaaatccc catgactgtc tatagacctg caatgacgaa gatccacatt    2040
gaaggcgagc ctgacttcag gctgattaaa gaaggtgaaa cagtgacaga agtgatccac    2100
ggagaaccag tcattaaaaa gtacaccaaa atcatagacg gggttcctgt tgaaataact    2160 gaaaagaga cccgggaaga acgcatcatc acaggtcctg agataaaata cactaggatt    2220
tccacaggag gtgggaaac agaagagacc ctgcagaaat tcttgcaaaa agacacacct    2280
gcaaagaaga tacaagccaa caaaggggtt caagggtcta gaaggcgatc aagagaaggc    2340
cgttctcagt ga                                                       2352
```

<210> SEQ ID NO 9
<211> LENGTH: 811
<212> TYPE: PRT
<213> ORGANISM: Mus musculus

<400> SEQUENCE: 9

```
Met Val Pro Leu Leu Pro Leu Tyr Ala Leu Leu Leu Phe Leu Cys
1               5                   10                  15

Asp Ile Asn Pro Ala Asn Ala Asn Ser Tyr Tyr Asp Lys Val Leu Ala
            20                  25                  30

His Ser Arg Ile Arg Gly Arg Asp Gln Gly Pro Asn Val Cys Ala Leu
        35                  40                  45

Gln Gln Ile Leu Gly Thr Lys Lys Tyr Phe Ser Ser Cys Lys Asn
    50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
                85                  90                  95

Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
        115                 120                 125

Glu Gly Lys Gly Ser Tyr Thr Tyr Phe Ala Pro Ser Asn Glu Ala Trp
    130                 135                 140

Glu Asn Leu Asp Ser Asp Ile Arg Arg Gly Leu Glu Asn Asn Val Asn
145                 150                 155                 160
```

-continued

Val Glu Leu Leu Asn Ala Leu His Ser His Met Val Asn Lys Arg Met
                165                 170                 175

Leu Thr Lys Asp Leu Lys His Gly Met Val Ile Pro Ser Met Tyr Asn
            180                 185                 190

Asn Leu Gly Leu Phe Ile Asn His Tyr Pro Asn Gly Val Val Thr Val
        195                 200                 205

Asn Cys Ala Arg Val Ile His Gly Asn Gln Ile Ala Thr Asn Gly Val
    210                 215                 220

Val His Val Ile Asp Arg Val Leu Thr Gln Ile Gly Thr Ser Ile Gln
225                 230                 235                 240

Asp Phe Leu Glu Ala Glu Asp Leu Ser Ser Phe Arg Ala Ala
                245                 250                 255

Ile Thr Ser Asp Leu Leu Glu Ser Leu Gly Arg Asp Gly His Phe Thr
            260                 265                 270

Leu Phe Ala Pro Thr Asn Glu Ala Phe Glu Lys Leu Pro Arg Gly Val
        275                 280                 285

Leu Glu Arg Ile Met Gly Asp Lys Val Ala Ser Glu Ala Leu Met Lys
    290                 295                 300

Tyr His Ile Leu Asn Thr Leu Gln Cys Ser Glu Ala Ile Thr Gly Gly
305                 310                 315                 320

Ala Val Phe Glu Thr Met Glu Gly Asn Thr Ile Glu Ile Gly Cys Glu
                325                 330                 335

Gly Asp Ser Ile Ser Ile Asn Gly Ile Lys Met Val Asn Lys Lys Asp
            340                 345                 350

Ile Val Thr Lys Asn Gly Val Ile His Leu Ile Asp Glu Val Leu Ile
        355                 360                 365

Pro Asp Ser Ala Lys Gln Val Ile Glu Leu Ala Gly Lys Gln Gln Thr
    370                 375                 380

Thr Phe Thr Asp Leu Val Ala Gln Leu Gly Leu Ala Ser Ser Leu Lys
385                 390                 395                 400

Pro Asp Gly Glu Tyr Thr Leu Leu Ala Pro Val Asn Asn Ala Phe Ser
                405                 410                 415

Asp Asp Thr Leu Ser Met Asp Gln Arg Leu Leu Lys Leu Ile Leu Gln
            420                 425                 430

Asn His Ile Leu Lys Val Lys Val Gly Leu Ser Asp Leu Tyr Asn Gly
        435                 440                 445

Gln Ile Leu Glu Thr Ile Gly Gly Lys Gln Leu Arg Val Phe Val Tyr
    450                 455                 460

Arg Thr Ala Ile Cys Ile Glu Asn Ser Cys Met Val Arg Gly Ser Lys
465                 470                 475                 480

Gln Gly Arg Asn Gly Ala Ile His Ile Phe Arg Glu Ile Ile Gln Pro
                485                 490                 495

Ala Glu Lys Ser Leu His Asp Lys Leu Arg Gln Asp Lys Arg Phe Ser
            500                 505                 510

Ile Phe Leu Ser Leu Leu Glu Ala Ala Asp Leu Lys Asp Leu Leu Thr
        515                 520                 525

Gln Pro Gly Asp Trp Thr Leu Phe Ala Pro Thr Asn Asp Ala Phe Lys
    530                 535                 540

Gly Met Thr Ser Glu Glu Arg Glu Leu Leu Ile Gly Asp Lys Asn Ala
545                 550                 555                 560

Leu Gln Asn Ile Ile Leu Tyr His Leu Thr Pro Gly Val Tyr Ile Gly
                565                 570                 575

Lys Gly Phe Glu Pro Gly Val Thr Asn Ile Leu Lys Thr Thr Gln Gly

```
                580             585             590
Ser Lys Ile Tyr Leu Lys Gly Val Asn Glu Thr Leu Leu Val Asn Glu
            595             600             605

Leu Lys Ser Lys Glu Ser Asp Ile Met Thr Thr Asn Gly Val Ile His
        610             615             620

Val Val Asp Lys Leu Leu Tyr Pro Ala Asp Ile Pro Val Gly Asn Asp
625             630             635             640

Gln Leu Leu Glu Leu Leu Asn Lys Leu Ile Lys Tyr Ile Gln Ile Lys
                645             650             655

Phe Val Arg Gly Ser Thr Phe Lys Glu Ile Pro Met Thr Val Tyr Arg
            660             665             670

Pro Ala Met Thr Lys Ile Gln Ile Glu Gly Asp Pro Asp Phe Arg Leu
        675             680             685

Ile Lys Glu Gly Glu Thr Val Thr Glu Val Ile His Gly Glu Pro Val
            690             695             700

Ile Lys Lys Tyr Thr Lys Ile Ile Asp Gly Val Pro Val Glu Ile Thr
705             710             715             720

Glu Lys Gln Thr Arg Glu Glu Arg Ile Ile Thr Gly Pro Glu Ile Lys
                725             730             735

Tyr Thr Arg Ile Ser Thr Gly Gly Gly Glu Thr Gly Glu Thr Leu Gln
            740             745             750

Lys Phe Leu Gln Lys Glu Val Ser Lys Val Thr Lys Phe Ile Glu Gly
        755             760             765

Gly Asp Gly His Leu Phe Glu Asp Glu Ile Lys Arg Leu Leu Gln
            770             775             780

Gly Asp Thr Pro Ala Lys Lys Ile Pro Ala Asn Lys Arg Val Gln Gly
785             790             795             800

Pro Arg Arg Arg Ser Arg Glu Gly Arg Ser Gln
                805             810

<210> SEQ ID NO 10
<211> LENGTH: 2436
<212> TYPE: DNA
<213> ORGANISM: Mus musculus

<400> SEQUENCE: 10
atggttcctc tcctgccctt atatgctctg ctgctgctgt tcctgtgtga tattaaccct      60
gcaaatgcca acagttacta tgacaaggtc ctggctcaca gccgcatcag gggtcgggat     120
cagggcccaa acgtctgtgc cctccagcaa attctgggca ccaaaaagaa atacttcagc     180
tcctgtaaga actggtatca aggtgctatc tgcgggaaga aaaccactgt gctatatgaa     240
tgctgccctg ctatatgag aatggaaggg atgaaaggct gccccgcagt gatgcctatt      300
gaccatgttt atggcacgct gggcattgtg ggagccacta ccactcagca ctactccgat     360
gtctcgaagc tgagagaaga gattgaagga aaagggtcat acacgtactt cgcgccgagt     420
aacgaggctt gggagaacct ggattctgac attcgcagag actggagaa caatgtcaat      480 gttgagctac tgaatgcctt acacagccac atggttaata agagaatgtt aaccaaggac     540
ctgaaacacg gcatggttat tccttcaatg tacaacaatc tggggctttt tattaaccat     600
tatcccaatg gggttgtcac tgtgaactgt gctcgagtca tccatgggaa ccagattgcc     660
acaaatggtg tcgtccatgt cattgaccgt gtcctgacac aaaattggta ctccatccaa     720
gacttccttg aagcagaaga cgacctttca tcatttagag cagccgccat cacctctgac     780
ctcttggagt cccttggaag agatggtcac ttcacgctct ttgctcccac caatgaagct     840
```

-continued

```
ttcgagaaac tgccacgagg tgtcctagaa aggatcatgg gagacaaagt ggcttctgaa      900
gctctcatga agtaccacat cctaaatacc ctccagtgct ctgaggccat cactggagga      960
gccgtgtttg agaccatgga aggaaacact attgagatag ggtgcgaagg ggacagtatc     1020
tccattaacg gaatcaagat ggtgaacaag aaagacattg tgactaagaa tggtgtcatc     1080
cacctgattg atgaagtcct cattcctgat tctgccaaac aagttattga gctggctgga     1140
aaacagcaaa ccactttcac cgacctggta gcccaattag gcttggcatc ctctctgaag     1200
ccagatggag agtacacctt attagcacct gtgaacaatg cgttctctga tgacactctg     1260
agcatggacc aacgccttct taagctaatt ctgcaaaatc acatattgaa agtaaaagtt     1320
ggccttagcg acctctacaa tggacagata ctggaaacca ttggaggcaa acaactccga     1380
gtctttgtgt atcggacggc tatctgcata gaaaactcat gcatggtgag aggaagcaag     1440
cagggaagga atggtgccat tcacatattc cgagaaatca tccaaccagc agagaaatcc     1500
ctgcacgaca agctgcggca agacaagcgc tttagcatct tcctcagcct ccttgaagct     1560
gcagatttga aagatctcct gacacagccc ggagattgga ccttgtttgc accaaccaat     1620
gatgccttca agggaatgac tagcgaagaa agggagcttc tgattgggga taaaaatgct     1680
ctccaaaaca tcattcttta tcacctgacc ccaggggttt atattggaaa gggattcgaa     1740
cccggagtca ctaatatcct gaagaccaca caggggaagca aaatctatct gaaggagta     1800
aacgaaacgc ttctagtgaa tgagttgaag tccaagaat ctgacatcat gacgacaaat      1860
ggtgtcatcc acgtcgtgga caaactcctc tatccagcag atattccagt tggaaatgat     1920
cagctcttgg aattactgaa caaactgata aaatacatcc aaatcaagtt tgttcgtggc     1980
agcaccttca agaaatccc catgactgtc tatagacctg caatgacgaa gatccaaatt     2040
gaaggtgatc ccgacttcag gctgattaaa gaaggcgaaa cggtgacaga agtgatccac     2100
ggagagccag tcattaaaaa gtacaccaaa atcatagatg gagttcctgt tgaaataact     2160
gaaaaacaga ctcgggaaga acgaatcatt acaggtcctg agataaaata taccaggatt     2220
tccacaggag gtggagaaac aggagagacc ttgcagaaat tcttgcaaaa agaggtctcc     2280
aaggtcacaa agttcattga aggtggcgat ggtcacttat ttgaagatga ggagattaaa     2340
agactgcttc agggagacac acctgcaaag aagataccag ccaacaaaag ggttcaaggg     2400
cctagaagac gatcaagaga aggccgttct cagtga                              2436
```

```
<210> SEQ ID NO 11
<211> LENGTH: 783
<212> TYPE: PRT
<213> ORGANISM: Mus musculus

<400> SEQUENCE: 11

Met Val Pro Leu Leu Pro Leu Tyr Ala Leu Leu Leu Phe Leu Cys
 1               5                  10                  15

Asp Ile Asn Pro Ala Asn Ala Asn Ser Tyr Tyr Asp Lys Val Leu Ala
                20                  25                  30

His Ser Arg Ile Arg Gly Arg Asp Gln Gly Pro Asn Val Cys Ala Leu
            35                  40                  45

Gln Gln Ile Leu Gly Thr Lys Lys Lys Tyr Phe Ser Ser Cys Lys Asn
        50                  55                  60

Trp Tyr Gln Gly Ala Ile Cys Gly Lys Lys Thr Thr Val Leu Tyr Glu
65                  70                  75                  80

Cys Cys Pro Gly Tyr Met Arg Met Glu Gly Met Lys Gly Cys Pro Ala
```

```
            85                  90                  95
Val Met Pro Ile Asp His Val Tyr Gly Thr Leu Gly Ile Val Gly Ala
            100                 105                 110

Thr Thr Thr Gln His Tyr Ser Asp Val Ser Lys Leu Arg Glu Glu Ile
            115                 120                 125

Glu Gly Lys Gly Ser Tyr Thr Tyr Phe Ala Pro Ser Asn Glu Ala Trp
            130                 135                 140

Glu Asn Leu Asp Ser Asp Ile Arg Arg Gly Leu Glu Asn Asn Val Asn
145                 150                 155                 160

Val Glu Leu Leu Asn Ala Leu His Ser His Met Val Asn Lys Arg Met
            165                 170                 175

Leu Thr Lys Asp Leu Lys His Gly Met Val Ile Pro Ser Met Tyr Asn
            180                 185                 190

Asn Leu Gly Leu Phe Ile Asn His Tyr Pro Asn Gly Val Val Thr Val
            195                 200                 205

Asn Cys Ala Arg Val Ile His Gly Asn Gln Ile Ala Thr Asn Gly Val
            210                 215                 220

Val His Val Ile Asp Arg Val Leu Thr Gln Ile Gly Thr Ser Ile Gln
225                 230                 235                 240

Asp Phe Leu Glu Ala Glu Asp Leu Ser Ser Phe Arg Ala Ala Ala
            245                 250                 255

Ile Thr Ser Asp Leu Leu Glu Ser Leu Gly Arg Asp Gly His Phe Thr
            260                 265                 270

Leu Phe Ala Pro Thr Asn Glu Ala Phe Glu Lys Leu Pro Arg Gly Val
            275                 280                 285

Leu Glu Arg Ile Met Gly Asp Lys Val Ala Ser Glu Ala Leu Met Lys
            290                 295                 300

Tyr His Ile Leu Asn Thr Leu Gln Cys Ser Glu Ala Ile Thr Gly Gly
305                 310                 315                 320

Ala Val Phe Glu Thr Met Glu Gly Asn Thr Ile Glu Ile Gly Cys Glu
            325                 330                 335

Gly Asp Ser Ile Ser Ile Asn Gly Ile Lys Met Val Asn Lys Lys Asp
            340                 345                 350

Ile Val Thr Lys Asn Gly Val Ile His Leu Ile Asp Glu Val Leu Ile
            355                 360                 365

Pro Asp Ser Ala Lys Gln Val Ile Glu Leu Ala Gly Lys Gln Gln Thr
            370                 375                 380

Thr Phe Thr Asp Leu Val Ala Gln Leu Gly Leu Ala Ser Ser Leu Lys
385                 390                 395                 400

Pro Asp Gly Glu Tyr Thr Leu Leu Ala Pro Val Asn Asn Ala Phe Ser
            405                 410                 415

Asp Asp Thr Leu Ser Met Asp Gln Arg Leu Leu Lys Leu Ile Leu Gln
            420                 425                 430

Asn His Ile Leu Lys Val Lys Val Gly Leu Ser Asp Leu Tyr Asn Gly
            435                 440                 445

Gln Ile Leu Glu Thr Ile Gly Gly Lys Gln Leu Arg Val Phe Val Tyr
            450                 455                 460

Arg Thr Ala Ile Cys Ile Glu Asn Ser Cys Met Val Arg Gly Ser Lys
465                 470                 475                 480

Gln Gly Arg Asn Gly Ala Ile His Ile Phe Arg Glu Ile Ile Gln Pro
            485                 490                 495

Ala Glu Lys Ser Leu His Asp Lys Leu Arg Gln Asp Lys Arg Phe Ser
            500                 505                 510
```

```
Ile Phe Leu Ser Leu Leu Glu Ala Ala Asp Leu Lys Asp Leu Leu Thr
            515                 520                 525

Gln Pro Gly Asp Trp Thr Leu Phe Ala Pro Thr Asn Asp Ala Phe Lys
        530                 535                 540

Gly Met Thr Ser Glu Glu Arg Glu Leu Leu Ile Gly Asp Lys Asn Ala
545                 550                 555                 560

Leu Gln Asn Ile Ile Leu Tyr His Leu Thr Pro Gly Val Tyr Ile Gly
                565                 570                 575

Lys Gly Phe Glu Pro Gly Val Thr Asn Ile Leu Lys Thr Thr Gln Gly
            580                 585                 590

Ser Lys Ile Tyr Leu Lys Gly Val Asn Glu Thr Leu Leu Val Asn Glu
        595                 600                 605

Leu Lys Ser Lys Glu Ser Asp Ile Met Thr Thr Asn Gly Val Ile His
610                 615                 620

Val Val Asp Lys Leu Leu Tyr Pro Ala Asp Ile Pro Val Gly Asn Asp
625                 630                 635                 640

Gln Leu Leu Glu Leu Leu Asn Lys Leu Ile Lys Tyr Ile Gln Ile Lys
                645                 650                 655

Phe Val Arg Gly Ser Thr Phe Lys Glu Ile Pro Met Thr Val Tyr Arg
            660                 665                 670

Pro Ala Met Thr Lys Ile Gln Ile Glu Gly Asp Pro Asp Phe Arg Leu
        675                 680                 685

Ile Lys Glu Gly Glu Thr Val Thr Glu Val Ile His Gly Glu Pro Val
690                 695                 700

Ile Lys Lys Tyr Thr Lys Ile Ile Asp Gly Val Pro Val Glu Ile Thr
705                 710                 715                 720

Glu Lys Gln Thr Arg Glu Glu Arg Ile Ile Thr Gly Pro Glu Ile Lys
                725                 730                 735

Tyr Thr Arg Ile Ser Thr Gly Gly Glu Thr Gly Glu Thr Leu Gln
            740                 745                 750

Lys Phe Leu Gln Lys Asp Thr Pro Ala Lys Lys Ile Pro Ala Asn Lys
        755                 760                 765

Arg Val Gln Gly Pro Arg Arg Ser Arg Glu Gly Arg Ser Gln
770                 775                 780

<210> SEQ ID NO 12
<211> LENGTH: 2352
<212> TYPE: DNA
<213> ORGANISM: Mus musculus

<400> SEQUENCE: 12
atggttcctc tcctgccctt atatgctctg ctgctgctgt tcctgtgtga tattaaccct      60
gcaaatgcca acagttacta tgacaaggtc ctggctcaca gccgcatcag gggtcgggat     120
cagggcccaa acgtctgtgc cctccagcaa attctgggca ccaaaaagaa atacttcagc     180
tcctgtaaga actggtatca aggtgctatc tgcgggaaga aaaccactgt gctatatgaa     240
tgctgccctg ctatatgag aatggaaggg atgaaaggct gccccgcagt gatgcctatt      300
gaccatgttt atggcacgct gggcattgtg gagccactac ccactcagca ctactccgat     360
gtctcgaagc tgagagaaga gattgaagga aaagggtcat acacgtactt cgcgccgagt     420
aacgaggctt gggagaacct ggattctgac attcgcagag actggagaa caatgtcaat      480 gttgagctac tgaatgcctt acacagccac atggttaata agagaatgtt aaccaaggac     540
ctgaaacacg gcatggttat tccttcaatg tacaacaatc tggggctttt tattaaccat     600
```

```
tatcccaatg gggttgtcac tgtgaactgt gctcgagtca tccatgggaa ccagattgcc      660
acaaatggtg tcgtccatgt cattgaccgt gtcctgacac aaattggtac ctccatccaa      720
gacttccttg aagcagaaga cgacctttca tcatttagag cagccgccat cacctctgac      780
ctcttggagt cccttggaag agatggtcac ttcacgctct tgctcccac caatgaagct       840 ttcgagaaac tgccacgagg tgtcctagaa aggatcatgg agacaaagt ggcttctgaa       900 gctctcatga agtaccacat cctaaatacc ctccagtgct ctgaggccat cactggagga      960
gccgtgtttg agaccatgga aggaaacact attgagatag ggtgcgaagg ggacagtatc     1020
tccattaacg gaatcaagat ggtgaacaag aaagacattg tgactaagaa tggtgtcatc     1080
cacctgattg atgaagtcct cattcctgat ctgccaaac aagttattga gctggctgga      1140
aaacagcaaa ccactttcac cgacctggta gcccaattag gcttggcatc ctctctgaag     1200
ccagatggag agtacacctt attagcacct gtgaacaatg cgttctctga tgacactctg     1260
agcatggacc aacgccttct taagctaatt ctgcaaaatc acatattgaa agtaaaagtt     1320
ggccttagcg acctctacaa tggacagata ctggaaacca ttggaggcaa acaactccga     1380
gtctttgtgt atcggacggc tatctgcata gaaaactcat gcatggtgag aggaagcaag     1440
cagggaagga atggtgccat tcacatattc cgagaaatca tccaaccagc agagaaatcc     1500
ctgcacgaca agctgcggca agacaagcgc tttagcatct tcctcagcct ccttgaagct     1560
gcagatttga aagatctcct gacacagccc ggagattgga ccttgtttgc accaaccaat     1620
gatgccttca agggaatgac tagcgaagaa agggagcttc tgattgggga taaaaatgct     1680
ctccaaaaca tcattcttta tcacctgacc ccaggggttt atattggaaa gggattcgaa     1740
cccggagtca ctaatatcct gaagaccaca cagggaagca aatctatct gaaaggagta      1800 aacgaaacgc ttctagtgaa tgagttgaag tccaaagaat ctgacatcat gacgacaaat     1860
ggtgtcatcc acgtcgtgga caaactcctc tatccagcag atattccagt tggaaatgat     1920
cagctcttgg aattactgaa caaactgata aaatacatcc aaatcaagtt tgttcgtggc     1980
agcaccttca agaaatccc catgactgtc tatagacctg caatgacgaa gatccaaatt     2040
gaaggtgatc ccgacttcag gctgattaaa gaaggcgaaa cggtgacaga agtgatccac     2100
ggagagccag tcattaaaaa gtacaccaaa atcatagatg gagttcctgt tgaaataact     2160
gaaaaacaga ctcgggaaga acgaatcatt acaggtcctg agataaaata taccaggatt     2220
tccacaggag gtggagaaac aggagagacc ttgcagaaat tcttgcaaaa agacacacct     2280
gcaaagaaga taccagccaa caaaagggtt caagggccta agacgatc aagagaaggc       2340 cgttctcagt ga                                                         2352
```

<210> SEQ ID NO 13
<211> LENGTH: 809
<212> TYPE: PRT
<213> ORGANISM: Homo sapiens

<400> SEQUENCE: 13

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr

```
            50                  55                  60
Lys Lys Ser Ile Cys Gly Gln Lys Thr Thr Val Leu Tyr Glu Cys Cys
 65                  70                  75                  80

Pro Gly Tyr Met Arg Met Glu Gly Met Lys Gly Cys Pro Ala Val Leu
                 85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
                115                 120                 125

Lys Gly Ser Phe Thr Tyr Phe Ala Pro Ser Asn Glu Ala Trp Asp Asn
        130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
                180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ile Thr
                245                 250                 255

Ser Asp Ile Leu Glu Ala Leu Gly Arg Asp Gly His Phe Thr Leu Phe
        260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
        290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
                340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
        370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
        450                 455                 460

Ala Val Cys Ile Glu Asn Ser Cys Met Glu Lys Gly Ser Lys Gln Gly
465                 470                 475                 480
```

```
Arg Asn Gly Ala Ile His Ile Phe Arg Glu Ile Ile Lys Pro Ala Glu
            485                 490                 495

Lys Ser Leu His Glu Lys Leu Lys Gln Asp Lys Arg Phe Ser Thr Phe
        500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
        675                 680                 685

Glu Gly Glu Thr Ile Thr Glu Val Ile His Gly Glu Pro Ile Ile Lys
    690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
                725                 730                 735

Arg Ile Ser Thr Gly Gly Gly Glu Thr Glu Glu Thr Leu Lys Lys Leu
            740                 745                 750

Leu Gln Glu Glu Val Thr Lys Val Thr Lys Phe Ile Glu Gly Gly Asp
        755                 760                 765

Gly His Leu Phe Glu Asp Glu Ile Lys Arg Leu Leu Gln Gly Asp
    770                 775                 780

Thr Pro Val Arg Lys Leu Gln Ala Asn Lys Lys Val Gln Gly Ser Arg
785                 790                 795                 800

Arg Arg Leu Arg Glu Gly Arg Ser Gln
                805

<210> SEQ ID NO 14
<211> LENGTH: 2430
<212> TYPE: DNA
<213> ORGANISM: Homo sapiens

<400> SEQUENCE: 14
atgattccct ttttacccat gttttctcta ctattgctgc ttattgttaa ccctataaac    60
gccaacaatc attatgacaa gatcttggct catagtcgta tcaggggtcg ggaccaaggc   120
ccaaatgtct gtgcccttca acagattttg ggcaccaaaa agaaatactt cagcacttgt   180
aagaactggt ataaaaagtc catctgtgga cagaaaacga ctgtgttata tgaatgttgc   240
```

```
cctggttata tgagaatgga aggaatgaaa ggctgcccag cagttttgcc cattgaccat    300
gtttatggca ctctgggcat cgtgggagcc accacaacgc agcgctattc tgacgcctca    360
aaactgaggg aggagatcga gggaaaggga tccttcactt actttgcacc gagtaatgag    420
gcttgggaca acttggattc tgatatccgt agaggtttgg agagcaacgt gaatgttgaa    480
ttactgaatg ctttacatag tcacatgatt aataagagaa tgttgaccaa ggacttaaaa    540
aatggcatga ttattccttc aatgtataac aatttggggc ttttcattaa ccattatcct    600
aatggggttg tcactgttaa ttgtgctcga atcatccatg gaaccagat tgcaacaaat     660 ggtgttgtcc atgtcattga ccgtgtgctt acacaaattg gtacctcaat tcaagacttc    720
attgaagcag aagatgacct ttcatctttt agagcagctg ccatcacatc ggacatattg    780
gaggcccttg aagagacgg tcacttcaca ctctttgctc ccaccaatga ggcttttgag     840
aaacttccac gaggtgtcct agaaaggatc atgggagaca aagtggcttc cgaagctctt    900
atgaagtacc acatcttaaa tactctccag tgttctgagt ctattatggg aggagcagtc    960
tttgagacgc tggaaggaaa tacaattgag ataggatgtg acggtgacag tataacagta    1020
aatgaaatca aaatggtgaa caaaaaggat attgtgacaa ataatggtgt gatccatttg    1080
attgatcagg tcctaattcc tgattctgcc aaacaagtta ttgagctggc tggaaaacag    1140
caaaccacct tcacggatct tgtggcccaa ttaggcttgg catctgctct gaggccagat    1200
ggagaataca ctttgctggc acctgtgaat aatgcatttt ctgatgatac tctcagcatg    1260
gatcagcgcc tccttaaatt aattctgcag aatcacatat tgaaagtaaa agttggcctt    1320
aatgagcttt acaacgggca atactggaa accatcggag gcaaacagct cagagtcttc    1380
gtatatcgta cagctgtctg cattgaaaat tcatgcatgg agaaagggag taagcaaggg    1440
agaaacggtg cgattcacat attccgcgag atcatcaagc cagcagagaa atccctccat    1500
gaaaagttaa acaagataa gcgctttagc accttcctca gcctacttga agctgcagac    1560
ttgaaagagc tcctgacaca acctggagac tggacattat ttgtgccaac caatgatgct    1620
tttaagggaa tgactagtga agaaaaagaa attctgatac gggacaaaaa tgctcttcaa    1680
aacatcattc tttatcacct gacaccagga gttttcattg gaaaaggatt tgaacctggt    1740
gttactaaca tttaaagac cacacaagga agcaaaatct ttctgaaaga agtaaatgat    1800
acacttctgg tgaatgaatt gaaatcaaaa gaatctgaca tcatgacaac aaatggtgta    1860
attcatgttg tagataaact cctctatcca gcagacacac ctgttggaaa tgatcaactg    1920
ctggaaatac ttaataaatt aatcaaatac atccaaatta gtttgttcg tggtagcacc     1980 ttcaaagaaa tccccgtgac tgtctataga cccacactaa caaaagtcaa aattgaaggt    2040
gaacctgaat tcagactgat taagaaggt gaaacaataa ctgaagtgat ccatggagag    2100
ccaattatta aaaatacac caaaatcatt gatggagtgc ctgtggaaat aactgaaaaa    2160
gagacacgag aagaacgaat cattacaggt cctgaaataa aatacactag gatttctact    2220
ggaggtggag aaacagaaga aactctgaag aaattgttac aagaagaggt caccaaggtc    2280
accaaattca ttgaaggtgg tgatggtcat ttatttgaag atgaagaaat taaaagactg    2340 cttcaggag acacacccgt gaggaagttg caagccaaca aaaagttca aggatctaga     2400 agacgattaa gggaaggtcg ttctcagtga                                     2430
```

<210> SEQ ID NO 15
<211> LENGTH: 781
<212> TYPE: PRT

<213> ORGANISM: Homo sapiens

<400> SEQUENCE: 15

```
Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400
```

-continued

Gly Glu Tyr Thr Leu Leu Ala Pro Val Asn Asn Ala Phe Ser Asp Asp
                405                 410                 415
Thr Leu Ser Met Asp Gln Arg Leu Leu Lys Leu Ile Leu Gln Asn His
            420                 425                 430
Ile Leu Lys Val Lys Val Gly Leu Asn Glu Leu Tyr Asn Gly Gln Ile
        435                 440                 445
Leu Glu Thr Ile Gly Gly Lys Gln Leu Arg Val Phe Val Tyr Arg Thr
    450                 455                 460
Ala Val Cys Ile Glu Asn Ser Cys Met Glu Lys Gly Ser Lys Gln Gly
465                 470                 475                 480
Arg Asn Gly Ala Ile His Ile Phe Arg Glu Ile Ile Lys Pro Ala Glu
                485                 490                 495
Lys Ser Leu His Glu Lys Leu Lys Gln Asp Lys Arg Phe Ser Thr Phe
            500                 505                 510
Leu Ser Leu Leu Glu Ala Ala Asp Leu Lys Glu Leu Leu Thr Gln Pro
        515                 520                 525
Gly Asp Trp Thr Leu Phe Val Pro Thr Asn Asp Ala Phe Lys Gly Met
    530                 535                 540
Thr Ser Glu Glu Lys Glu Ile Leu Ile Arg Asp Lys Asn Ala Leu Gln
545                 550                 555                 560
Asn Ile Ile Leu Tyr His Leu Thr Pro Gly Val Phe Ile Gly Lys Gly
                565                 570                 575
Phe Glu Pro Gly Val Thr Asn Ile Leu Lys Thr Thr Gln Gly Ser Lys
            580                 585                 590
Ile Phe Leu Lys Glu Val Asn Asp Thr Leu Leu Val Asn Glu Leu Lys
        595                 600                 605
Ser Lys Glu Ser Asp Ile Met Thr Thr Asn Gly Val Ile His Val Val
    610                 615                 620
Asp Lys Leu Leu Tyr Pro Ala Asp Thr Pro Val Gly Asn Asp Gln Leu
625                 630                 635                 640
Leu Glu Ile Leu Asn Lys Leu Ile Lys Tyr Ile Gln Ile Lys Phe Val
                645                 650                 655
Arg Gly Ser Thr Phe Lys Glu Ile Pro Val Thr Val Tyr Arg Pro Thr
            660                 665                 670
Leu Thr Lys Val Lys Ile Glu Gly Glu Pro Glu Phe Arg Leu Ile Lys
        675                 680                 685
Glu Gly Glu Thr Ile Thr Glu Val Ile His Gly Glu Pro Ile Ile Lys
    690                 695                 700
Lys Tyr Thr Lys Ile Ile Asp Gly Val Pro Val Glu Ile Thr Glu Lys
705                 710                 715                 720
Glu Thr Arg Glu Glu Arg Ile Ile Thr Gly Pro Glu Ile Lys Tyr Thr
                725                 730                 735
Arg Ile Ser Thr Gly Gly Gly Glu Thr Glu Glu Thr Leu Lys Lys Leu
            740                 745                 750
Leu Gln Glu Asp Thr Pro Val Arg Lys Leu Gln Ala Asn Lys Lys Val
        755                 760                 765
Gln Gly Ser Arg Arg Leu Arg Glu Gly Arg Ser Gln
    770                 775                 780

<210> SEQ ID NO 16
<211> LENGTH: 2346
<212> TYPE: DNA
<213> ORGANISM: Homo sapiens

<400> SEQUENCE: 16

```
atgattccct ttttacccat gttttctcta ctattgctgc ttattgttaa ccctataaac      60
gccaacaatc attatgacaa gatcttggct catagtcgta tcaggggtcg ggaccaaggc     120
ccaaatgtct gtgcccttca acagattttg ggcaccaaaa agaaatactt cagcacttgt     180
aagaactggt ataaaagtc catctgtgga cagaaaacga ctgtgttata tgaatgttgc      240
cctggttata tgagaatgga aggaatgaaa ggctgcccag cagttttgcc cattgaccat     300
gtttatggca ctctgggcat cgtgggagcc accacaacgc agcgctattc tgacgcctca     360
aaactgaggg aggagatcga gggaaaggga tccttcactt actttgcacc gagtaatgag     420
gcttgggaca acttggattc tgatatccgt agaggtttgg agagcaacgt gaatgttgaa     480
ttactgaatg ctttacatag tcacatgatt aataagagaa tgttgaccaa ggacttaaaa     540
aatggcatga ttattccttc aatgtataac aatttggggc ttttcattaa ccattatcct     600
aatggggttg tcactgttaa ttgtgctcga atcatccatg gaaccagat gcaacaaat      660 ggtgttgtcc atgtcattga ccgtgtgctt acacaaattg gtacctcaat tcaagacttc     720
attgaagcag aagatgacct ttcatctttt agagcagctg ccatcacatc ggacatattg     780
gaggcccttg aagagacgg tcacttcaca ctctttgctc ccaccaatga ggcttttgag      840
aaacttccac gaggtgtcct agaaaggatc atgggagaca agtggcttc cgaagctctt      900 atgaagtacc acatcttaaa tactctccag tgttctgagt ctattatggg aggagcagtc     960
tttgagacgc tggaaggaaa tacaattgag ataggatgtg acggtgacag tataacagta    1020
aatggaatca aaatggtgaa caaaaaggat attgtgacaa ataatggtgt gatccatttg    1080
attgatcagg tcctaattcc tgattctgcc aaacaagtta ttgagctggc tggaaaacag    1140
caaaccacct tcacggatct tgtgcccaa ttaggcttgg catctgctct gaggccagat     1200
ggagaataca ctttgctggc acctgtgaat aatgcatttt ctgatgatac tctcagcatg    1260
gatcagcgcc tccttaaatt aattctgcag aatcacatat tgaaagtaaa agttggcctt    1320
aatgagcttt acaacgggca aatactggaa accatcggag gcaaacagct cagagtcttc    1380
gtatatcgta cagctgtctg cattgaaaat tcatgcatgg agaaagggag taagcaaggg    1440
agaaacggtg cgattcacat attccgcgag atcatcaagc cagcagagaa atccctccat    1500
gaaaagttaa acaagataa gcgctttagc accttcctca gcctacttga agctgcagac    1560
ttgaaagagc tcctgacaca acctggagac tggacattat ttgtgccaac caatgatgct    1620
tttaagggaa tgactagtga agaaaaagaa attctgatac gggacaaaaa tgctcttcaa    1680
aacatcattc tttatcacct gacaccagga gttttcattg gaaaaggatt tgaacctggt    1740
gttactaaca tttttaaagac cacacaagga agcaaaatct ttctgaaaga agtaaatgat    1800
acacttctgg tgaatgaatt gaaatcaaaa gaatctgaca tcatgacaac aaatggtgta    1860
attcatgttg tagataaact cctctatcca gcagacacac tgttggaaa tgatcaactg    1920 ctggaaatac ttaataaatt aatcaaatac atccaaatta gtttgttcg tggtagcacc    1980 ttcaaagaaa tccccgtgac tgtctataga cccacactaa caaaagtcaa aattgaaggt    2040
gaacctgaat tcagactgat taaagaaggt gaaacaataa ctgaagtgat ccatggagag    2100
ccaattatta aaaatacac caaatcatt gatggagtgc ctgtggaaat aactgaaaaa     2160
gagacacgag aagaacgaat cattacaggt cctgaaataa aatacactag gatttctact    2220
ggaggtggag aaacagaaga aactctgaag aaattgttac aagaagacac acccgtgagg    2280
aagttgcaag ccaacaaaaa agttcaagga tctagaagac gattaaggga aggtcgttct    2340
``` cagtga                                                                                    2346

<210> SEQ ID NO 17
<211> LENGTH: 28
<212> TYPE: PRT
<213> ORGANISM: Mus musculus

<400> SEQUENCE: 17

Glu Val Ser Lys Val Thr Lys Phe Ile Glu Gly Gly Asp Gly His Leu
1               5                   10                  15

Phe Glu Asp Glu Glu Ile Lys Arg Leu Leu Gln Gly
            20                  25

<210> SEQ ID NO 18
<211> LENGTH: 28
<212> TYPE: PRT
<213> ORGANISM: Homo sapiens

<400> SEQUENCE: 18

Glu Val Thr Lys Val Thr Lys Phe Ile Glu Gly Gly Asp Gly His Leu
1               5                   10                  15

Phe Glu Asp Glu Glu Ile Lys Arg Leu Leu Gln Gly
            20                  25

<210> SEQ ID NO 19
<211> LENGTH: 6
<212> TYPE: PRT
<213> ORGANISM: Homo sapiens

<400> SEQUENCE: 19

Val Thr Lys Val Thr Lys
1               5

<210> SEQ ID NO 20
<211> LENGTH: 7
<212> TYPE: PRT
<213> ORGANISM: Homo sapiens

<400> SEQUENCE: 20

Phe Glu Asp Glu Glu Ile Lys
1               5

<210> SEQ ID NO 21
<211> LENGTH: 5
<212> TYPE: PRT
<213> ORGANISM: Homo sapiens

<400> SEQUENCE: 21

Thr Lys Val Thr Lys
1               5

<210> SEQ ID NO 22
<211> LENGTH: 8
<212> TYPE: PRT
<213> ORGANISM: Homo sapiens

<400> SEQUENCE: 22

Gln Gly Asp Thr Pro Val Arg Lys
1               5

<210> SEQ ID NO 23
<211> LENGTH: 23
<212> TYPE: DNA
<213> ORGANISM: Artificial

<220> FEATURE:
<223> OTHER INFORMATION: Primer 1

<400> SEQUENCE: 23
gttcattgaa ggtggcgatg gtc                                              23

<210> SEQ ID NO 24
<211> LENGTH: 24
<212> TYPE: DNA
<213> ORGANISM: Artificial
<220> FEATURE:
<223> OTHER INFORMATION: Primer 2

<400> SEQUENCE: 24
gagataaaat ccctgcatgg tcct                                             24

<210> SEQ ID NO 25
<211> LENGTH: 25
<212> TYPE: DNA
<213> ORGANISM: Artificial
<220> FEATURE:
<223> OTHER INFORMATION: Primer 3

<400> SEQUENCE: 25
cacggtcgat gacatggaca acacc                                            25

<210> SEQ ID NO 26
<211> LENGTH: 22
<212> TYPE: DNA
<213> ORGANISM: Artificial
<220> FEATURE:
<223> OTHER INFORMATION: Primer 4

<400> SEQUENCE: 26
acggagctca gggctgaaga tg                                               22

<210> SEQ ID NO 27
<211> LENGTH: 31
<212> TYPE: DNA
<213> ORGANISM: Artificial
<220> FEATURE:
<223> OTHER INFORMATION: Primer 5

<400> SEQUENCE: 27
aagctagcga agatggttcc tctcctgccc t                                     31

<210> SEQ ID NO 28
<211> LENGTH: 20
<212> TYPE: DNA
<213> ORGANISM: Artificial
<220> FEATURE:
<223> OTHER INFORMATION: Primer 6

<400> SEQUENCE: 28
ctttgggttt ttccagcctc                                                  20

<210> SEQ ID NO 29
<211> LENGTH: 22
<212> TYPE: DNA
<213> ORGANISM: Artificial
<220> FEATURE:
<223> OTHER INFORMATION: Primer 7

<400> SEQUENCE: 29
ccccatgact gtctatagac ct                                               22

```
<210> SEQ ID NO 30
<211> LENGTH: 22
<212> TYPE: DNA
<213> ORGANISM: Artificial
<220> FEATURE:
<223> OTHER INFORMATION: Primer 8

<400> SEQUENCE: 30
atttccctta aaaatcagat tg                                            22

<210> SEQ ID NO 31
<211> LENGTH: 29
<212> TYPE: PRT
<213> ORGANISM: Artificial
<220> FEATURE:
<223> OTHER INFORMATION: antigen peptide of example 6

<400> SEQUENCE: 31

Cys Glu Val Thr Lys Val Thr Lys Phe Ile Glu Gly Gly Asp Gly His
1               5                   10                  15

Leu Phe Glu Asp Glu Glu Ile Lys Arg Leu Leu Gln Gly
            20                  25
```